(12) United States Patent
Duxbury et al.

(10) Patent No.: US 12,668,782 B1
(45) Date of Patent: Jun. 30, 2026

(54) PORTABLE INCUBATION SYSTEM

(71) Applicant: TRANS OVA GENETICS, L.C., Sioux Center, IA (US)

(72) Inventors: Shannon Leigh Duxbury, Sioux Center, IA (US); Matthew Bryan Huntingdon, Sioux Center, IA (US); Eric Martin Krug, Sioux Center, IA (US); Glenn Todd Colon-Bonet, Sioux Center, IA (US)

( * ) Notice: Subject to any disclaimer, the term of this patent is extended or adjusted under 35 U.S.C. 154(b) by 0 days.

(21) Appl. No.: 19/209,445

(22) Filed: May 15, 2025

(51) Int. Cl.
| | |
|---|---|
| *C12N 5/00* | (2006.01) |
| *A61B 17/43* | (2006.01) |
| *A61B 17/435* | (2006.01) |

(52) U.S. Cl.
CPC .............. *C12N 5/562* (2025.01); *A61B 17/43* (2013.01); *A61B 17/435* (2013.01); *C12N 5/544* (2025.01)

(58) Field of Classification Search
CPC ......... A61J 1/165; C12N 5/562; C12N 5/544; F25B 21/04
See application file for complete search history.

(56) References Cited

U.S. PATENT DOCUMENTS

| | | | |
|---|---|---|---|
| 8,420,383 | B2 | 4/2013 | Fanning et al. |
| 8,646,282 | B2 | 2/2014 | Ilercil et al. |
| 8,677,767 | B2 | 3/2014 | Ilercil et al. |
| 9,115,919 | B2 | 8/2015 | Ilercil |
| 9,134,055 | B2 | 9/2015 | Ilercil |

| | | | |
|---|---|---|---|
| 9,151,523 | B2 | 10/2015 | Ilercil |
| 9,470,440 | B2 | 10/2016 | Ilercil |
| 9,599,376 | B2 | 3/2017 | Ilercil |
| 9,791,185 | B2 | 10/2017 | Ilercil |
| 9,829,221 | B2 | 11/2017 | Ilercil |
| 9,874,377 | B1 | 1/2018 | Ilercil |
| 10,119,733 | B1 | 11/2018 | Ilercil |
| 10,156,388 | B2 | 12/2018 | Ilercil |
| 10,161,657 | B2 | 12/2018 | Ilercil |
| 10,342,737 | B1 | 7/2019 | Shanmugavelayudam et al. |
| 10,458,684 | B1 | 10/2019 | Ilercil |

(Continued)

FOREIGN PATENT DOCUMENTS

| | | |
|---|---|---|
| WO | WO2022061211 A1 | 3/2022 |
| WO | WO2023073334 A1 | 5/2023 |

(Continued)

*Primary Examiner* — Jonathan M Hurst
(74) *Attorney, Agent, or Firm* — Gene J. Yao; Barnes & Thornburg LLP

(57) ABSTRACT

A portable incubation system comprising a container and a temperature management system disposed within the container. The container comprises a housing forming an outer wall of the container, an inner chamber assembly disposed within the housing, and a lid coupled to the housing and arranged to seal the inner chamber assembly when closed. The temperature management system comprises a heat sink in thermal communication with an ambient environment of the portable incubation system, a thermoelectric cooler coupled to the inner chamber assembly, and a water-based heat pipe comprises a first end coupled to the heat sink and a second end coupled to the thermoelectric cooler. The system comprises a control system configured to direct the temperature management system to regulate a temperature of the inner chamber assembly and power the portable incubation system.

3 Claims, 31 Drawing Sheets

(56)         References Cited

U.S. PATENT DOCUMENTS

| | | | |
|---|---|---|---|
| 10,495,357 | B2 | 12/2019 | Ilercil |
| 10,844,342 | B2 | 11/2020 | Ramsing et al. |
| 10,852,047 | B2 | 12/2020 | Alexander et al. |
| 10,871,313 | B2 | 12/2020 | Ilercil |
| 10,941,972 | B2 | 3/2021 | Alexander et al. |
| 10,951,047 | B2 | 3/2021 | Neeld |
| 10,982,883 | B1 | 4/2021 | Ilercil |
| 10,982,884 | B2 | 4/2021 | Ilercil |
| 11,293,004 | B2 | 4/2022 | Murali |
| 11,408,650 | B2 | 8/2022 | Ilercil |
| 11,592,218 | B2 | 2/2023 | Ilercil |
| 11,656,007 | B2 | 5/2023 | Ilercil |
| 11,815,306 | B2 | 11/2023 | Siddiqui et al. |
| 11,827,075 | B1 * | 11/2023 | Sieber ................. F28D 15/0275 |
| 11,982,490 | B1 | 5/2024 | McLean et al. |
| 2005/0145273 | A1 * | 7/2005 | Atwood ................. C12Q 1/686 |
| | | | 374/112 |

| | | | |
|---|---|---|---|
| 2018/0100682 | A1 | 4/2018 | Nilsen et al. |
| 2018/0327165 | A1 | 11/2018 | Lee, Sr. et al. |
| 2020/0085036 | A1 | 3/2020 | Creasey et al. |
| 2021/0199353 | A1 * | 7/2021 | Edwards ................. F25B 21/04 |
| 2022/0099541 | A1 | 3/2022 | Croquette et al. |
| 2023/0194132 | A1 | 6/2023 | Ilercil |
| 2023/0265495 | A1 | 8/2023 | DeJohn et al. |
| 2023/0272949 | A1 | 8/2023 | Ilercil |
| 2023/0303959 | A1 | 9/2023 | Blanchard |
| 2024/0068697 | A1 * | 2/2024 | Yadav ...................... F25B 5/02 |
| 2024/0068713 | A1 | 2/2024 | Dupuy |
| 2024/0125522 | A1 | 4/2024 | Sieber et al. |

FOREIGN PATENT DOCUMENTS

| | | | | |
|---|---|---|---|---|
| WO | WO-2024038893 | A1 * | 2/2024 | ........... C12M 45/22 |
| WO | WO2024057324 | A1 | 3/2024 | |

* cited by examiner

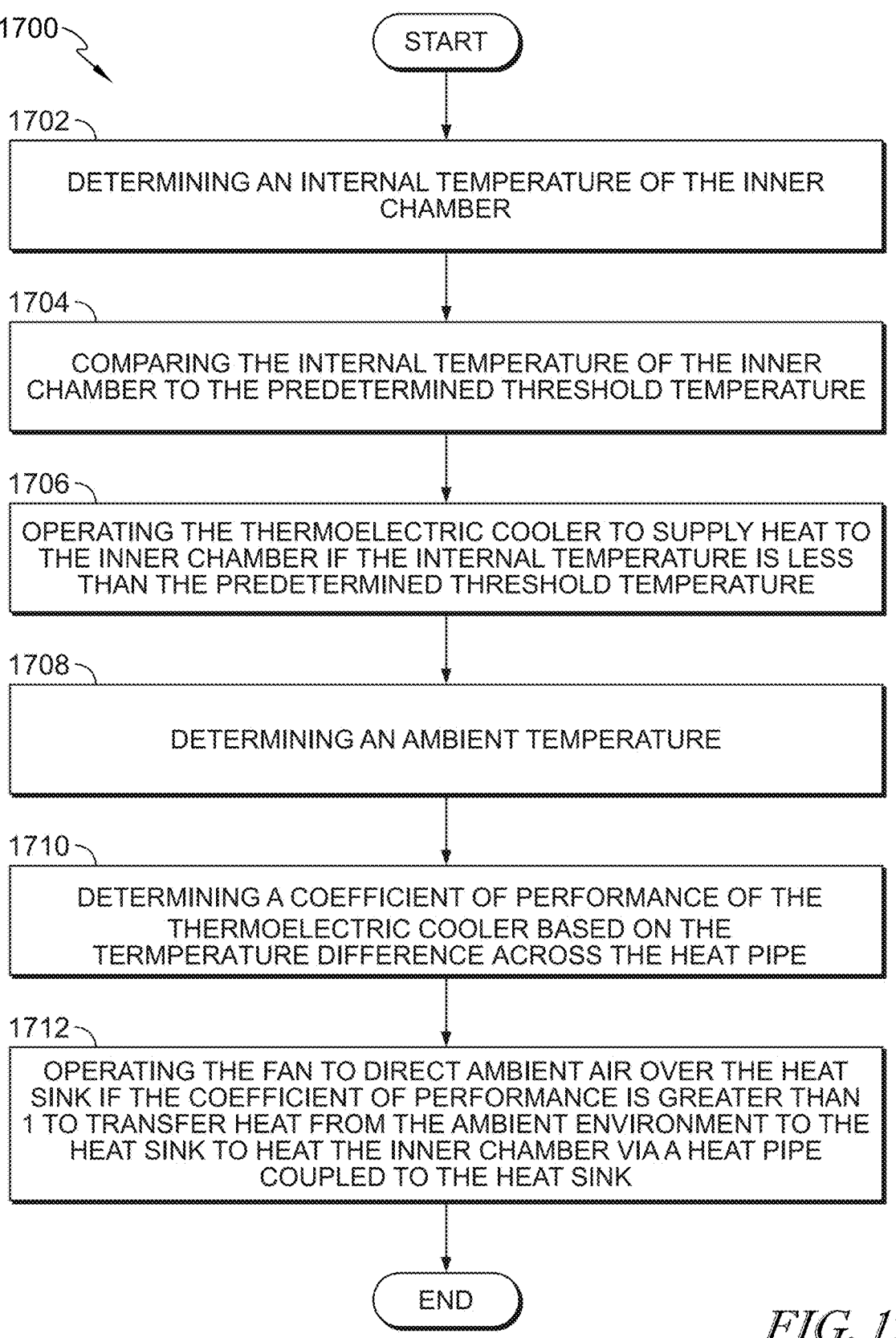

1700

START

1702
DETERMINING AN INTERNAL TEMPERATURE OF THE INNER CHAMBER

1704
COMPARING THE INTERNAL TEMPERATURE OF THE INNER CHAMBER TO THE PREDETERMINED THRESHOLD TEMPERATURE

1706
OPERATING THE THERMOELECTRIC COOLER TO SUPPLY HEAT TO THE INNER CHAMBER IF THE INTERNAL TEMPERATURE IS LESS THAN THE PREDETERMINED THRESHOLD TEMPERATURE

1708
DETERMINING AN AMBIENT TEMPERATURE

1710
DETERMINING A COEFFICIENT OF PERFORMANCE OF THE THERMOELECTRIC COOLER BASED ON THE TERMPERATURE DIFFERENCE ACROSS THE HEAT PIPE

1712
OPERATING THE FAN TO DIRECT AMBIENT AIR OVER THE HEAT SINK IF THE COEFFICIENT OF PERFORMANCE IS GREATER THAN 1 TO TRANSFER HEAT FROM THE AMBIENT ENVIRONMENT TO THE HEAT SINK TO HEAT THE INNER CHAMBER VIA A HEAT PIPE COUPLED TO THE HEAT SINK

END

FIG. 17A

HEAT PIPE 80 FREEZES
INSULATES TEC 94 FROM
AMBIENT ENVIRONMENT

HEAT TRANSFERED INTO INNER
CHAMBER 54 BY TEC 94

HEATING
(COP <1)

94

AMBIENT          TEC          CONTROL

54

BATTERY

102

HEAT GENERATED THROUGH
POWER CONSUMPTION OF THE
TEC 94

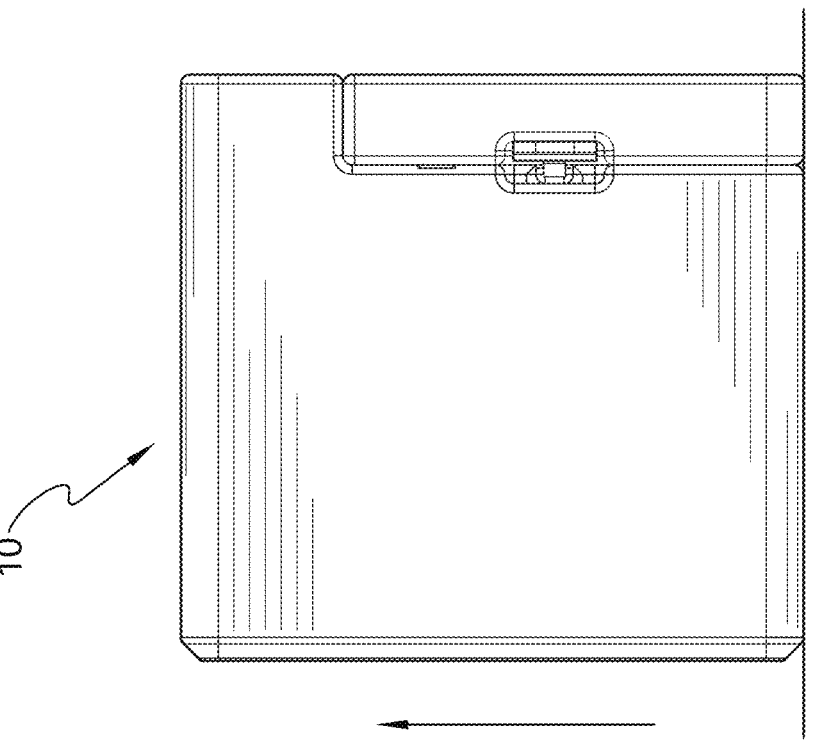
*FIG. 20B*
*FIG. 20A*

PORTABLE INCUBATION SYSTEM

FIELD OF THE INVENTION

The present invention relates generally to medical incubation and, more particularly, to portable incubation systems. Specifically, the present invention relates to a battery-powered portable incubation system for maintaining biological samples at controlled temperatures.

BACKGROUND OF THE INVENTION

Portable incubation systems are essential tools in various fields, including medical diagnostics, scientific research, and biological sample preservation. These systems enable the transport and maintenance of temperature-sensitive materials outside of traditional laboratory settings. Current incubator solutions face significant challenges in maintaining efficient operation across wide temperature ranges, particularly in cold environments. Existing approaches either rely solely on resistive heating, which limits functionality to only heating applications, or employ multiple stacked thermoelectric coolers (TECs), resulting in inefficient operation and added system complexity.

A primary challenge with TEC-based systems is their reduced efficiency at large temperature differentials. As the temperature difference between the hot and cold sides of the thermoelectric cooler increases—particularly in relatively cold ambient conditions—the coefficient of performance (COP) of the TEC declines. When the COP falls below 1 the system consumes more energy to transfer heat than the amount of heat it actually moves. Accordingly, such systems may result in net heat loss to the environment in colder temperatures. Current solutions do not address this decrease in inefficiency of the TEC and potential net heat loss to the ambient environment.

Additionally, existing portable systems often lack robust temperature control mechanisms that can adapt to changing external conditions. This limitation is particularly problematic for sensitive biological samples that require narrow temperature ranges for viability. While some existing systems employ passive thermal control approaches such as phase-change materials or simple insulation, these solutions lack the adaptability needed for operation across widely varying ambient temperatures and cannot efficiently respond to the changing performance characteristics of active cooling components like TECs.

Furthermore, traditional portable incubators typically rely on external power sources or have limited battery life, restricting their utility in field conditions or during extended transport. Those that offer battery operation often struggle to maintain precise temperature control over extended periods, particularly when ambient temperatures fluctuate significantly.

Accordingly, there remains a need in the art for portable incubation systems that can efficiently maintain precise temperatures across varying ambient conditions at relatively large temperature differentials, operate independently on battery power for extended periods, and incorporate robust thermal management strategies that overcome the inherent efficiency limitations of current technologies.

SUMMARY OF THE INVENTION

In one aspect, the present invention provides a portable incubation system for maintaining controlled temperatures across a wide range of ambient conditions.

In some embodiments, the portable incubation system comprises a container, a temperature management system, and a controller.

In some embodiments, the container includes a housing forming an outer wall of the container, an inner chamber assembly disposed within the housing, and a lid coupled to the housing and arranged to seal the inner chamber assembly when closed;

In some embodiments, the temperature management system is disposed within the housing and comprises a heat sink assembly in thermal communication with an ambient environment of the portable incubation system, a thermoelectric cooler assembly coupled to the inner chamber assembly, and a water-based heat pipe extending between the heat sink assembly and a second end coupled to the thermoelectric cooler assembly.

In some embodiments, the control system includes a plurality of temperature sensors disposed in the portable incubation system, the controller is configured to direct the temperature management system to regulate a temperature of the inner chamber assembly based on an ambient temperature.

In some embodiments, the portable incubation system comprises: (a) a container that includes a housing forming an outer wall of the container, an inner chamber assembly disposed within the housing, and a lid coupled to the housing and arranged to seal the inner chamber assembly when closed; (b) a temperature management system disposed within the housing that includes a heat sink assembly in thermal communication with an ambient environment of the portable incubation system, a thermoelectric cooler assembly coupled to the inner chamber assembly, and a water-based heat pipe extending between the heat sink assembly and the thermoelectric cooler assembly; and (c) a controller configured to direct the temperature management system to regulate a temperature of the inner chamber assembly based on the ambient temperature. In some embodiments, the water-based heat pipe is configured to transfer heat through vapor exchange. When a temperature of the ambient environment is greater than 20° C., the water-based heat pipe may be configured to transfer heat between the heat sink assembly and the thermoelectric cooler assembly. When a temperature of the ambient environment is less than 20° C., the water-based heat pipe may be configured to reduce heat transfer between the heat sink assembly and the thermoelectric cooler assembly by providing thermal resistance. In certain such embodiments, (a) when the temperature of the ambient environment is greater than 20° C., the water-based heat pipe is configured to transfer heat between the heat sink assembly and the thermoelectric cooler assembly; and (b) when the temperature of the ambient environment is less than 20° C., the water-based heat pipe is configured to reduce heat transfer between the heat sink assembly and the thermoelectric cooler assembly by providing thermal resistance.

In some embodiments, the inner chamber assembly comprises a plurality of side vacuum insulated panels disposed between an inner wall and the housing. In some embodiments, the inner chamber assembly comprises a bottom vacuum insulated panel arranged between a base and the housing. In some embodiments, the inner chamber assembly comprises: (a) a plurality of side vacuum insulated panels disposed between an inner wall of the inner chamber assembly and the housing; and (b) a bottom vacuum insulated panel arranged between a base and the housing. In some embodiments, the portable incubation system comprises a control system comprising the controller. In some embodiments, the control system includes a plurality of temperature sensors disposed in the portable incubation system. In certain such embodiments, the portable incubation system comprises: (a) a control system comprising the controller; and (b) a plurality of temperature sensors disposed in the portable incubation system.

In some embodiments, the inner chamber assembly comprises an inner chamber and at least one inner block arranged to fit within the inner chamber. The at least one inner block may be shaped to form a plurality of openings. Each of the plurality of openings may be configured to hold a biological sample. In certain such embodiments, the inner chamber assembly comprises an inner chamber and at least one inner block arranged to fit within the inner chamber, wherein the at least one inner block is shaped to form a plurality of openings, each of which is configured to hold a biological sample. In some embodiments, the biological sample comprises embryos, oocytes, and/or gametes.

In some embodiments, at least one of the plurality of temperature sensors is disposed in the inner chamber assembly to detect an internal temperature of the inner chamber assembly. In some embodiments, at least one of the plurality of temperature sensors disposed in the inner chamber is coupled to a biasing mechanism. The biasing mechanism may be configured to bias the temperature sensor towards the at least one inner block to contact an outer surface of the inner block. In certain such embodiments, the at least one temperature sensor disposed in the inner chamber assembly is coupled to a biasing mechanism configured to bias the temperature sensor toward the at least one inner block such that the sensor contacts an outer surface of the inner block. In some embodiments, the at least one inner block comprises a first inner block and a second inner block. The first inner block and the second inner block may be configured to stack vertically within the inner chamber. In some embodiments, the control system comprises the controller and a plurality of temperature sensors wherein one of the temperature sensors is a first temperature sensor disposed in the inner chamber assembly to detect a temperature of the first inner block. In some embodiments, the plurality of temperature sensors further comprises a second temperature sensor disposed in the inner chamber assembly. The second temperature sensor may be spaced apart from the first temperature sensor to detect a temperature of the second inner block. In certain such embodiments, the at least one inner block comprises a first inner block and a second inner block that are configured to stack vertically within the inner chamber, and the at least one of the plurality of temperature sensors comprises a first temperature sensor disposed in the inner chamber assembly to detect a temperature of the first inner block and a second temperature sensor disposed in the inner chamber assembly and spaced apart from the first temperature sensor to detect a temperature of the second inner block. In some embodiments, the first temperature sensor is coupled to a first biasing mechanism configured to bias the first temperature sensor into contact with an outer surface of the first inner block. In some embodiments, the second temperature sensor is coupled to a second biasing mechanism configured to bias the second temperature sensor into contact with an outer surface of the second inner block.

In some embodiments, the inner chamber assembly is configured to maintain a biological sample at a controlled temperature within a specific temperature range for preserving viability of the biological samples during transport of the portable incubation system. In certain such embodiments, the biological sample comprises embryos, oocytes, and/or gametes.

In some embodiments, at least one of the plurality of temperature sensors is disposed in the inner chamber assembly to detect an internal temperature of the inner chamber assembly. In some embodiments, at least one of the plurality of temperature sensors is disposed on the housing to detect a temperature of the ambient environment. In some embodiments, the controller is configured to regulate the internal temperature of the inner chamber assembly based on temperature feedback from the plurality of temperature sensors. In certain such embodiments, the portable incubation system comprises at least one temperature sensor disposed in the inner chamber assembly to detect an internal temperature of the inner chamber assembly, and at least one temperature sensor disposed on the housing to detect an ambient temperature, wherein the controller is configured to regulate the internal temperature of the inner chamber assembly based on temperature feedback from the plurality of temperature sensors.

In some embodiments, the controller is operable to direct the temperature management system to cool the inner chamber assembly when the internal temperature of the inner chamber assembly is above a predetermined threshold temperature. In some embodiments, the control system is operable to direct the temperature management system to heat the inner chamber assembly when the internal temperature of the inner chamber assembly is below the predetermined threshold temperature. In certain such embodiments, the controller of the portable incubation system is operable to: (a) direct the temperature management system to either cool the inner chamber assembly when the internal temperature exceeds a predetermined threshold temperature; or (b) heat the inner chamber assembly when the internal temperature falls below the predetermined threshold temperature.

In some embodiments, the portable incubation system comprises a control system comprising the controller and a power source operable to power the portable incubation system.

In some embodiments, the power source is a battery. In some embodiments, the battery is configured to power the portable incubation system to maintain biological samples at a controlled temperature for at least four hours during transport. In certain such embodiments, the control system is configured to monitor power consumption and adjust operational parameters across different operational modes to extend the operational time of the power source.

In some embodiments, the temperature management system comprises a heater coupled to a bottom of the inner chamber assembly. The control system may be operable to direct the temperature management system to heat the inner chamber assembly with the heater upon start up of the portable incubation system.

In some embodiments, the controller is configured to determine a coefficient of performance (COP) of the thermoelectric cooler assembly based on a temperature differential between the inner chamber assembly and the ambient environment. In some embodiments, the controller is configured to operate the temperature management system in a first heating mode when the COP is greater than 1. The first heating mode may utilize both the thermoelectric cooler assembly and ambient heat transfer via the water-based heat pipe. In some embodiments, the controller is configured to operate the temperature management system in a second heating mode when the COP is less than 1. The second heating mode may utilize the water-based heat pipe as thermal insulation between the thermoelectric cooler assembly and the ambient environment. In certain such embodiments, the controller is configured to determine a coefficient of performance (COP) of the thermoelectric cooler assembly based on a temperature differential between the inner chamber assembly and the ambient environment and the controller is further configured to: (a) operate the temperature management system in a first heating mode, utilizing both the thermoelectric cooler assembly and ambient heat transfer via the water-based heat pipe, when the COP is greater than 1; and (b) operate the temperature management system in a second heating mode, utilizing the water-based heat pipe as thermal insulation between the thermoelectric cooler assembly and the ambient environment, when the COP is less than 1.

In some embodiments, the control system is configured to monitor power consumption and adjust operational parameters during different operational modes to extend operational time of the power source.

In some embodiments, the controller is configured to seamlessly transition between a cooling mode, a first heating mode, and a second heating mode based on continuous sensor feedback. In certain such embodiments, the transition points between modes is determined by both an internal temperature of the inner chamber assembly relative to a predetermined threshold temperature and the ambient temperature relative to a coefficient of performance transition point.

In some embodiments, the temperature management system is configured to respond to ambient temperature transitions around 20° C. by automatically adjusting thermal resistance properties of the water-based heat pipe.

In some embodiments, the water-based heat pipe automatically transitions between efficient heat transfer and increased thermal resistance at approximately 20° C., which corresponds to a transition point where a coefficient of performance of the thermoelectric cooler assembly changes from greater than 1 to less than 1.

In some embodiments, the inner chamber assembly is shaped to form an inner chamber. In some embodiments, the portable incubation system comprises a plurality of vacuum insulated panels disposed between the inner chamber and the housing. In some embodiments, the portable incubation system comprises a lid coupled to the housing and arranged to seal the inner chamber when closed. In certain such embodiments, the inner chamber assembly is shaped to form an inner chamber, and the portable incubation system further comprises a plurality of vacuum insulated panels disposed between the inner chamber and the housing, and a lid coupled to the housing and arranged to seal the inner chamber when closed.

In some embodiments, the container comprises a housing forming an outer wall of the container. The inner chamber assembly may be disposed within the housing and may be shaped to form an inner chamber.

In some embodiments, the thermoelectric cooler assembly comprises a thermoelectric cooler. The thermoelectric cooler may be coupled to the inner chamber and disposed between the base of the inner chamber and at least one of the plurality of vacuum insulated panels. In certain such embodiments, the thermoelectric cooler assembly comprises a thermoelectric cooler coupled to the inner chamber and disposed between the base of the inner chamber and at least one of the plurality of vacuum insulated panels.

In some embodiments, the temperature management system may be disposed within the housing and may comprise a heat sink assembly in thermal communication with an ambient environment of the portable incubation system, a fan configured to direct ambient air over the heat sink assembly.

In some embodiments, the water-based heat pipe extends between the heat sink assembly and a second end coupled to the thermoelectric cooler assembly. In some embodiments, the water-based heat pipe includes a first end coupled to the heat sink assembly and a second end coupled to the thermoelectric cooler assembly.

The control system may include a plurality of temperature sensors disposed in the portable incubation system, a controller configured to direct the temperature management system to regulate a temperature of the inner chamber assembly by operating at least one of the fan and/or the thermoelectric cooler assembly, and a power source operable to power the portable incubation system.

In some embodiments, the thermoelectric cooler assembly comprises a thermoelectric cooler. In some embodiments, the temperature management system comprises a fan configured to direct ambient air over the heat sink assembly. The controller may be configured to direct the temperature management system to regulate the temperature of the inner chamber assembly by operating at least one of the fan and/or the thermoelectric cooler. In certain such embodiments, the thermoelectric cooler assembly comprises a thermoelectric cooler, the temperature management system comprises a fan configured to direct ambient air over the heat sink assembly, and the controller is configured to direct the temperature management system to regulate the temperature of the inner chamber assembly by operating at least one of the fan and/or the thermoelectric cooler.

In some embodiments, the water-based heat pipe is configured to transfer heat through vapor exchange. When a temperature of the ambient environment is greater than 20° C., the water-based heat pipe may be configured to transfer heat between the heat sink assembly and the thermoelectric cooler assembly. When a temperature of the ambient environment is less than 20° C., the water-based heat pipe may be configured to reduce heat transfer between the heat sink assembly and the thermoelectric cooler assembly.

In some embodiments, the thermoelectric cooler assembly comprises a thermoelectric cooler. In some embodiments, the inner chamber assembly is configured to define an inner chamber. The inner chamber may have an inner wall and a base coupled to a bottom portion of the inner wall. The inner wall and the base may together enclose the inner chamber. The inner wall and the base may be arranged to form the inner chamber. A first side of the thermoelectric cooler may be coupled to an exterior surface of the base of the inner chamber assembly. The exterior surface may be opposite an interior surface of the base forming the inner chamber. In certain such embodiments, the thermoelectric cooler assembly comprises a thermoelectric cooler, and the inner chamber assembly is configured to define an inner chamber having an inner wall and a base, with the base coupled to a bottom portion of the inner wall such that the inner wall and base together enclose the inner chamber, and wherein a first side of the thermoelectric cooler is coupled to an exterior surface of the base, the exterior surface being opposite an interior surface of the base.

In some embodiments, at least one of the plurality of temperature sensors is disposed in the inner chamber assembly to detect an internal temperature of the inner chamber assembly. In some embodiments, at least one of the plurality of temperature sensors is disposed on the housing to detect a temperature of the ambient environment. The control system may be configured to regulate the internal temperature of the inner chamber assembly based on temperature feedback from the plurality of temperature sensors.

In some embodiments, the controller is configured to determine a coefficient of performance (COP) of the thermoelectric cooler based on a difference in temperature across the water-based heat pipe. In some embodiments, the controller is configured to operate the temperature management system in a first heating mode when the COP is greater than 1. The first heating mode may comprise operating both the thermoelectric cooler assembly and the fan to transfer heat from the ambient environment via the water-based heat pipe. In some embodiments, the controller is configured to operate the temperature management system in a second heating mode when the COP is less than 1. The second heating mode may comprise operating the thermoelectric cooler assembly and not operating the fan. The second heating mode may utilize the reduced heat transfer capability of the water-based heat pipe as thermal insulation. In certain such embodiments, the controller is configured to: (a) determine a coefficient of performance (COP) of the thermoelectric cooler based on a difference in temperature across the water-based heat pipe; (b) operate the temperature management system in a first heating mode when the COP is greater than 1, wherein the first heating mode comprises operating both the thermoelectric cooler and the fan to transfer heat from the ambient environment by way of the water-based heat pipe; and (c) operate the temperature management system in a second heating mode when the COP is less than 1, wherein the second heating mode comprises operating the thermoelectric cooler and not operating the fan, utilizing the reduced heat transfer capability of the water-based heat pipe as thermal insulation.

In some embodiments, the water-based heat pipe automatically transitions between efficient heat transfer and increased thermal resistance at approximately 20° C., which corresponds to a transition point where a coefficient of performance of the thermoelectric cooler assembly changes from greater than 1 to less than 1.

In some embodiments, the temperature management system comprises a pre-heater in thermal communication with the inner chamber assembly. The controller may be configured to activate the pre-heater upon start up of the portable incubation system to heat the inner chamber assembly more efficiently than would be possible using the heat sink assembly, water-based heat pipe, and thermoelectric cooler assembly alone. In certain such embodiments, the temperature management system of the portable incubation system comprises a pre-heater in thermal communication with the inner chamber assembly, and the controller is configured to activate the pre-heater upon startup of the portable incubation system to heat the inner chamber assembly more efficiently than would be possible using only the heat sink assembly, the water-based heat pipe, and the thermoelectric cooler assembly.

In some embodiments, the power source is a battery. The control system may be configured to monitor power consumption and adjust operational parameters during different operational modes to extend operational time of the battery.

In another aspect, the present invention provides a method of regulating an internal temperature of the portable incubation system.

In some embodiments, the method comprises determining the internal temperature of an inner chamber of the inner chamber assembly using a first temperature sensor disposed within the inner chamber. In some embodiments, the method comprises operating, using the controller, a thermoelectric cooler of the thermoelectric cooler assembly to heat the inner chamber when the internal temperature is below a predetermined threshold temperature. The thermoelectric cooler may be coupled to the base of the inner chamber and/or may be disposed between the inner chamber and a vacuum insulated panel of the portable incubation system. In some embodiments, the method comprises determining a coefficient of performance of the thermoelectric cooler. In some embodiments, the method includes operating, using the controller, a fan when the coefficient of performance is above 1 to heat the inner chamber. The inner chamber may be disposed within a housing forming an outer wall of the portable incubation system. The thermoelectric cooler may be coupled to a base of the inner chamber and may be disposed between the inner chamber and a vacuum insulated panel of the portable incubation system. The fan may be disposed within the housing of the portable incubation system and may be arranged to direct ambient air over a heat sink coupled to the inner chamber via a water-based heat pipe to transfer heat from the ambient air to the inner chamber. In certain such embodiments, the method comprises: (a) determining the internal temperature of an inner chamber of the inner chamber assembly using a first temperature sensor disposed within the inner chamber; (b) operating a thermoelectric cooler of the thermoelectric cooler assembly using the controller to heat the inner chamber when the internal temperature is below a predetermined threshold temperature, wherein the thermoelectric cooler is coupled to a base of the inner chamber and disposed between the inner chamber and a vacuum insulated panel of the portable incubation system; (c) determining a coefficient of performance of the thermoelectric cooler; and (d) operating a fan using the controller when the coefficient of performance is above 1, the fan being disposed within the housing of the portable incubation system and arranged to direct ambient air over the heat sink assembly.

In some embodiments, the method further comprises determining an ambient temperature using a second temperature sensor disposed within the housing of the portable incubation system. In some embodiments, the method includes using the determined ambient temperature to calculate the coefficient of performance of the thermoelectric cooler. In certain such embodiments, the method further comprises determining an ambient temperature using a second temperature sensor disposed within the housing of the portable incubation system and using the determined ambient temperature to calculate the coefficient of performance of the thermoelectric cooler.

In some embodiments, the method comprises insulating the inner chamber from the ambient environment with the water-based heat pipe when the coefficient of performance is below 1. In certain such embodiments, the water-based heat pipe transitions from efficiently transferring thermal energy through vapor exchange above 20° C. to providing thermal resistance below 20° C., which corresponds to when the coefficient of performance of the thermoelectric cooler transitions from above 1 to below 1.

In some embodiments, the method comprises monitoring, using the controller, power consumption of the portable incubation system during steady-state operation. In certain such embodiments, during steady-state operation, power is primarily required for the thermoelectric cooler and periodic fan operation.

In some embodiments, the portable incubation system comprises a wireless communication module is operatively in communication with the controller. The wireless communications module may be configured to transmit temperature data and location data to a remote monitoring system. In some embodiments, the portable incubation system comprises a GPS module in communication with the controller.

The GPS module may be configured to provide real-time location data of the portable incubation system during transport. In some embodiments, the control system is configured to define a geofenced route for transport of the portable incubation system, monitor the location of the portable incubation system relative to the geofenced route, and trigger an alert when the portable incubation system deviates from the geofenced route. In certain such embodiments, the portable incubation system comprises at least one of a wireless communication module operatively in communication with the controller and configured to transmit temperature data and location data to a remote monitoring system, or a GPS module operatively in communication with the controller and configured to provide real-time location data of the portable incubation system during transport, wherein the controller is configured to define a geofenced route for transport of the portable incubation system, monitor the system's location relative to the geofenced route, and trigger an alert when the system deviates from the defined route.

In some embodiments, a shipping case is configured to accommodate the portable incubation system in either a vertical orientation or a horizontal orientation. In some embodiments, the shipping case comprises a first set of ventilation openings aligned with a vent of the temperature management system when the portable incubation system is in the vertical orientation. In some embodiments, the shipping case comprises a second set of ventilation openings aligned with the vent when the portable incubation system is in the horizontal orientation. In certain such embodiments, the shipping case is configured to accommodate the portable incubation system in either a vertical or horizontal orientation, and comprises a first set of ventilation openings aligned with a vent of the temperature management system when the system is in the vertical orientation, and a second set of ventilation openings aligned with the vent when the system is in the horizontal orientation.

In some embodiments, the inner chamber assembly comprises a first inner block configured to hold biological sample containers in a vertical orientation when the portable incubation system is operated in a vertical configuration. In some embodiments, the inner chamber assembly comprises a second inner block configured to hold biological sample containers in a horizontal orientation when the portable incubation system is operated in a horizontal configuration. In certain such embodiments, the inner chamber assembly of the portable incubation system comprises: (a) a first inner block configured to hold biological sample containers in a vertical orientation when the system is operated in a vertical configuration; and (b) a second inner block configured to hold biological sample containers in a horizontal orientation when the system is operated in a horizontal configuration.

The systems and methods described herein provide a portable incubation system that overcomes limitations of existing incubation systems by incorporating a passive thermal control mechanism. The system utilizes a water-based heat pipe 80 that functions as a passive thermal valve, automatically increasing thermal resistance during cold operation conditions. This passive control eliminates the need for complex mechanical valves or additional control systems while improving efficiency.

The portable incubation system advantageously utilizes the inherent temperature-dependent properties of water-based heat pipes 80 to create a passive thermal control effect. When ambient temperatures drop below approximately 20° C., which corresponds to when a coefficient of performance (COP) of the TEC drops below 1, the colder temperature affects the water-based heat pipe 80 such that it automatically increases thermal resistance between the TEC and the ambient environment. Alternatively, the COP may shift from greater than 1 to less than 1 at different temperatures than 20° C. For example, the COP shift to below 1 may happen at approximately 0° C. The temperature at which the COP shifts from greater than 1 to less than 1 may depend on the thermal performance of the overall incubation system. The coefficient of performance (COP) of the thermoelectric cooler represents its heating or cooling efficiency. The COP is calculated as the ratio of heat moved to electrical power consumed. When the COP is greater than 1, the TEC moves more heat than the electrical power it consumes; when the COP falls below 1, the TEC consumes more electrical power than the heat it moves, making it less efficient for heat transfer.

At this transition temperature of 20° C., the water-based heat pipe 80 transitions from efficiently transferring thermal energy between two opposing ends of the heat pipe 80 to, instead, acting as an insulator between the ambient environment and the inner chamber 54 of the incubation system 10 due to the working fluid freezing and/or not vaporizing as easily below 20° C. than at higher temperatures.

In one embodiment, the COP of the TEC also transitions to less than 1 at a similar temperature. In other words, at a temperature above 20° C., the TEC has a COP greater than 1, meaning the TEC efficiently provides heating or cooling relative to the power usage of the TEC. When the temperature drops below 20° C., the COP of the TEC falls below 1, meaning the TEC requires larger amounts of power to transfer heat, making the TEC less efficient. This alignment between the heat pipe's 80 performance transition and the TEC's COP transition point significantly improves the system's efficiency in cold conditions, because at the same transition point where the TEC's heating ability becomes less efficient, the heat pipe 80 begins acting as an insulator. The heat pipe's 80 position between the TEC and the cold, ambient environment reduces heat loss from the TEC to the ambient environment, which would otherwise further decrease the TEC's heating efficiency. The control system of the incubation system further directs components of the incubation system to operate according to the ambient temperature and determined COP of the TEC to operate the incubation system more efficiently.

The described system and method enables reliable temperature control through a primarily passive operation, eliminating the need for additional control systems. This results in a simplified, reliable design with few moving parts and reduced maintenance requirements. The passive thermal control mechanism also improves energy efficiency in cold environments, extending battery life in portable applications. Furthermore, the system can be implemented in various portable incubation system embodiments that require temperature control across wide ambient temperature ranges.

The portable incubation system is particularly suited for applications including field medical diagnostics, biological sample transport, scientific research outside laboratory environments, and other situations requiring precise temperature control in varying ambient conditions.

BRIEF DESCRIPTION OF THE DRAWINGS

FIG. 17A is a diagram of a method of a first heating mode of the portable incubation system of FIG. 1.

FIG. 20A is a front view of portable incubation system of FIG. 1 in a second shipping configuration.

FIG. 20B is a section view of the portable incubation system of FIG. 20A, in the second shipping configuration, showing the portable incubation system is oriented horizontally and the heat pipe is oriented vertically in the second shipping configuration.

Figure 1:
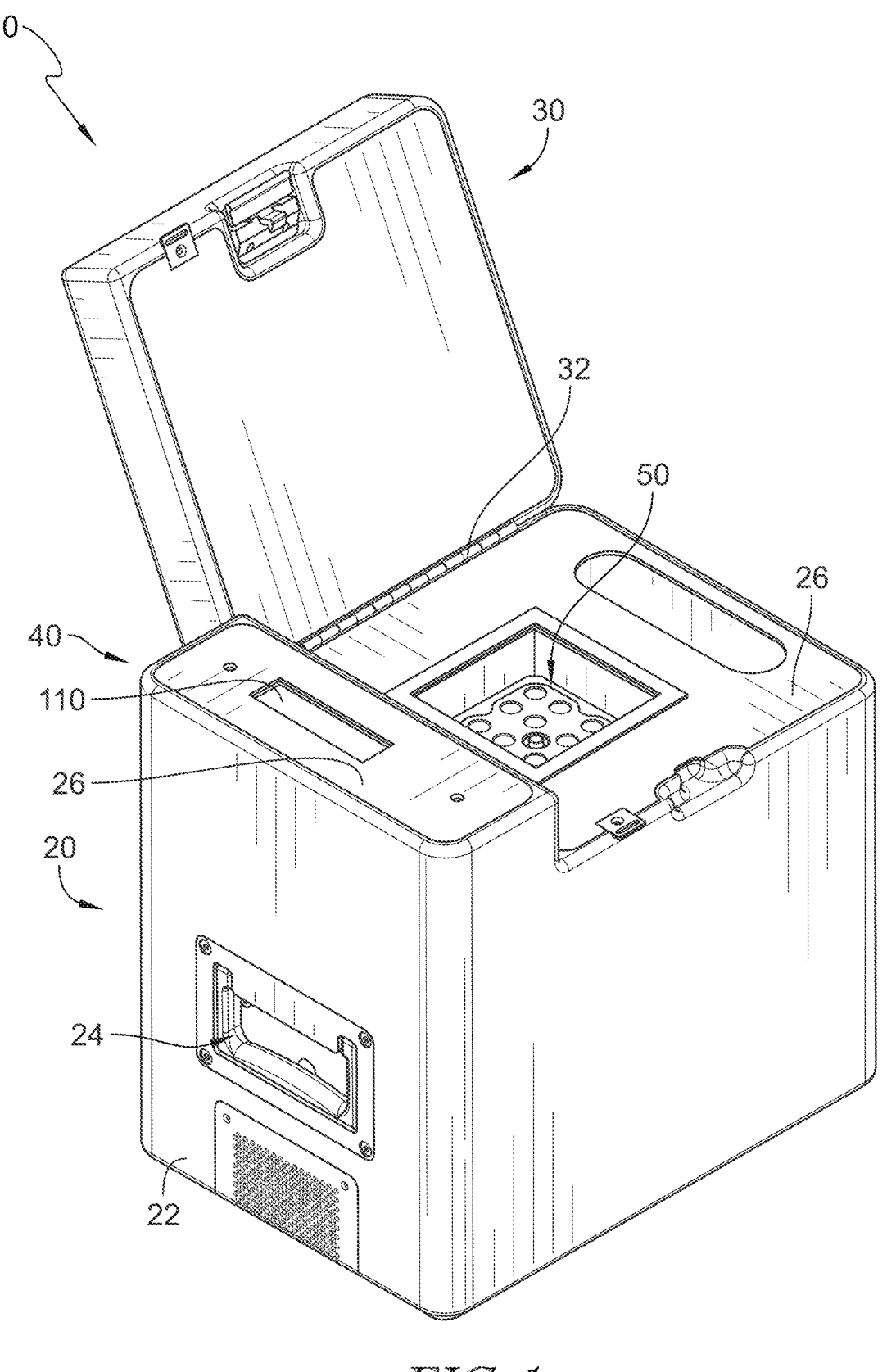
FIG. 1 is a perspective view of a portable incubation system according to an embodiment of the present invention.

DETAILED DESCRIPTION OF THE
INVENTION

The following detailed description is merely exemplary in nature and is not intended to limit the present disclosure, its application, or uses. It is to be understood that the present disclosure is not limited to the particular embodiments described herein and as such can vary. Although various features of the disclosure can be described in the context of a single embodiment, the features can also be provided separately or in any suitable combination. Those of skill in the art will recognize that there are variations and modifications of the present disclosure, which are encompassed within its scope.

Described herein is a portable incubation system. As will be discussed in more detail below, the portable incubation system includes a temperature-controlled chamber. The chamber may be insulated from the ambient environment. A temperature management system regulates the temperature within the chamber. The temperature management system includes a water-based heat pipe that extends between the chamber and the ambient environment.

The use of water as the working fluid in the heat pipe helps minimize heat loss and preserve efficiency during ambient temperature changes. For example, the heat pipe may efficiently transfer heat between the ambient environment and the inner chamber when the ambient temperature is above the freezing point of water. As the ambient temperatures drops, the heat pipe may become less efficient at transferring heat due to freezing of the water within the heat pipe. An aspect of the present system is that as the water in the heat pipe freezes and solidifies, the heat pipe starts to act as an insulator between the cold ambient environment and the inner chamber, minimizing heat loss of the system. This transition from efficiently transferring heat to instead insulating the inner chamber may happen automatically and/or passively, without the need for external intervention or input from an operator. The feature of the heat pipe may result in a simpler, more robust incubation system with less complexity than traditional incubation systems.

In some embodiments, the temperature management system includes a TEC coupled between the chamber and the heat pipe. The TEC may be used to heat and/or cool the chamber. Another aspect of the present system is that the temperature at which the heat pipe begins to insulate the chamber may advantageously align with the temperature at which the thermoelectric cooler becomes less efficient. The insulating properties of the water-based heat pipe at colder temperatures helps minimize heat loss from the TEC to the ambient environment even as the efficiency of the TEC may be decreasing. These features further allow the incubation system to adjust operation of the temperature management system based on the ambient temperature to preserve efficiency of the incubation system. For example, the system may operate in different heating and/or cooling modes to minimize heat loss to the environment and more efficiently heat and/or cool the chamber.

The arrangement of the heat pipe within the incubation system also enables the chamber to be fully insulated when the heat pipe is acting as an insulator, eliminating and/or minimizing any exposure points to the cold, ambient environment. In some embodiments, a majority of the chamber may be surrounded by insulating materials, such as vacuum insulated panels, along the top, bottom, and sides of the chamber. Use of a single heat pipe may minimize possible exposure points. In other words, there may only be a single gap in the insulting materials where the heat pipe extends between the chamber and the ambient environment. During warmer temperatures, the heat pipe and gap allow heat to transfer between the chamber and the environment. In colder temperatures, when the water within the heat pipe freezes, the heat pipe itself becomes an insulator and plugs the gap in the insulating materials. This further preserves the efficiency of the system by decreasing the amount of heat transfer between the cold ambient environment and the chamber.

It should be understood that throughout the drawings, corresponding reference numerals indicate like or corresponding parts and features. The section headings used herein are for organizational purposes only and are not to be construed as limiting the subject matter described.

Definitions

The following definitions supplement those in the art and are directed to the current application and are not to be imputed to any related or unrelated case. Unless defined otherwise, all technical and scientific terms used herein have the same meaning as commonly understood by one of ordinary skill in the art to which this disclosure pertains.

The term "coefficient of performance," which may also be abbreviated as "COP," means a ratio of heating or cooling provided to work required. In this application, the term COP is used in reference to a heating or cooling element, for example, a thermoelectric cooler. For example, when the COP of a thermoelectric cooler is greater than 1, the thermoelectric cooler is operating very efficiently and is suppling or removing more heat than work that it is consuming.

The term "portable" means easily moved, carried, and/or transported. For example, if a component, such as an incubation system, is portable, the component can easily be moved or transported. The component does not need to be otherwise connected to or fixed to a surface or other immovable object. The component does not need to be connected to a fixed or immovable power source, such as a wall outlet. The component may also be of a size and shape such that it is easily lifted and carried by a person.

The term "vacuum insulated panels," which may also be abbreviated as "VIP," means a panel of insulating material that is surrounded by a sealed enclosure from which air has been evacuated. The absence of air in the vacuum insulated panel decreases the occurrence of heat transfer through conduction and convention within the vacuum insulated panel.

The term "water-based heat pipe" means a heat pipe that uses water within the heat pipe to transfer heat from one end of the pipe to the other through a cycle of evaporation and condensation.

The term "pre-heater" means an electric device or component coupled to the inner chamber 54 other than the heat sink assembly 70, heat pipe 80, and the TEC assembly 90, and which may be used to heat the inner chamber 54 more quickly than the heat sink assembly 70, heat pipe 80, and the TEC assembly 90.

The term "thermoelectric cooler," which may also be abbreviated as "TEC," means a component that provides heating and/or cooling through the consumption of electrical energy through the Peltier effect. The TEC may have a hot side and a cold side.

The term "thermal communication" is used to refer to components that are arranged such that thermal energy or heat may transfer between them. The heat may be transferred between the components, for example, by conduction, convection, radiation, or any other means.

The term "seal" means a component or action that prevents liquids, gases, and/or other materials from passing through the seal or sealed components. A seal may be a device, for example a gasket or other suitable component, that is used to create a fluid-tight closure such that fluids or other materials cannot enter or exit the closure.

The term "status information" means any information and/or relevant indications related to the status or operation of the portable incubation system. Status information may include, for example, information related to the COP of the TEC, the internal and/or ambient temperatures—in particular, the internal temperature in relation to a predetermined threshold or control temperature—the power level, and/or battery status.

The term "thermal resistance" means opposition to heat transfer. For example, if a device or component provides thermal resistance, the device acts as an insulator or slows down or works to block the transfer of heat or thermal energy through the device.

The term "biological sample" means a biological specimen or biospecimen that comprises a biological material such as bodily fluid and/or tissue. Biological samples may include, but are not limited to, cells, tissues, organs, blood, plasma, serum, saliva, urine, cerebrospinal fluid, synovial fluid, lymph, sputum, stool, hair, skin, biopsy samples, microbial cultures, proteins, nucleic acids, and other biological materials of human, animal, plant, or microbial origin. Examples of biological samples that particularly benefit from temperature-controlled storage include embryos, oocytes and/or gametes.

The term "predetermined threshold temperature" in this application refers to the predetermined temperature the inner chamber of the incubation system is set to maintain to keep the biological samples viable. The predetermined threshold temperature may be set based on an input control temperature value a user enters. The predetermined threshold temperature may be determined based on the type of biological sample in the incubation system. A predetermined threshold range may be determined based on the predetermined threshold temperature, creating an upper and lower temperature limit within which the incubation system maintains the inner chamber.

In this application, the use of the singular includes the plural unless specifically stated otherwise. The singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. For example, the phrase "A, B, and/or C" can mean "A individually; B individually; C individually; A and B; B and C; A and C; and A, B, and C."

Use of the term "including" as well as other forms, such as "include," "includes," and "included," is not limiting. The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional possible components, elements, or method steps.

Reference to "some embodiments," "an embodiment," "one embodiment" or "other embodiments" means that a particular feature, structure, or characteristic described in connection with the embodiments is included in at least some embodiments, but not necessarily all embodiments, of the present disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. For example, the amount "about 10" includes 10 and any amounts from 9 to 11. The term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

It is contemplated that any embodiment discussed herein can be implemented with respect to any method or composition of the disclosure, and vice versa. Furthermore, compositions of the present disclosure can be used to achieve methods of the present disclosure.

Detailed Description of Preferred Embodiments

FIG. 1 illustrates an embodiment of a portable incubation system 10 according to the invention. The incubation system 10 includes a container 20, a temperature management system 60, and a controller 106. The portable incubation system 10 may include a control system 100 comprising the controller 106. In this embodiment, the temperature management system 60 and the control system 100 are housed within the container. The container 20 of the incubation system is arranged to contain biological samples. The incubation system operates to maintain an internal temperature of the container 20 at a predetermined threshold temperature.

The temperature management system 60 operates to heat or cool the container to bring an inner chamber 54 of the container to the predetermined threshold temperature and maintain the chamber 54 at that temperature, for example, while the incubation system 10 is used to move or transport the samples. The temperature management system 60 utilizes a heat sink assembly 70 in thermal communication with the ambient environment, a heat pipe 80 extending between the heat sink assembly 70 and a TEC assembly 90, and the TEC assembly 90 coupled to the inner chamber 54 to heat or cool the inner chamber 54. The temperature management system 60 is operated in a cooling mode, a first heating mode, or a second heating mode based on an ambient temperature and the COP of the TEC.

Incubator Design

The container 20 may comprise a housing 40 forming an outer wall of the container 20 and an inner chamber assembly 50. The inner chamber assembly 50 may be disposed within the housing 40. The housing 40 forms an outer wall 22 of the container 20 of the incubation system 10. The housing 40 may comprise, for example, plastic, metal, or another suitable material. The container 20 may comprise a lid 30 coupled to the housing 40. The lid 30 may be arranged to seal an inner chamber 54 of the inner chamber assembly 50 when the lid 30 is closed. The lid 30 may be coupled to the housing 40 via a hinge 32.

In one embodiment, the container 20 includes handles 24 formed in the housing 40 on two opposite sides of the container for ease of carrying. The container also includes face plates 26 coupled to a top side of the housing 40 to protect the internal components of the incubation system 10. At least one of the faceplates 26 is removed in FIGS. 2-4 to show a better view of the inner chamber assembly 50.

The lid 30 may be arranged to pivot between an open position, as shown in FIG. 1, and a closed position. In the closed position, the lid 30 is arranged to close off and seal an opening into the inner chamber assembly 50. The lid 30 may comprise an insulating panel 55, such as a vacuum insulated panel or any other suitable insulating materials.

Figure 19B:
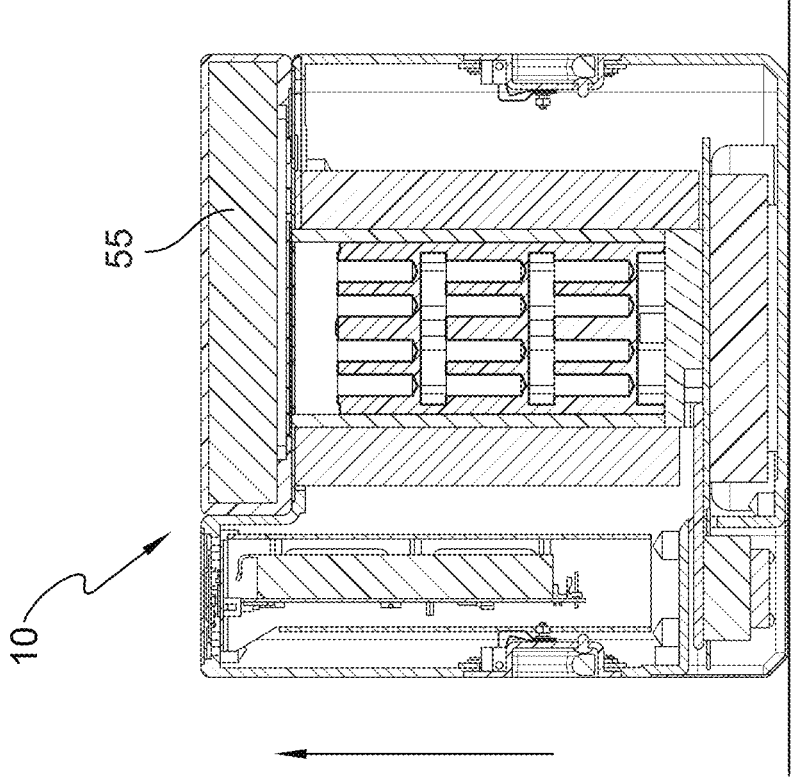
FIG. 19B is a section view of the portable incubation system of FIG. 19A, in the first shipping configuration, showing the portable incubation system is oriented vertically and the heat pipe is oriented horizontally in the first shipping configuration.

The lid 30 is removed in some figures for a better view of the inner chamber 54, but the insulating panel 55 can be seen in FIGS. 19B and 20B.

Inner Chamber Assembly

In some embodiments, the inner chamber assembly 50 comprises a plurality of side vacuum insulated panels 52 disposed between an inner wall 58 of the inner chamber assembly and the housing 40. In some embodiments, the inner chamber assembly 50 comprises a bottom vacuum insulated panel 53 arranged between a base 59 of the inner chamber assembly and the housing 40. The inner chamber assembly 50 may comprise an inner chamber 54 and at least one inner block 56 arranged to fit within the inner chamber 54. The inner chamber assembly 50 may be shaped to form the inner chamber 54.

The inner chamber assembly 50 may be disposed within the housing 40. In one embodiment, the inner chamber assembly 50 includes an inner wall 58 and base 59 disposed at and/or coupled with the bottom of the inner wall 58. The base 59 and inner wall 58 cooperate to enclose the inner chamber 54. In one embodiment, the inner wall 58 comprises four walls arranged in a square to form a rectangular inner chamber 54.

Figures 2, 3:
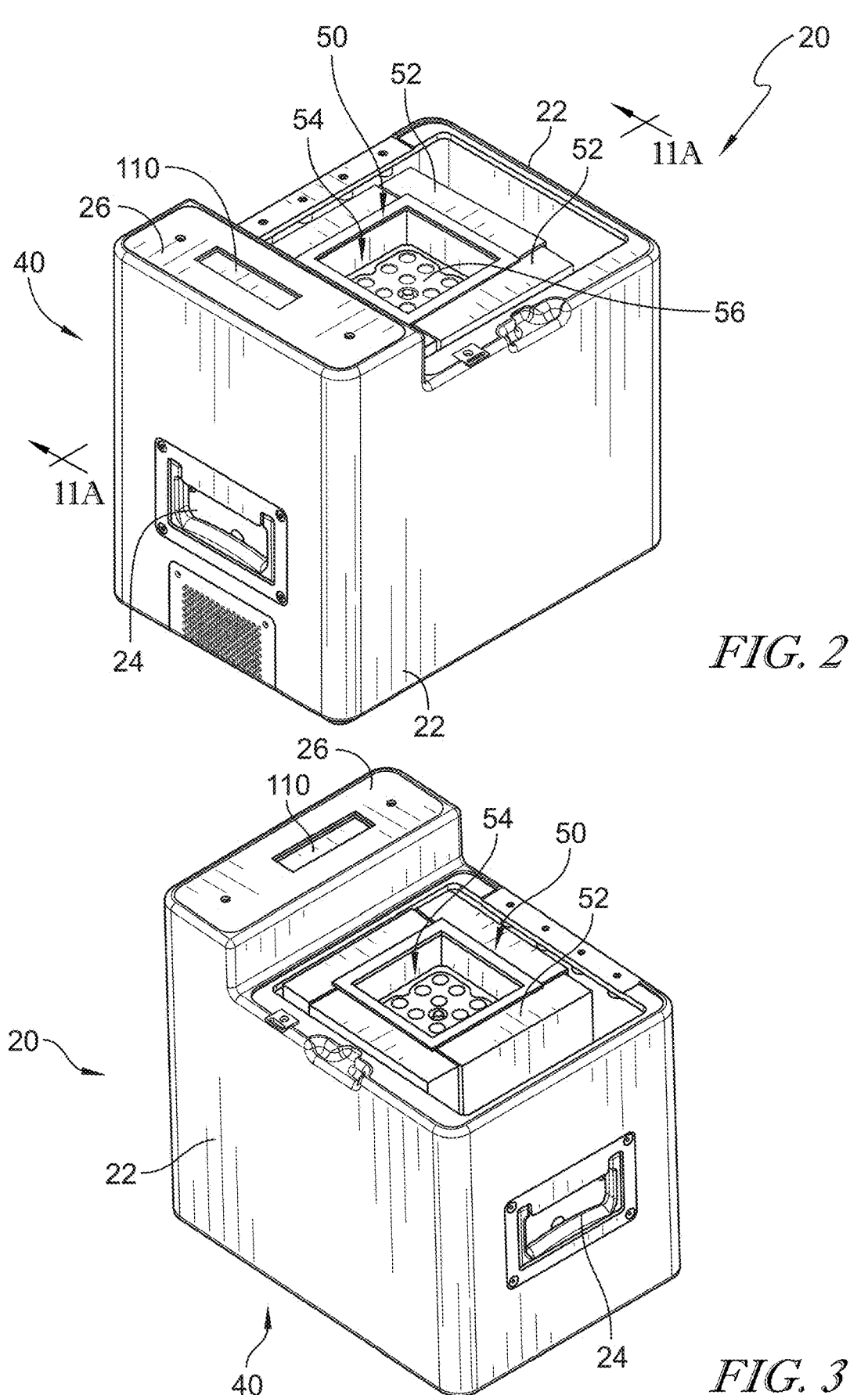
FIG. 2 is a perspective view of the portable incubation system of FIG. 1 with the lid and the upper face plate removed, showing the inner chamber assembly.
FIG. 3 is a rear perspective view of the portable incubation system of FIG. 2.
Figure 4:
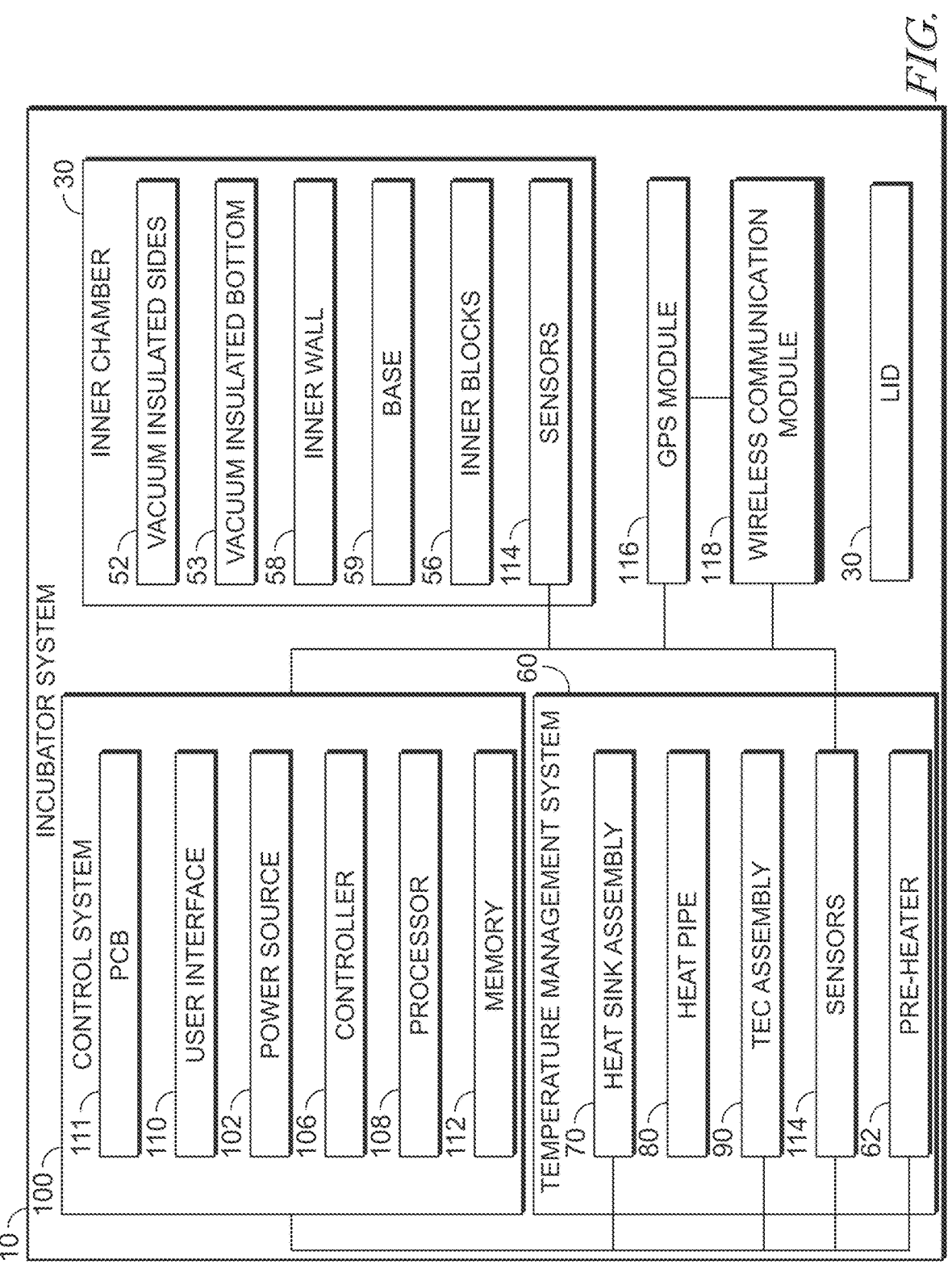
FIG. 4 is a system diagram of the portable incubation system of FIG. 1.
Figure 5:
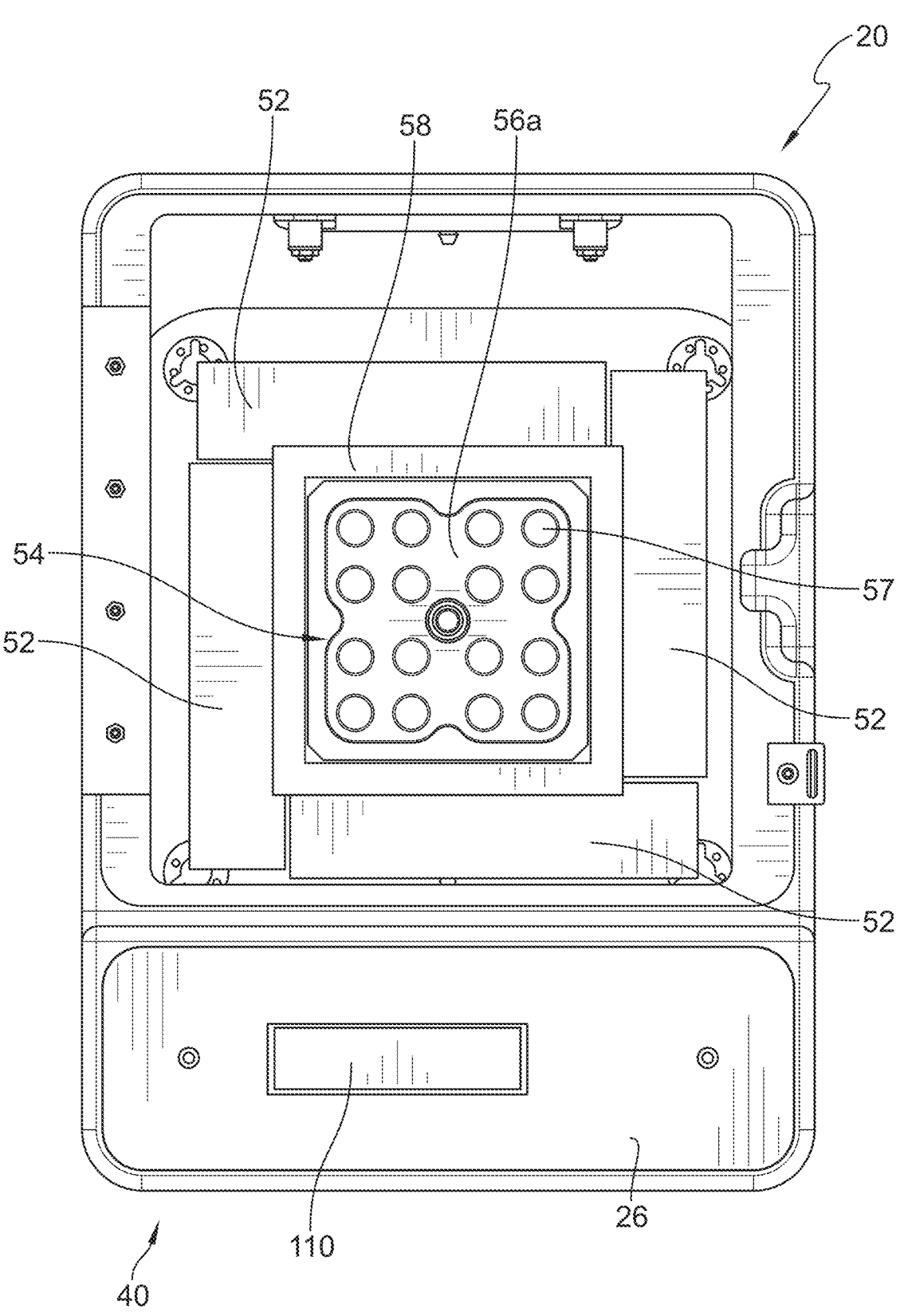
FIG. 5 is a top view of the portable incubation system of FIG. 2.
Figure 6:
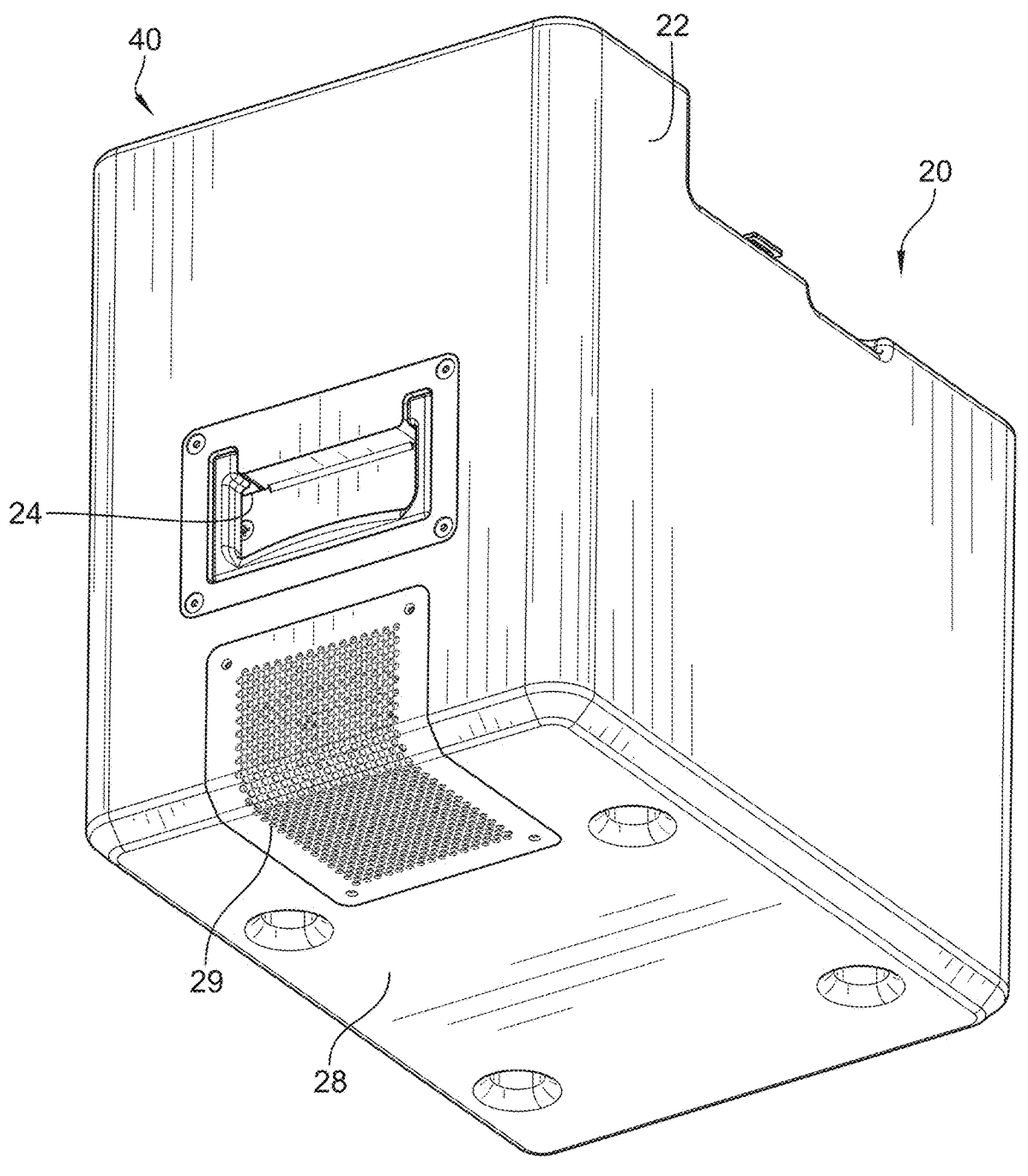
FIG. 6 is a bottom perspective view of the incubator of FIG. 2
Figure 7:
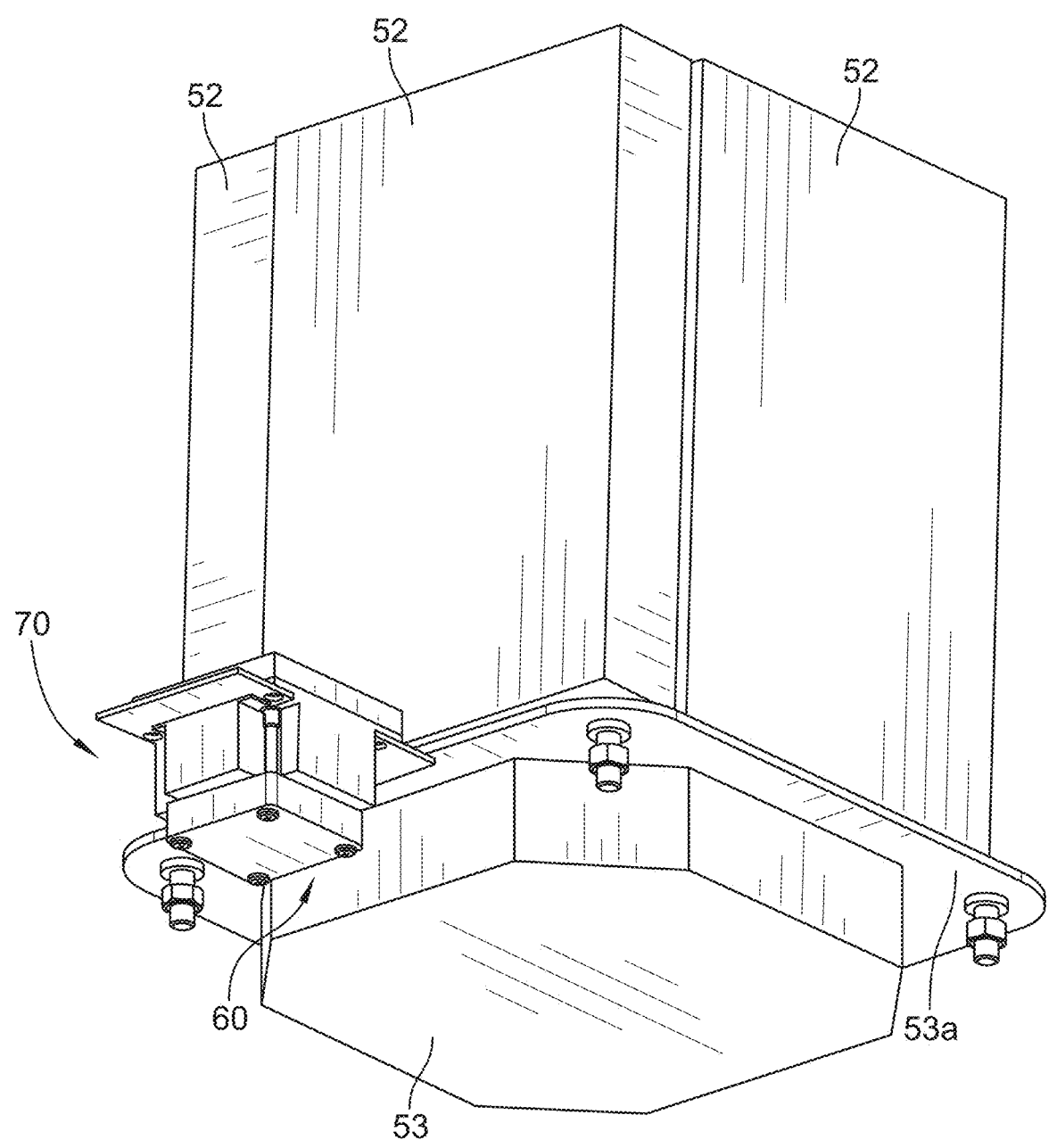
FIG. 7 is a bottom perspective view of the inner chamber assembly and temperature management system of the incubator of FIG. 1.

The inner chamber assembly 50 may include a plurality of vacuum insulated panels 52 to insulate the inner chamber 54. As shown in FIGS. 2-4, the vacuum insulated panels 52 may be disposed between the inner wall 58 and the housing 40. As shown in FIG. 7, a bottom vacuum insulated panel 53 and panel backing plate 53*a* may be disposed between the base 59 of the inner chamber assembly 50 and a bottom 28 of the container 20.

Figure 8A:
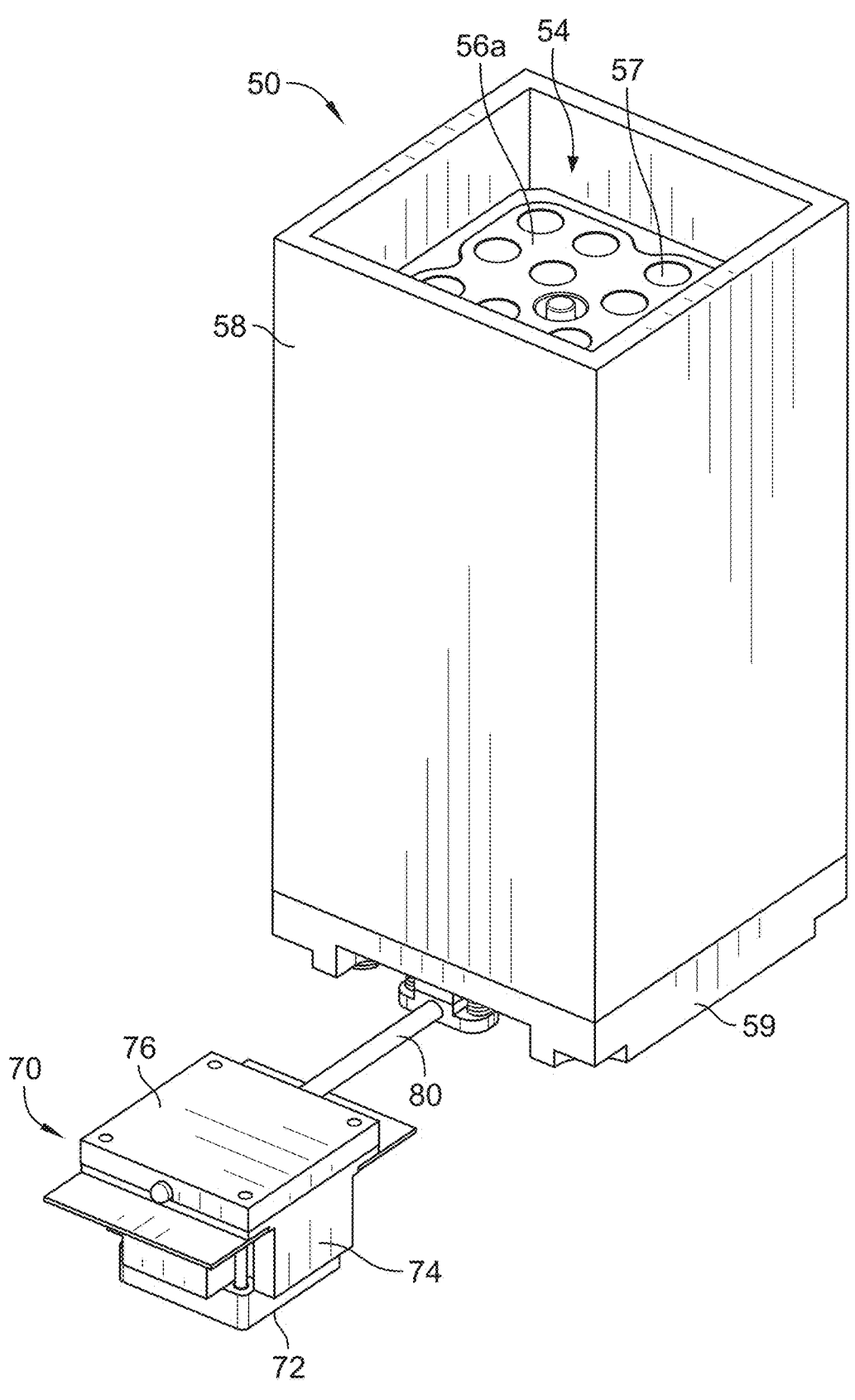
FIG. 8A is a perspective view of the inner chamber assembly, a first inner block embodiment configured to receive vials, and temperature management system of FIG. 7.
Figure 8B:
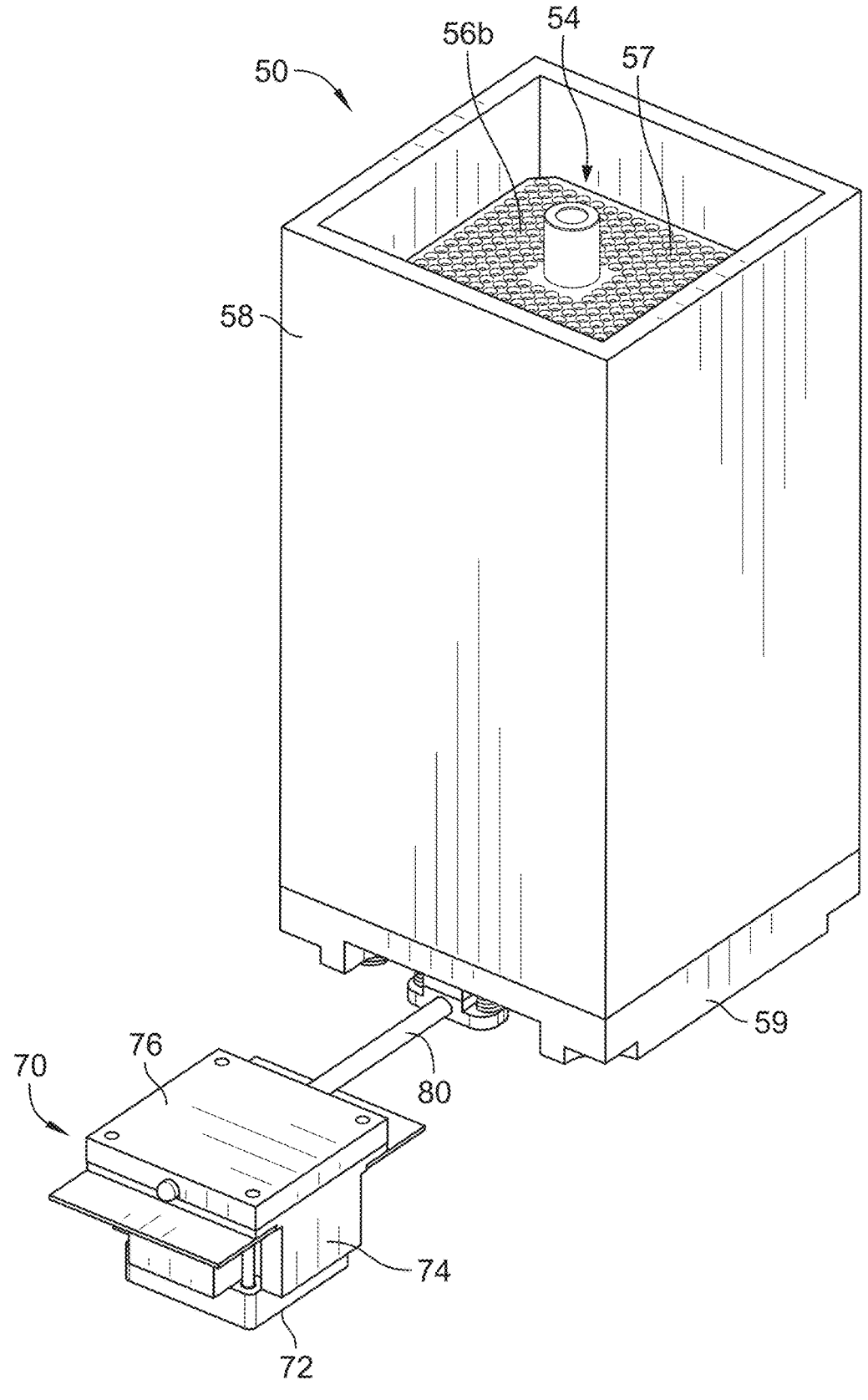
FIG. 8B is a perspective view of the inner chamber assembly, a second inner block embodiment configured to receive straws, and temperature management system of FIG. 7.
Figure 9:
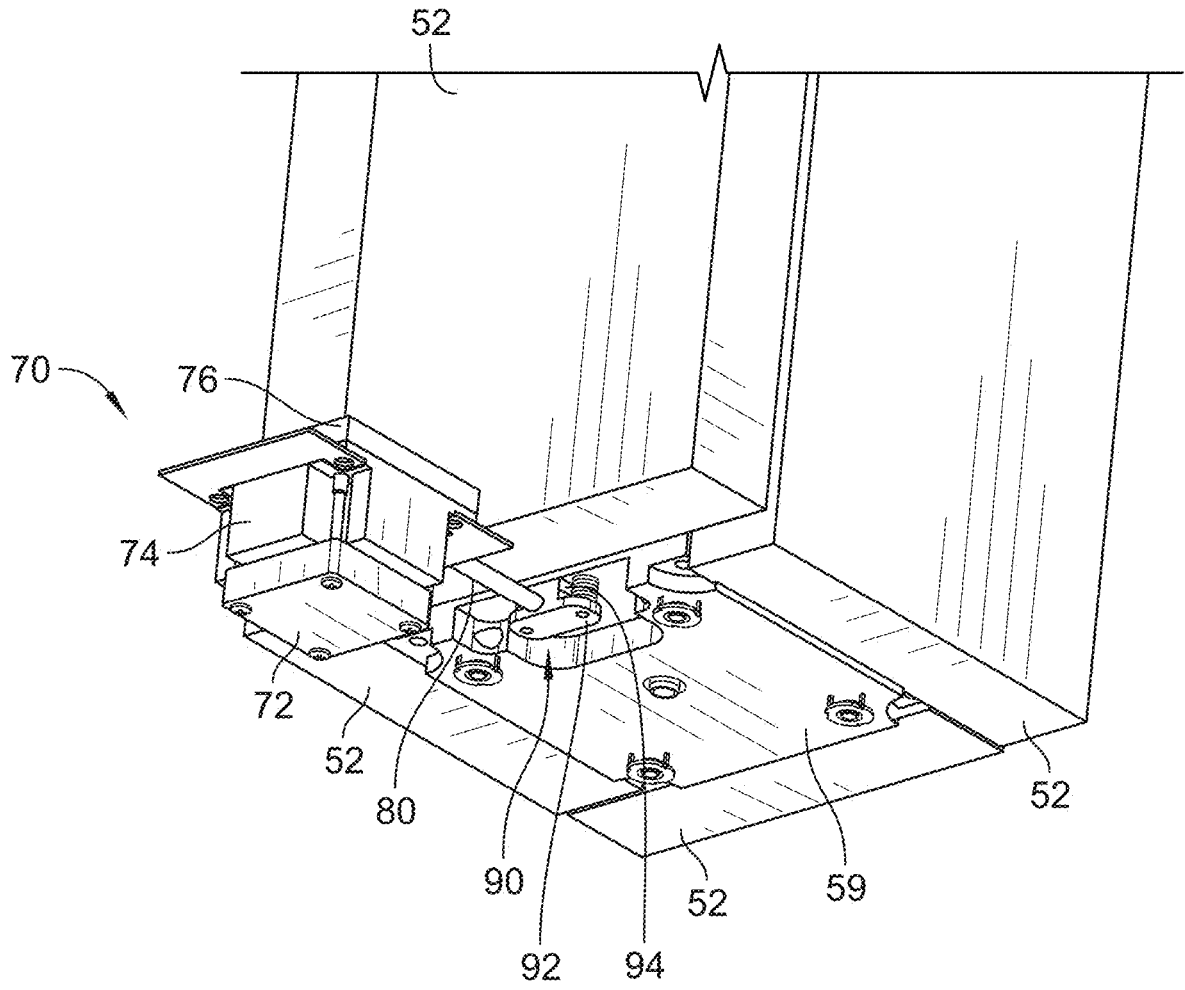
FIG. 9 is a detail view of the temperature management system of FIG. 7 coupled to the base of the inner chamber assembly.
Figure 10:
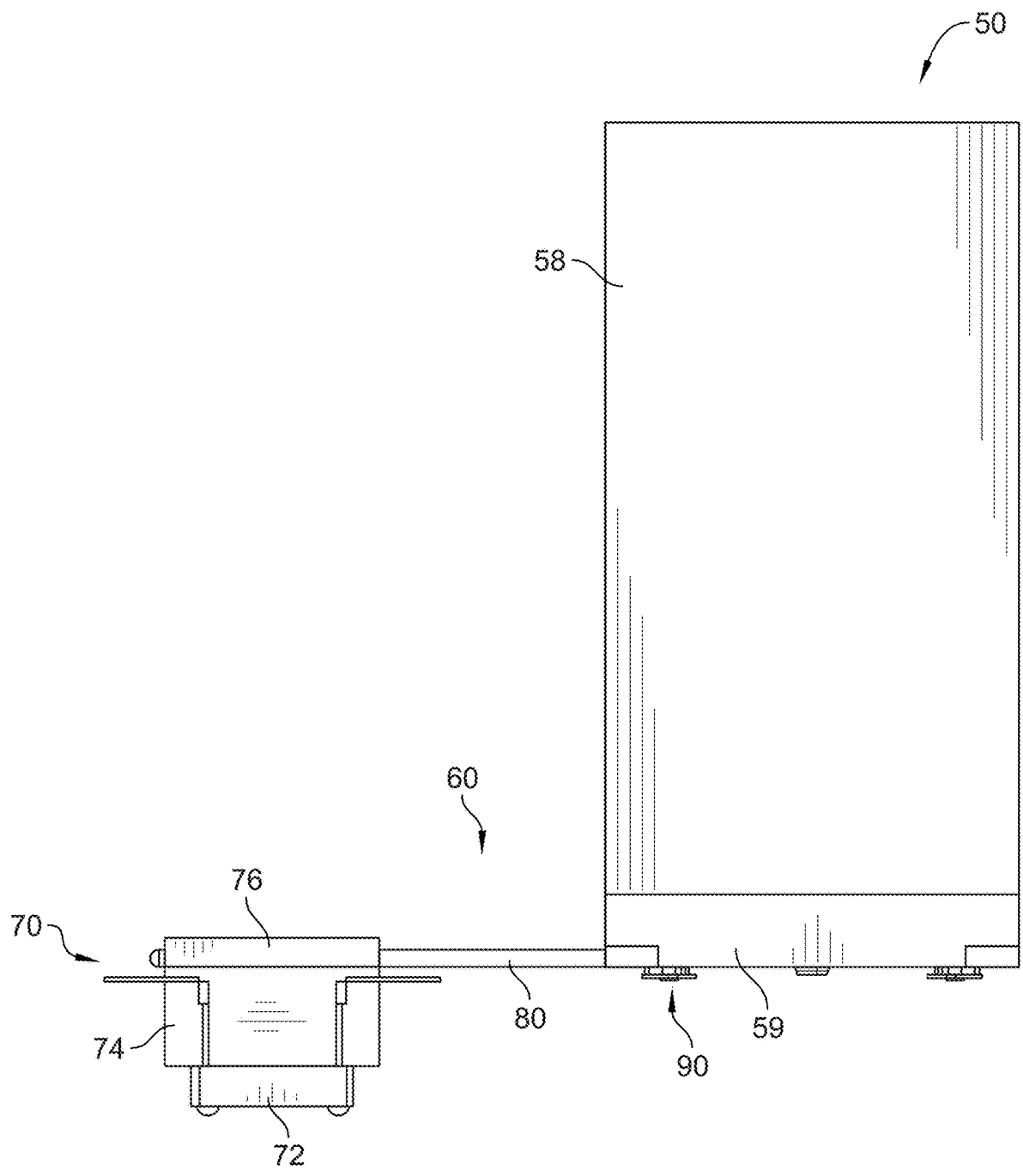
FIG. 10 is a side view of the inner chamber assembly and temperature management system of FIG. 7.
Figure 11A:
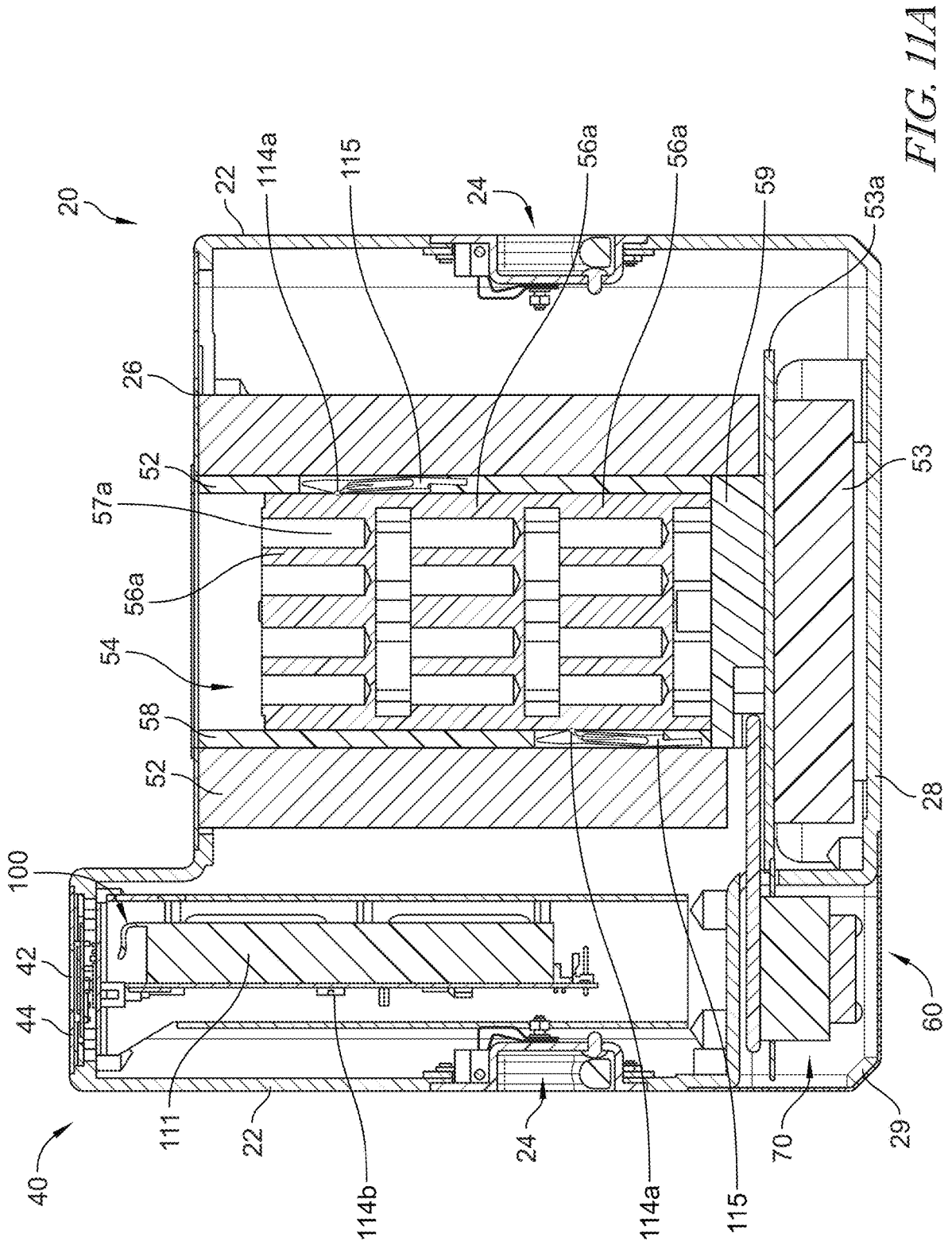
FIG. 11A is a section view of the portable incubation system of FIG. 1 taken along section line 11-11 showing the first embodiment of the inner block configured to receive vials.
Figure 11B:
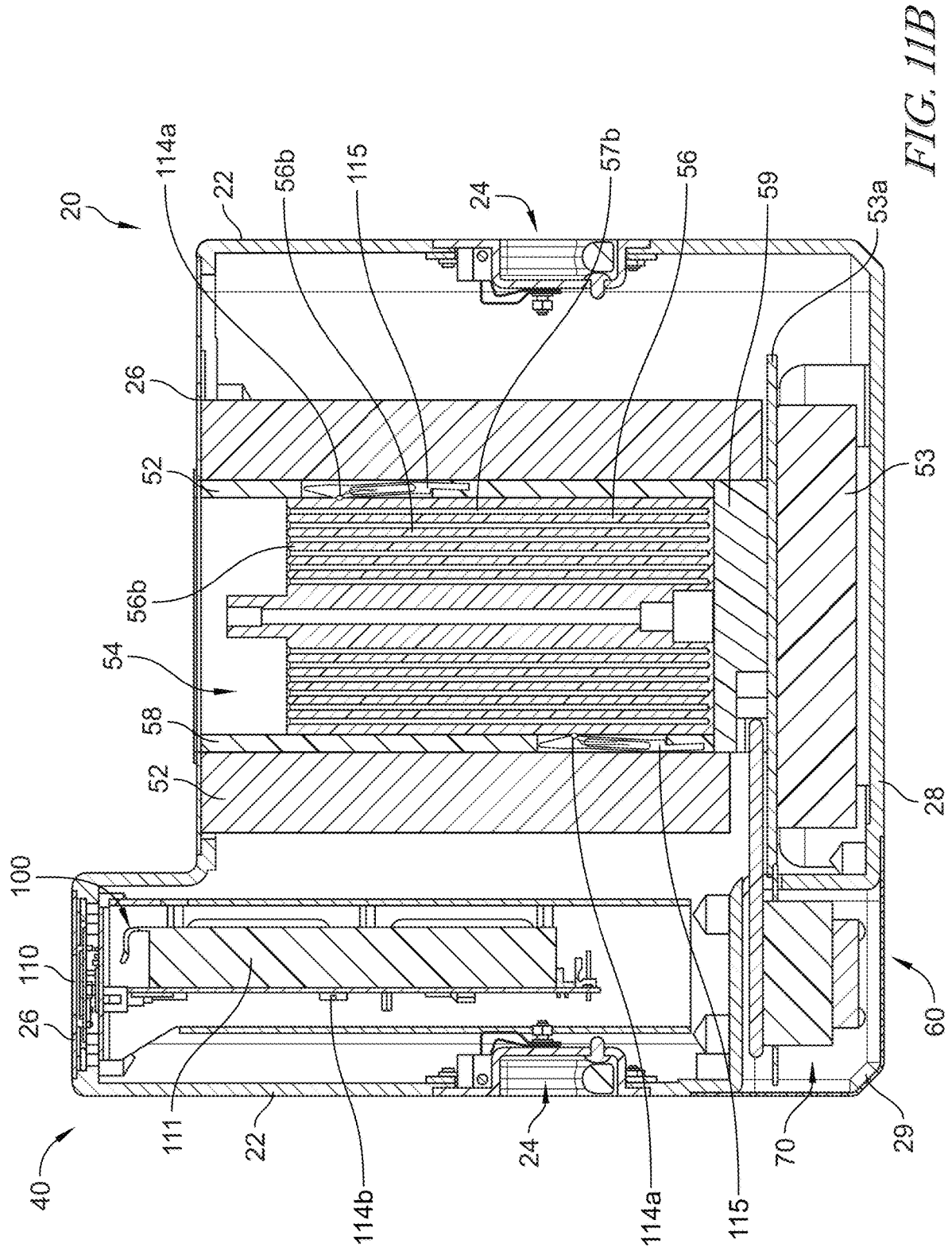
FIG. 11B is a section view of the portable incubation system of FIG. 1 taken along section line 11-11 showing the second embodiment of the inner block, which is configured to receive straws.
Figure 12:
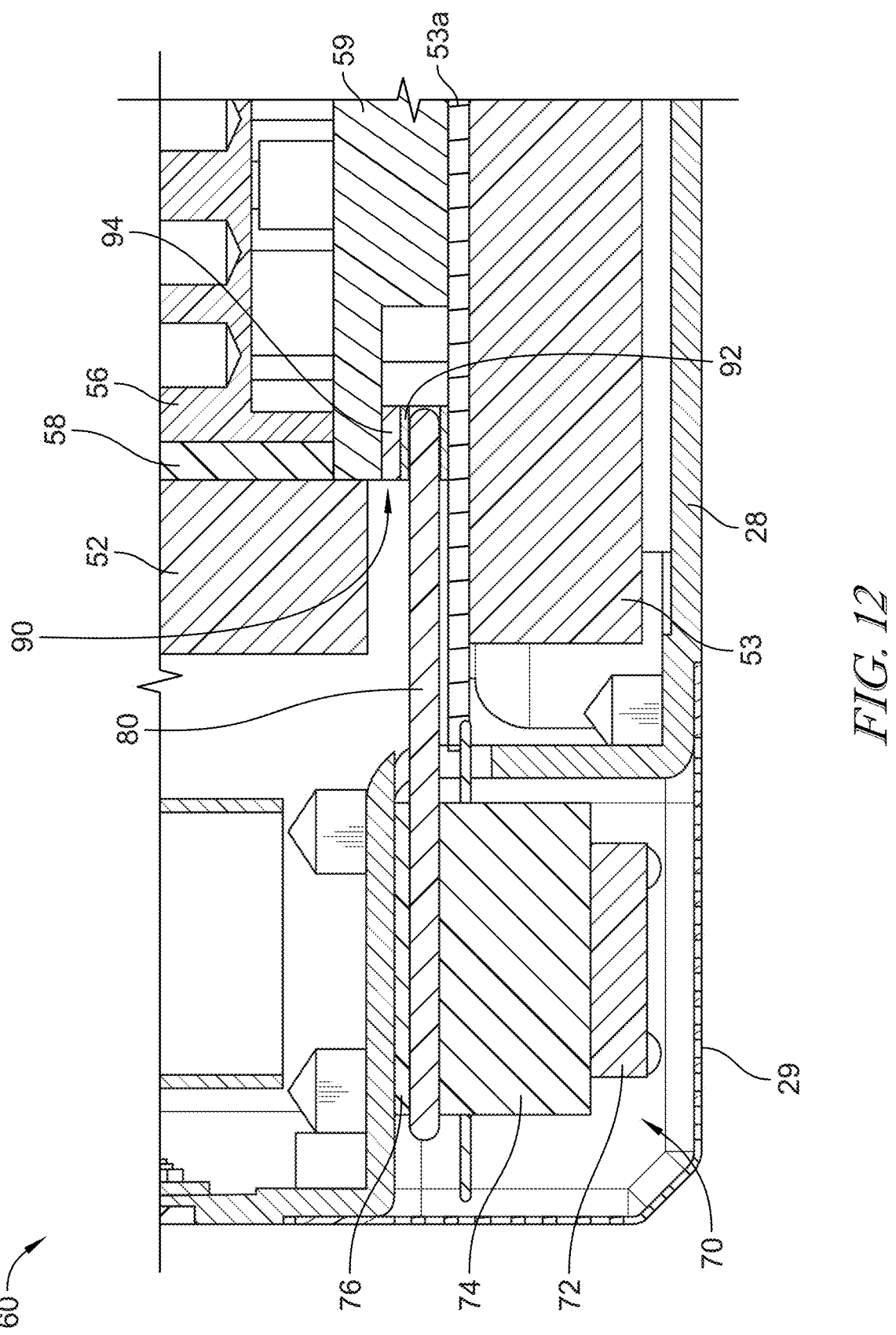
FIG. 12 is a section view of the temperature management system of the incubator of FIG. 1.
Figure 13:
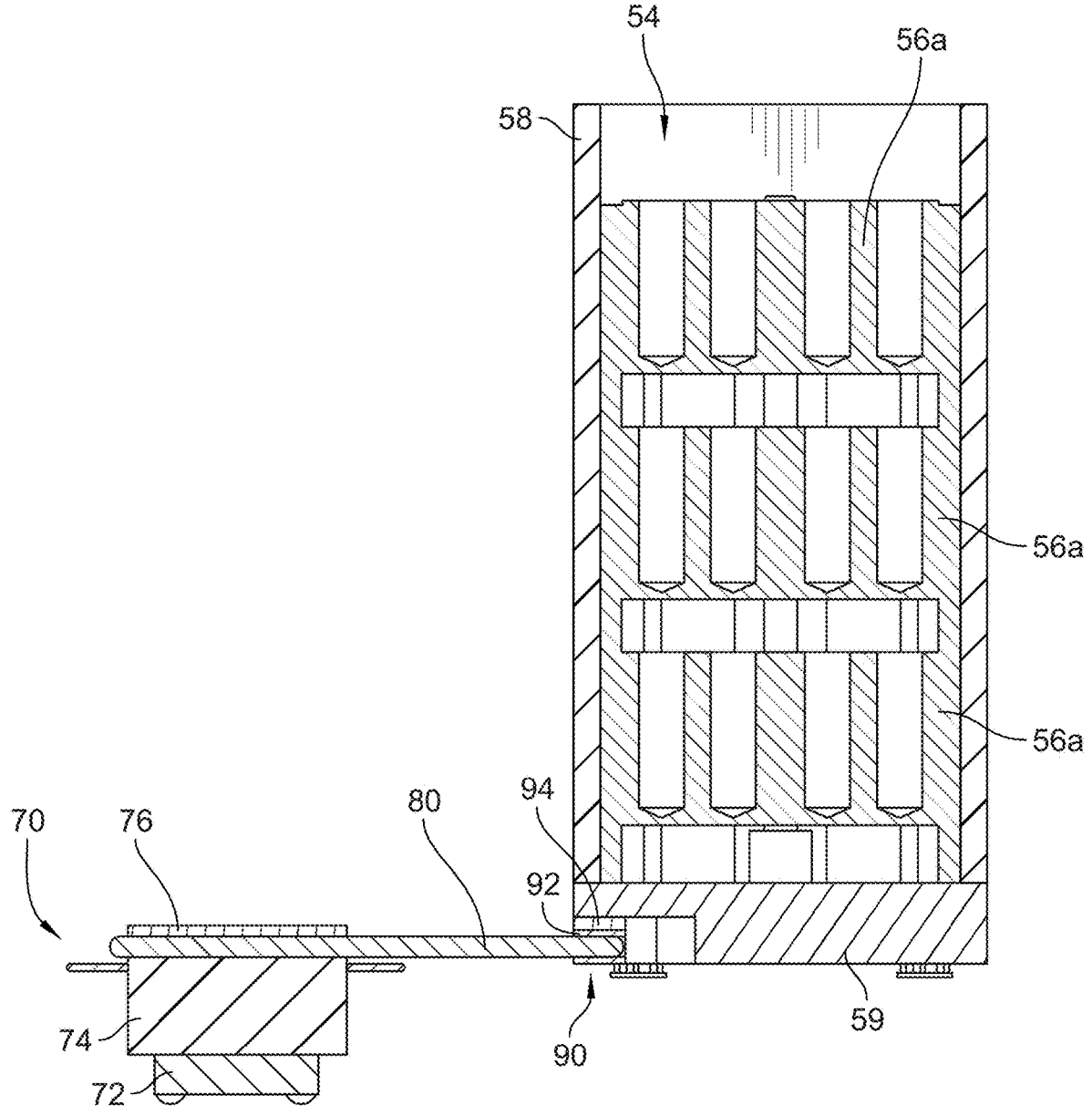
FIG. 13 is a section view of the inner chamber assembly of FIG. 10.

The inner chamber assembly 50 may include at least one inner block 56 arranged to fit within the inner chamber 54. The inner block 56 may be any shape or size such that the inner block 56 fits within the walls of the inner chamber 54. In one embodiment, the shape of the inner block corresponds to a cross-sectional shape or profile of the inner chamber 54 to maximize the capacity of the inner chamber 54. In one embodiment, the inner block 56 is square or rectangular. In some embodiments, as shown in FIGS. 8A and 11A, the inner block 56*a* may be shaped such that multiple inner blocks 56*a* may be stacked on top of one another within the inner chamber 54. In other embodiments, as shown in FIGS. 8B and 11B, a single inner block 56*b* may fill a majority of the inner chamber 54.

The at least one inner block 56 may be shaped to form a plurality of openings 57. Each of the plurality of openings 57 may be configured to hold at least one biological sample. The at least one biological sample may comprise embryos, oocytes, and/or gametes. The inner chamber assembly 50 may be configured to maintain the biological sample at a controlled temperature within a specific temperature range for preserving viability of the biological sample during transport of the portable incubation system 10.

In this embodiment, the inner block 56 is shaped to form a plurality of openings 57 configured to hold samples, such as tubes, vials, or straws containing biological samples. As shown in FIG. 11A, in some embodiments, the openings 57*a* may be configured to hold tubes and/or vials that are relatively shorter in length and larger in diameter than other sample containers. In some embodiments, as shown in FIG. 11B, the openings 57*b* may be configured to hold straws that are relatively longer in length and smaller in diameter than other sample containers. The openings 57 may be recesses extending into the inner block 56 with side walls and a bottom that define the recess. In other embodiments, the openings 57 may be through holes extending completely through the inner block. The biological samples may be any sort of biological or biomedical sample that should be kept within a specific temperature range for viability of the sample. For example, the samples may be embryos, semen, oocytes and/or gametes. In certain embodiments, the inner block 56 may be divided into sections to accommodate additional layers of openings to accommodate layers of biological sample containers. The number of layers may be determined by the size of the sample containers. For example, when configured to receive certain types of vials as shown in in FIGS. 8A and 11A, the inner core can be separated into three pieces, permitting three layers of biological samples. Shorter and/or smaller sample containers may allow for additional divisions of the inner core and more layers of biological samples. Conversely, in certain embodiments, for example when configured to receive straws as depicted in FIGS. 8B and 11B, the length of the biological sample container prevents dividing the inner core into additional layers.

The inner block 56 may be specifically designed to accommodate biological samples that require different orientations during transport for optimal viability. Certain biological samples must be maintained in specific orientations during transport to preserve their integrity and viability. For example, embryo straws are typically kept horizontal during transport, as vertical orientation could cause the embryo to float or sink to one end of the straw, potentially compromising embryo viability. In contrast, tubes containing collected oocytes typically require a vertical orientation for proper preservation.

The portable incubation system 10 addresses these varying orientation requirements through its adaptable design that enables operation in multiple configurations. As shown in FIGS. 19A-20B, the incubation system 10 can be operated in either a vertical orientation or a horizontal orientation. The vertical orientation accommodates a stack of inner blocks 56 with openings 57 configured for vertically-held tubes containing samples such as oocytes. The horizontal orientation, where the entire incubation system 10 is placed on its side as shown in FIGS. 20A-20B, accommodates inner blocks 56 with openings 57 configured for horizontally-held straws containing embryos.

This dual-orientation capability is enabled by design features that allow all components to function regardless of orientation. The lid 30, housing 40, and latch mechanisms are engineered to maintain proper sealing and security in both orientations. Similarly, the temperature management system 60, including the heat pipe 80, heat sink assembly 70, and thermoelectric cooler assembly 90, are designed to function effectively whether the incubation system 10 is positioned vertically or horizontally. The heat pipe 80, in particular, maintains thermal performance in either orientation, though with slight variations in efficiency as previously described.

The inner blocks 56 may be interchangeable and designed specifically for the orientation needs of particular biological samples. For example, a first set of inner blocks 56 may contain openings 57 sized and oriented for vertical tubes, while a second set of inner blocks 56 may contain openings 57 sized and oriented for horizontal straws. This modular approach allows the portable incubation system 10 to be quickly reconfigured based on the specific biological samples being transported. The different inner blocks 56 may be color-coded or otherwise visually distinguishable to indicate their intended sample type and orientation.

The openings 57 in the inner blocks 56 may be precisely sized to securely hold specific sample containers while maintaining optimal thermal contact. For horizontal straws containing embryos, the openings 57 may be elongated channels that run parallel to the horizontal plane when the incubation system 10 is in its horizontal orientation. For vertical tubes containing oocytes, the openings 57 may be cylindrical recesses that align with the vertical axis when the incubation system 10 is in its vertical orientation. This specialized design ensures that each type of biological sample is maintained in its optimal orientation throughout transport while still receiving uniform temperature control.

The openings 57 may be designed to maintain samples in thermal contact with the inner block 56 material while securing them in position during transport. The inner chamber assembly 50 may comprise a plurality of inner blocks 56 that are configured to stack on top of one another within the inner chamber 54. In this embodiment, the inner blocks 56 are rectangular and shaped to fit within the wall 58 of the inner chamber 54. The inner blocks 56 may comprise aluminum or any other suitable material capable of transferring heat between the temperature management system 60 to the samples.

Temperature Management System

The temperature management system 60 may be disposed within the housing 40. The temperature management system 60 may comprise a heat sink assembly 70 in thermal communication with an ambient environment of the portable incubation system 10, In one embodiment, the temperature management system 60 comprises a pre-heater 62, the heat sink assembly 70, a heat pipe 80, and a thermoelectric cooler (TEC) assembly 90.

The TEC assembly 90 may be coupled to the inner chamber assembly 50. The heat pipe 80 may be a water-based heat pipe 80 that extends between the heat sink assembly 70 and the thermoelectric cooler assembly 90. In an embodiment, the temperature management system 60 may be disposed within the housing 40 and is coupled to the inner chamber assembly 50, extending from the inner chamber assembly 50 to a vent 29 in the container 20.

In some embodiments, the temperature management system 60 is configured to respond to ambient temperature transitions around 20° C. by automatically adjusting thermal resistance properties of the water-based heat pipe 80. In some embodiments, the water-based heat pipe 80 automatically transitions between efficient heat transfer and increased thermal resistance at about 20° C., which corresponds to a transition point where a COP of the thermoelectric cooler assembly 90 changes from greater than 1 to less than 1.

The temperature management system 60 operates to heat or cool the container to bring an inner chamber 54 of the container to the predetermined threshold temperature and maintain the chamber 54 at that temperature, for example, while the incubation system 10 is used to move or transport the samples. The temperature management system 60 utilizes a heat sink assembly 70, a heat pipe 80, and a TEC assembly 90 arranged in series to control the temperature of the inner chamber 54. The heat sink assembly 70 is in thermal communication with the ambient environment to transfer heat between ambient airflow and fins of a heat sink 74. The heat pipe 80 extends between the heat sink assembly 70 and a TEC assembly 90 to transfer heat between the two. The TEC assembly 90 is coupled to the inner chamber 54 of the container 20 to transfer heat from the TEC 94 and heat pipe 80 to heat or cool the inner chamber 54. The temperature management system 60 is operated in a cooling mode, a first heating mode, or a second heating mode based on an ambient temperature and the COP of the TEC.

Heat Sink Assembly

In some embodiments, the temperature management system 60 is disposed within the housing 40 and comprises the heat sink assembly 70. The heat sink assembly 70 may be in thermal communication with an ambient environment of the portable incubation system 10. In some embodiments, the temperature management system 60 comprises a fan 72 configured to direct ambient air over the heat sink assembly 70.

The heat sink assembly 70 may be disposed within the housing 40, adjacent to the vent 29. The heat sink assembly 70 may be arranged to be in thermal communication with an ambient environment of the portable incubation system 10. As shown in FIGS. 7-8, the heat sink assembly 70 may include, for example, a heat sink 74, the fan 72, and a backing plate 76.

In this embodiment, the backing plate 76 may be coupled to a first side of the heat sink 74. The backing plate 76 couples an end of the heat pipe 80 to the heat sink 74 so heat can be transferred between the heat sink 74 and the heat pipe 80. The backing plate 76 may be shaped to at least partially surround the end of the heat pipe and couple the heat pipe 80 to the heat sink 74. A thermally conductive epoxy or paste may be used to couple the heat pipe 80 to the backing plate 76 and the backing plate 76 to the heat sink 74.

The heat sink 74 may comprise a plurality of fins or other geometric features arranged to transfer heat between the heat sink 74 and the ambient environment. For example, the fins may project outward and extend away from a base plate of the heat sink 74. The fins may be spaced apart from each other such that there is empty space between the fins that air may flow between to transfer heat between the airflow and the fins. The heat sink 74 and fins may comprise a thermally conductive material such as aluminum, copper, and/or another conductive metal or material. The fan 72 may be disposed adjacent to the fins of the heat sink 74.

The fan 72 may be disposed within the housing 40, adjacent to the vent 29, and arranged to direct airflow over the fins of the heat sink 74. The fan's 72 position and orientation may be optimized to maximize air flow across the heat sink fins. The fan 72 may direct airflow between the heat sink fins and the ambient environment through the vent 29, and the direction of the airflow may depend on the operating mode of the temperature management system 60. For example, during cooling operations, the fan 72 may draw warmer air away from the heat sink 74 and eject the warm air out into the ambient environment. During heating operations above the COP threshold, the fan 72 may help transfer ambient heat into the temperature management system 60 through the heat sink by drawing in warmer air from the ambient environment and directing the warm ambient air over the heat sink fins.

Thermoelectric Cooler Assembly

In some embodiments, the TEC assembly 90 comprises a TEC 94 coupled to the inner chamber 54 and disposed between the base 59 of the inner chamber 54 and at least one of the plurality of vacuum insulated panels 52, 53. A first side of the TEC 94 may be coupled to an exterior surface of the base 59 of the inner chamber assembly 54, the exterior surface being opposite an interior surface of the base 59. In some embodiments, the temperature management system comprises the water-based heat pipe 80. The water-based heat pipe 80 comprises a first and second end. In some embodiments, the first end is coupled to the heat sink assembly 70 and the second end is coupled to the TEC assembly 90.

In one embodiment, the TEC assembly 90 includes the TEC 94 and a TEC sink 92. In this embodiment, the TEC assembly 90 may be coupled to the inner chamber assembly 50 between the base 59 and the bottom vacuum insulated panel 53. One side of the TEC 94 may be coupled to the base 59 of the inner chamber assembly 50, on an outer surface of the base 59 opposite from the interior of the inner chamber 54. The TEC sink 92 may be coupled to an opposite side of the TEC from the inner chamber assembly 50. The TEC sink 92 may be arranged to at least partially surround an end of the heat pipe 80, coupling the heat pipe 80 to the TEC assembly 90 such that the heat pipe 80 extends between the TEC assembly 90 and the heat sink assembly 70.

Figure 14:
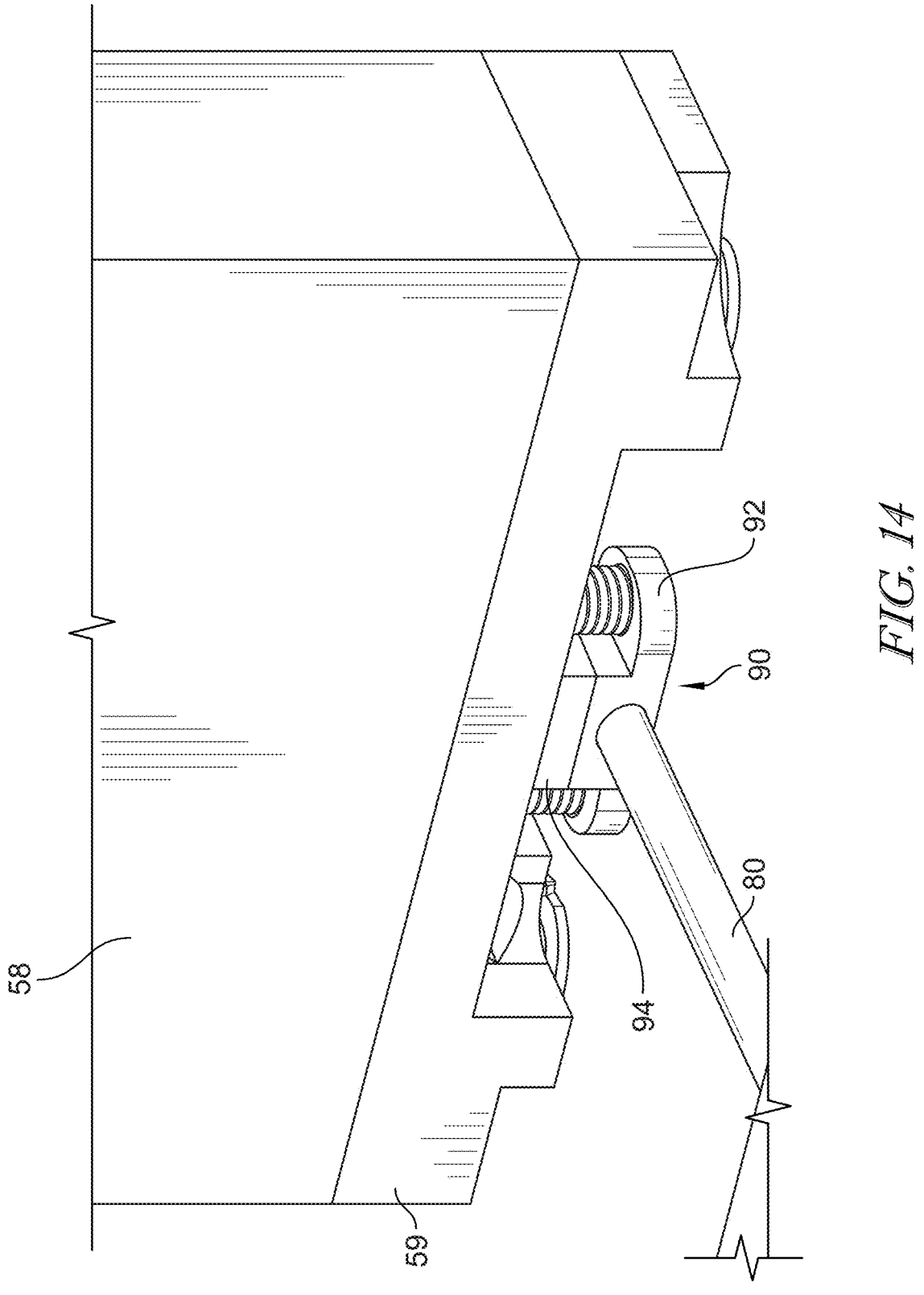
FIG. 14 is a detail view of the thermoelectric cooler and heat pipe of the temperature management system of FIG. 10.
Figure 15:
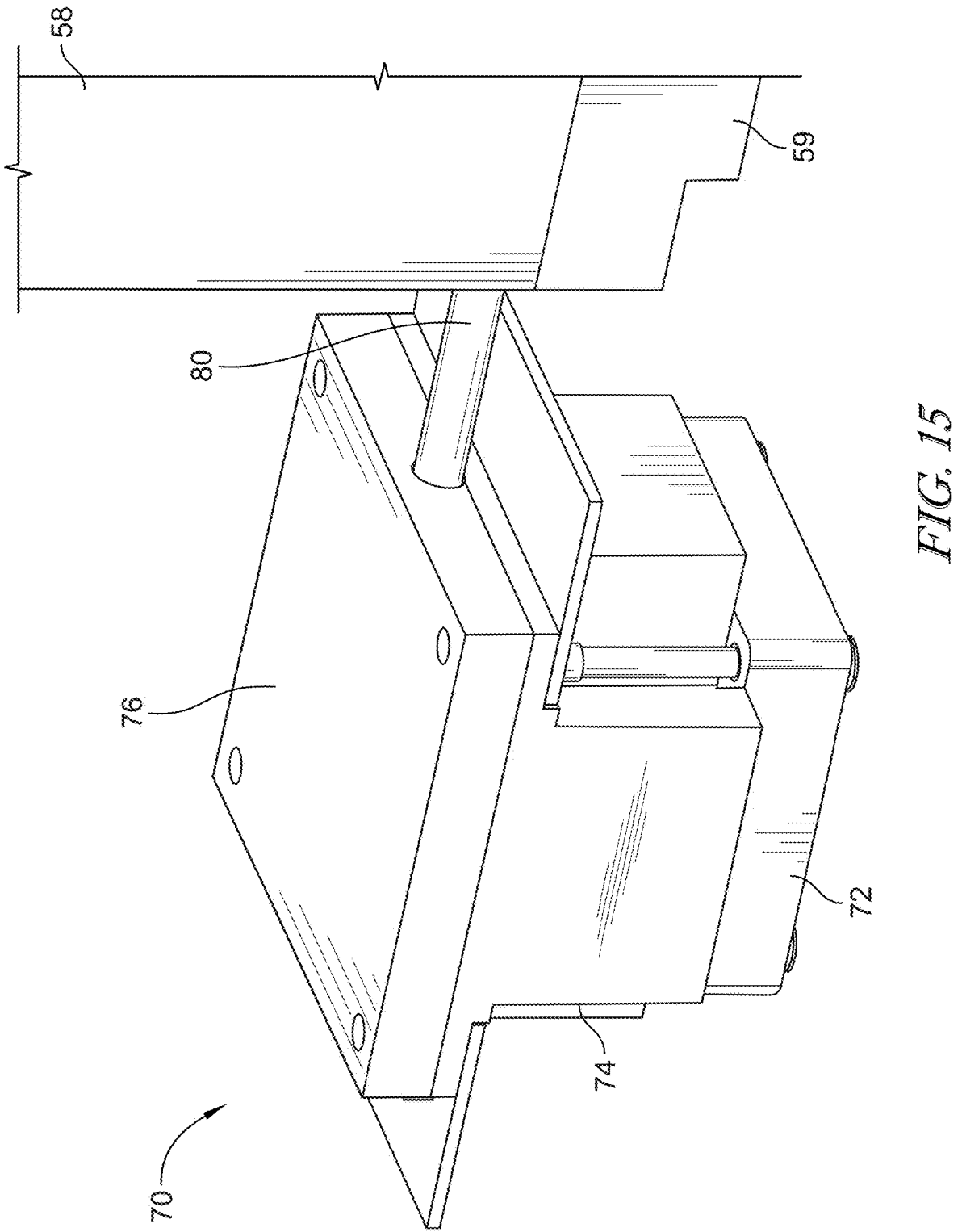
FIG. 15 is a detail view of the heat sink of the temperature management system of FIG. 10.

As shown in FIG. 14, the TEC sink 92 may include an aperture through which the heat pipe 80 extends such that the TEC sink 92 extends around a full circumference of the heat pipe 80. A thermally conductive epoxy or paste may be used to couple the TEC 94 to the base 59, the TEC 94 to the TEC sink 92, and/or the TEC sink 92 to the heat pipe 80. Additionally or alternatively, in some embodiments, the TEC sink 92 may be coupled to the base 59 via one or more fasteners, such as PEEK screws, as shown in FIG. 14, to mount the TEC sink 92 directly to the inner chamber 54. In some embodiments, the TEC sink 92 may be coupled to the panel backing plate 53*a*.

Pre-Heater

In an embodiment, the temperature management system 60 comprises the pre-heater 62. The pre-heater 62 may be in thermal communication with the inner chamber assembly 54. The control system 100 and/or controller 106 may be configured to activate the pre-heater 62 upon start up of the portable incubation system 10 to heat the inner chamber assembly 54 more efficiently than would be possible using the heat sink assembly 70, the water-based heat pipe 80, and TEC assembly 90 alone.

The pre-heater 62 may be suitable for heating the inner chamber assembly 50 and powered by the power source 102. The pre-heater 62 may be coupled to the exterior surface of the base 59 to provide heat to the inner chamber 54. The pre-heater 62 may be used to transfer heat to the inner chamber 54 upon start-up of the incubation system 10 to quickly heat up the inner chamber 54 up to a desired temperature.

Heat Pipe

In one embodiment, the heat pipe 80 is a water heat pipe, where the primary working fluid within the heat pipe is water and/or water vapor. In some embodiments, the heat pipe 80 is configured to transfer heat through vapor exchange. When a temperature of the ambient environment is greater than 20° C., the heat pipe 80 may be configured to transfer heat between the heat sink assembly 70 and the TEC assembly 90. When a temperature of the ambient environment is less than 20° C., the heat pipe 80 may be configured to reduce heat transfer between the heat sink assembly 70 and the TEC assembly 90 by, for example, providing thermal resistance.

The heat pipe 80 operates through a continuous cycle of vaporization and condensation of the working fluid within the heat pipe 80. The heat pipe 80 may be generally cylindrical in shape with a body extending between two ends of the heat pipe 80. Alternatively, the heat pipe 80 may be flat and/or have an oblong cross section. At the end of the heat pipe 80 disposed in an area with a relatively high temperature, the working fluid absorbs thermal energy and evaporates. The vapor moves along the heat pipe 80 body towards the opposite end of the heat pipe 80, which is disposed in an area with a relatively lower temperature. At the cooler, lower temperature end, the vapor releases the thermal energy and condenses back to a fluid. The condensed fluid moves back to the higher temperature end and the cycle repeats.

In one embodiment where the working fluid in the heat pipe 80 is water, at temperatures above approximately 20° C., the water within the pipe vaporizes at the heated end, creating a pressure differential that drives vapor flow to the cooler end where it condenses back to liquid. The pipe forming the heat pipe 80 may be any suitable material, including for example a copper pipe. In one embodiment, the heat pipe 80 comprises a hollow tube lined with a wick and filled with water. The heat pipe 80 transfers heat through vapor exchange: water vaporizes at a hot end of the pipe 80, flows to a cold end of the pipe 80 where the water condenses, then returns via the wick, which provides capillary action that returns the condensed liquid to the heated end, completing the cycle. The heat pipe 80 may operate efficiently above approximately 20° C. but may lose efficiency below this temperature. Below 0° C., the water freezes, limiting heat transfer to conduction only.

The water-based heat pipe 80 may enable the heat pipe 80 to have dual functionality. Above approximately 20° C., the water heat pipe 80 may enable efficient heat transfer through vapor exchange. Below approximately 20° C., the water heat pipe 80 may reduce heat transfer between the TEC assembly 90 and the heat sink assembly 70 as water vapor transport through the heat pipe 80 effectively ceases.

In some embodiments, the TEC 94 exhibits highest efficiency when the temperature differential between a control temperature or internal temperature of the inner chamber 54 and a temperature of the ambient environment is minimal or within +/-5° C. of the control temperature. For example, in some embodiments where the predetermined threshold temperature is 38.5° C., the TEC 94 may be most efficient when the ambient temperature is between 33.5° C. and 43.5° C. Heat transfer through the inner chamber assembly's 50 insulation scales linearly with temperature differential. Consequently, maintaining a desired setpoint or predetermined threshold temperature may require exponentially more power as the ambient temperature deviates further. For example, maintaining a desired predetermined threshold internal temperature of 38.5° C. may require approximately 20 times more power at an ambient temperature of −40° C. as compared to an ambient temperature of 30° C. This imbalance in efficiency may be due to the nonlinear performance of the TEC 94 at higher ΔT, or when the temperature difference across the TEC 94 is higher.

In some embodiments, the water-based heat pipe 80 operates according to the coefficient of performance (COP) of the TEC 94. When TEC COP is greater than 1 (or the temperature is greater than 20° C.), the heat pipe 80 provides efficient heat transfer. When the TEC COP is less than 1 (or the temperature is less than 20° C.), the heat pipe 80 adds thermal resistance, reducing heat loss from the inner chamber 54. This alignment between the heat pipe's 80 performance transition and the TEC's COP transition point improves the system's efficiency in cold conditions, because at the same transition point where the TEC's heating ability becomes less efficient, the heat pipe 80 begins acting as an insulator. The heat pipe's 80 position between the TEC and the cold, ambient environment helps reduce heat loss from the TEC 94 to the ambient environment, which would otherwise further decrease the TEC's heating efficiency. The heat pipe's 80 position helps reduce heat loss from the TEC 94 to the ambient environment as compared to if the TEC 94 was exposed or positioned closer to the ambient environment and/or if the liquid within the heat pipe 80 did not freeze or stop vaporizing as easily. The control system of the incubation system further directs components of the incubation system to operate according to the ambient temperature and determined COP of the TEC to operate the incubation system more efficiently. Alternatively, the COP may shift from greater than 1 to less than 1 at different temperatures than 20° C. For example, the COP shift to below 1 may happen at approximately 0° C. The temperature at which the COP shifts from greater than 1 to less than 1 may depend on the thermal performance of the overall incubation system.

Control System

In an embodiment, the control system 100 and/or the controller 106 is configured to direct the temperature management system 60 to regulate a temperature of the inner chamber assembly 50 based on an ambient temperature. The control system 100 may be disposed within the housing 40 and comprises, in some embodiments: a power source 102 operable to power the portable incubation system 10, the controller 106, a user interface 110, and/or control electronics 111. In some embodiments, the control system 100 comprises at least one temperature sensor 114 disposed throughout the incubation system 10.

In some embodiments, the control system 100 and/or the controller 106 are configured to direct the temperature management system 60 to regulate a temperature of the inner chamber assembly 50, for example, by operating at least one of the fan 72, the TEC assembly 90, and/or the power source 102 operable to power the portable incubation system 10. In an embodiment, the control system 100 and/or the controller 106 may be operable to direct the temperature management system 60 to cool the inner chamber assembly 50 when the internal temperature of the inner chamber assembly 50 is above a predetermined threshold temperature. In an embodiment, the control system 100 and/or the controller 106 may be operable to direct the temperature management system 60 to heat the inner chamber assembly 50 when the internal temperature of the inner chamber assembly 50 is below the predetermined threshold temperature.

The control electronics 111 may include and be referred to as a printed circuit board (PCB). The user interface 110 may be a graphical user interface and may provide real-time system status information including current internal temperature, ambient temperature, operational mode, and/or power status. The user interface may include a OLED or other type of graphical display. Through the interface 110, a user may adjust temperature thresholds, monitor system performance, and receive alerts if temperature limits are exceeded, if the power source is low, and/or if another issue that may affect operation of the incubation system 10 occurs. The interface 110 may include visual indicators showing active system components such as the fan 72, TEC 94, and pre-heater 62.

In some embodiments, the controller 106 is configured to determine a coefficient of performance (COP) of the TEC assembly 90 based on a temperature differential between the inner chamber assembly 50 and the ambient environment. In some embodiments, the controller 106 is configured to determine the COP of the TEC assembly 90 based on a difference in temperature across the water-based heat pipe 80. In some embodiments, the controller 106 is configured to operate the temperature management system 60 in a first heating mode when the COP is greater than 1. The first heating mode may utilize both the thermoelectric cooler assembly 90 and ambient heat transfer by way of the water-based heat pipe 80. For example, the first heating mode may comprise operating both the TEC 94 and the fan 72 to transfer heat from the ambient environment by way of the water-based heat pipe 80.

In some embodiments, the controller 106 may be configured to operate the temperature management system 60 in a second heating mode when the COP is less than 1. The second heating mode may utilize the water-based heat pipe 80 as thermal insulation between the thermoelectric cooler assembly 90 and the ambient environment. For example, the second heating mode may comprise operating the TEC 94 and not operating the fan 72, utilizing the reduced heat transfer capability of the water-based heat pipe as thermal insulation.

Optionally, the control system may include a processor 108 and a memory 112. The control system 100 may be configured to regulate an internal temperature or control temperature of the inner chamber 54. The control temperature may be set based on a predetermined threshold temperature. The predetermined threshold temperature may be determined based on a value input by a user via the user interface 110. The predetermined threshold temperature may be stored in the memory 112. The control system 100 may utilize the controller 106, memory 112, and processor 108 to carry out programs, user inputs, and/or desired adjustments to the incubation system 10.

The predetermined threshold temperature may serve as both a target temperature for the inner chamber 54 and a decision point for the control system 100. When the internal temperature of the incubation system 10 deviates from this threshold, the control system 100 determines whether to activate heating or cooling operations of the temperature management system 60. The threshold may include both an upper and lower limit to create an acceptable temperature range for maintaining samples. The threshold may be adjusted through the user interface based on specific sample requirements.

The controller 106 may be configured to seamlessly transition between a cooling mode, a first heating mode, and a second heating mode based on continuous sensor feedback, for example, from one or more temperature sensors 114. The transition points between modes may be determined by both an internal temperature of the inner chamber assembly 50 relative to a predetermined threshold temperature and/or the ambient temperature relative to a coefficient of performance transition point.

At least one of the temperature sensors 114 may be disposed in the inner chamber assembly 50 to detect an internal temperature of the inner chamber assembly 50. At least one of the temperature sensors 114 may be disposed on the housing 40 to detect a temperature of the ambient environment. The controller 106 and/or control system 100 may be configured to regulate the internal temperature of the inner chamber assembly 50 based on temperature feedback from the plurality of temperature sensors 114.

One or more temperature sensors 114 may be disposed throughout the incubation system 10 and may be enabled to communicate with the controller 106 and processor 108. As will be described in more detail below, the controller 106 and processor 108 may direct the temperature management system 60 to heat or cool the inner chamber 54 based on feedback from the temperature sensors 114 and the predetermined threshold value One or more of the temperature sensors 114*b* may be placed on or withing the housing 40, for example, on the PCB 111 as shown in FIGS. 11A and 11B to detect an ambient temperature.

In some embodiments, the control system 100 includes a plurality of sensors 114, such as temperature sensors, disposed on and/or within the portable incubation system 10. In some embodiments, at least one of the temperature sensors 114 is disposed in the inner chamber assembly 50 to detect an internal temperature of the inner chamber assembly 50. In some embodiments, at least one of the temperature sensors 114 may be disposed in the inner chamber 54 is coupled to a biasing mechanism, wherein the biasing mechanism 115 is configured to bias the temperature sensor 114 towards the at least one inner block 56 to contact an outer surface of the inner block 56.

One or more temperature sensors 114a may be disposed within the inner chamber 54, for example, on an interior surface of the inner walls 58 and/or the base 59 to measure the core temperature of the inner chamber 54. The inner chamber temperature sensors 114a may be disposed on a biasing mechanism 115 configured to bias the temperature sensor 114a towards the inner blocks 56 to contact a surface of the inner blocks 56. The biasing mechanism 115 may couple the temperature sensor 114a to an inner surface of the inner wall 58 of the inner chamber assembly 50, as shown in FIGS. 11A and 11B. The biasing mechanism 115 may be a spring or any other suitable component capable of coupling the temperature sensor 114a to the inner wall 58 and pushing and/or biasing the temperature sensor 114a towards the center of the inner chamber 54. The biasing mechanism 115 may bias the sensor 114a towards the center of the inner chamber 54 such that the sensor 114a contacts at least one of the inner blocks 56 when a block 56 is inserted into the inner chamber 54. The biasing mechanism 115 may be, for example, a low-profile compliant spring mechanism that is compact enough in size to fit between the inner blocks 56 and the surrounding vacuum insulated panels 52.

In some embodiments, the inner block 56 comprises a first inner block and a second inner block. The first inner block 56 and the second inner block 56 may be configured to stack vertically within the inner chamber 54. The plurality of temperature sensors 114 may comprise a first temperature sensor 114 disposed in the inner chamber assembly to detect a temperature of the first inner block 56. The plurality of temperature sensors 114 may comprise a second temperature sensor 114 disposed in the inner chamber assembly 50 and spaced apart from the first temperature sensor 114 to detect a temperature of the second inner block 56.

The design and/or orientation of the biasing mechanism 115 and the sensors 114a enable the sensors 114a to have perpendicular contact with the inner blocks 56 relative to their direction of insertion. This design makes the biasing mechanisms 115 and sensors 114a robust and effective across different inner block 56 configurations, allowing for temperature detection of different configurations of inner blocks 56a, 56b. This perpendicular contact approach enables precise temperature monitoring in a compact form factor where conventional sensor placement may not be possible. As shown in FIGS. 11A and 11B, the inner chamber 54 may include multiple temperature sensors 114a and biasing mechanisms 115 disposed at various locations within the inner chamber 54. Temperature sensors 114a may be disposed on different biasing mechanisms 115 to contact different inner blocks 56 and/or different areas of an inner block 56 within the inner chamber 54. For example, the sensors 114a may be positioned to make direct contact with the upper and/or lower inner blocks 56a, as shown in FIG. 11A, when inserted into the inner chamber 54. The various locations of the sensors 114 may provide accurate temperature readings through direct contact measurement rather than inferring temperatures indirectly through contact surfaces.

In some embodiments, the temperature sensors 114 work together to provide a thermal profile of the system 10. For example, an internal temperature sensor may monitor the actual conditions experienced by the samples in the inner chamber 54, whereas an ambient temperature sensor may enable the control system 100 to anticipate thermal loads and adjust heating or cooling operations accordingly. Additional temperature sensors 114 may be placed at key points in the thermal path, such as at the heat sink 74 and TEC 94, to monitor system performance and efficiency.

Power Source

The control system 100 may comprise the controller 106 and a power source 102 operable to power the portable incubation system 10. In some embodiments, the power source 102 is a battery configured to power the portable incubation system 10 to maintain biological samples at a controlled temperature for at least four hours during transport. In some embodiments, the control system 100 is configured to monitor power consumption and adjust operational parameters during different operational modes to extend operational time of the power source 102.

The incubation power source 102 provides power to the various components of the system 10. For example, the power source 102 may be in electrical communication with the temperature management system 60 and the control system 100 to power at least the fan 72, the TEC 94, the pre-heater 62, and the control system 100 components. In one embodiment, the power source 102 is a battery, which allows the incubation system 10 to be portable and self-contained.

In an embodiment, the method comprises monitoring power consumption of the portable incubation system 10 during steady-state operation using the control system 100 and/or controller 106. During steady-state operation, power may be primarily required for the TEC 94 and periodic fan 72 operation.

The power requirements of the system may vary significantly based on, for example, operational mode and ambient conditions. In some embodiments, the control system 100 monitors power consumption and may adjust operational parameters to optimize the life of the power source 102 (e.g., battery). During steady-state operation, the system primarily requires power for the TEC 94 and periodic fan 72 operation. The pre-heater 62 draws additional power during startup but operates only briefly to reach initial temperature targets, at which point the heat sink assembly 70, heat pipe 80, and TEC assembly 90 are responsible for temperature management.

The power source 102, when embodied as a battery, is designed to enable extended operation of the portable incubation system 10 during transport. In various embodiments, the battery capacity is selected to maintain the inner chamber 54 at the predetermined threshold temperature for different durations based on intended use. For short-distance transport, the battery may power the system for at least two, three, or four hours. For medium-distance transport, embodiments with enhanced battery capacity can maintain operation for at least six, eight, or ten hours. For long-distance or extended transport scenarios, high-capacity battery configurations can power the incubation system for at least twelve, eighteen, or twenty-four hours, and in some embodiments, up to thirty-six or forty-eight hours. Some specialized embodiments may incorporate extended-life battery arrangements capable of maintaining operation for three to five days in controlled conditions. All intermediate values and durations between the specifically listed time periods are also contemplated. The actual operational duration may vary based on ambient conditions, with operation in extreme temperatures (below 0° C. or above 40° C.) potentially reducing the effective battery life due to increased power requirements. The control system 100 may include power management features that optimize component operation to extend battery life when needed. The portable incubation system 10 may also include a USB port or other form of charging port to allow battery charging when plugged in. Proximity and/or NFC charging technologies may also be incorporated into the portable incubation system 10 to allow charging by placing the portable incubation system 10 on an induction or other proximity based charging device.

Smart Monitoring and Communication Features

In an embodiment, the portable incubation system 10 comprises a wireless communication module operatively in communication with the control system 100 and/or the controller 106. The wireless communication module may be configured to transmit temperature data and location data to a remote monitoring system. Additionally or alternatively, the portable incubation system 10 may comprise a GPS module 116 operatively in communication with the control system 100 and/or the controller 106. The GPS module 116 may be configured to provide real-time location data of the portable incubation system 10 during transport. The control system 100 and/or the controller 106 may be configured to define a geofenced route for transport of the portable incubation system 10, monitor the location of the portable incubation system 10 relative to the geofenced route, and trigger an alert when the portable incubation system 10 deviates from the geofenced route.

In addition to the core temperature management and control systems described above, certain embodiments of the portable incubation system 10 may be equipped with smart features that enhance real-time monitoring, tracking, and data communication. By integrating GPS tracking, temperature history recording, and wireless connectivity, these embodiments may improve oversight and management of temperature-sensitive biological samples during transit.

Advancements in Internet of Things (IoT) technology have created opportunities to improve the functionality of temperature-controlled containers such as the portable incubation system 10 described herein by integrating smart features that allow remote monitoring, predictive analytics, and enhanced supply chain visibility. Certain embodiments of the portable incubation system 10 incorporate smart functionalities that enable precise tracking and environmental monitoring. For example, the portable incubation system 10 may include an integrated GPS module 116 for real-time location tracking, a temperature monitoring system that records and stores temperature history, and wireless connectivity via cellular and Wi-Fi networks. These features allow for seamless data transmission to cloud-based platforms, enabling remote access and automated alerts.

The smart features described above may be implemented through additions to the control system 100. The processor 108 and memory 112 components may be expanded to include the necessary processing power and storage capacity for these enhanced monitoring and communication capabilities. The user interface 110 may be enhanced to include wireless communication capabilities and display additional status information related to GPS location, security features, and remote monitoring alerts. These smart features represent optional enhancements to the core portable incubation system 10 and may be included in specific embodiments without altering the fundamental temperature management functionality described herein.

In addition to these core functionalities, the portable incubation system 10 may include advanced diagnostic and control mechanisms, such as predictive maintenance alerts, automated environmental adjustments, and security features that enhance operational efficiency and security. By leveraging connectivity and real-time analytics, some embodiments of the invention may significantly improve the reliability and security of biological sample shipping logistics.

In certain embodiments, temperature sensors 114 positioned throughout the portable incubation system 10 continuously monitor conditions, with recorded data stored in the memory 112 and transmitted via wireless communication. A GPS module may be integrated into the controller 106 to provide real-time location data, enabling logistics providers to track shipments with precision. Wireless communication capabilities, including cellular and Wi-Fi connectivity, allow for remote monitoring of both temperature conditions and location status. The system is capable of sending automated alerts in the event of temperature fluctuations, prolonged delays, or unauthorized access.

In one embodiment, the portable incubation system 10 is equipped with a diagnostics system that continuously monitors the performance of critical components, such as the TEC 94, power source 102, fan 72, and temperature sensors 114. Using machine learning algorithms, the system may analyze historical performance trends to predict potential failures before they occur. If the system detects an anomaly, it may notify operators in real-time, allowing for proactive maintenance and reducing the risk of unexpected failures that could compromise a shipment.

Another embodiment may feature an intelligent environmental control system that dynamically adjusts the internal temperature based on external conditions and shipment requirements. Sensors inside and outside the portable incubation system 10 monitor temperature, humidity, and atmospheric pressure, allowing the system to optimize energy consumption while maintaining the required temperature range. For instance, if external temperatures climb, the system may reduce thermoelectric heating to conserve power, while still ensuring that the internal temperature remains stable.

In another possible embodiment, the portable incubation system 10 may be fitted with smart security features to prevent unauthorized access and tampering. A biometric or RFID-based access control system restricts entry to authorized personnel, ensuring that the contents remain secure throughout transit. Additionally, an integrated motion and impact detection system can identify potential tampering attempts or accidental drops, triggering alerts that notify the shipment owner and logistics provider.

A further embodiment may incorporate blockchain technology to ensure the integrity and authenticity of recorded shipment data. Temperature logs, location history, and access records are securely stored in an immutable blockchain ledger, providing verifiable proof of compliance with industry regulations. This technology enhances transparency, reduces the risk of data manipulation, and simplifies regulatory reporting for industries that require stringent temperature documentation.

In another embodiment, the portable incubation system 10 may use GPS tracking to incorporate geofencing capabilities, allowing it to automatically notify operators when it enters or exits predefined areas such as ports, warehouses, or delivery zones. If a portable incubation system 10 is moved outside of its designated route or stopped for an unauthorized period, the GPS and cellular connection could trigger an automatic security alert. A combination of GPS tracking and motion sensors could detect unauthorized movements, alerting logistics teams to potential theft, hijacking, or misrouting.

The portable incubation system 10 may also be equipped with accelerometers and gyroscopic sensors that detect excessive shocks, tilts, or vibrations during transit. If a portable incubation system 10 is dropped, tilted beyond a safe angle, or subjected to prolonged vibrations (such as from a rough road or turbulence), an alert could be sent via cellular communication, allowing the logistics team to assess potential damage before delivery.

Another embodiment may incorporate smart electronic seals that immediately notify operators via cellular network if they are broken or tampered with before reaching their final destination. This could prevent unauthorized access and ensure compliance with security regulations.

These smart features are designed to complement the fundamental temperature management capabilities of the portable incubation system 10, enhancing its utility for transporting sensitive biological samples while maintaining the core functionality described in previous sections. Implementation of these features may be modular, allowing customers to select specific smart capabilities based on their particular requirements and use cases.

Incubator Operation

In an embodiment, a method of regulating an internal temperature of the portable incubation system 10 comprises determining the internal temperature of the inner chamber 54 of the inner chamber assembly 50 using a temperature sensor 114 disposed within the inner chamber 54. In an embodiment, the method comprises operating, using the control system 100 and/or the controller 106, the TEC 94 of the TEC assembly 90 to heat the inner chamber 54 when the internal temperature is below a predetermined threshold temperature. The TEC 94 may be coupled to the base 59 of the inner chamber 54, between the inner chamber 54 and at least one of the vacuum insulated panels 52, 53 of the portable incubation system 10. In an embodiment, the method comprises determining the COP of the TEC 94. The method may comprise operating, using the control system 100 and/or the controller 106, the fan 72 when the coefficient of performance is above 1 to heat the inner chamber 54. The fan 72 may be disposed within the housing 40 of the portable incubation system 10 and arranged to direct ambient air over the heat sink assembly 70.

FIGS. 16A-18B show example steps of methods of operation of the incubation system 10. During operation, the control system 100 directs the components of the temperature management system 60 to regulate the internal temperature of the inner chamber 54. The inner chamber 54, the TEC assembly 90, the heat pipe 80, the heat sink assembly 70, and the ambient environment of the incubation system 10 are arranged in series to transfer heat between components to heat or cool the inner chamber 54.

As shown in FIGS. 16A-18B, during operation, the control system 100 regulates the control temperature or internal temperature of the inner chamber assembly 50 based upon a predetermined threshold temperature or setpoint. A user may input the predetermined threshold temperature into the control system via the user interface 110. The predetermined threshold temperature may be stored in the memory 112 and referenced by the controller 106 and/or processor 108 to regulate and/or make adjustments to the incubation system. Alternatively or additionally, the predetermined threshold temperature may be pre-programmed into the control system 100.

In an embodiment, the method comprises determining the ambient temperature using a temperature sensor 114 disposed on or within the housing 40 of the portable incubation system 10, and using the determined ambient temperature to calculate the coefficient of performance of the TEC 94.

During operation, the control system 100 receives continuous feedback from the plurality of temperature sensors 114 disposed on and within the incubation system 10. Upon start up of the incubation system 10, the temperature sensors 114 provide initial temperature readings to determine the temperature differential between the inner chamber 54 and the target temperature. The control system 100 may direct the pre-heater to turn on to warm up the inner chamber 54 more quickly and efficiently than the TEC assembly 90, heat pipe 80, and heat sink 74 may be able to. Once a sensor 114a within the inner chamber 54 indicates that the inner chamber 54 has reached the predetermined threshold temperature, the control system 100 may turn off the pre-heater.

The controller 106 and processor 108 receive continuous feedback from the plurality of temperature sensors 114 and determines which mode the incubation system 10 will operate in. When one of the sensors within the inner chamber 54 indicate that the internal temperature of the inner chamber 54 has fallen below the predetermined threshold temperature, the controller 106 directs the temperature management system 60 to enter heating mode, as shown in FIGS. 17A-18B. Additionally, the temperature sensor disposed on the housing 40 of the incubation system 10 to determine the ambient temperature may be used to determine whether the COP of the TEC 94 is greater than or less than 1 for the desired predetermined threshold temperature. For example, the temperature sensors disposed on or within the housing 40 and/or inside of the inner chamber 54 may determine the temperature difference, or $\Delta T$, across the heat pipe 80 by subtracting the ambient temperature from the inner chamber 54 temperature. Alternatively or additionally, the $\Delta T$ across the heat pipe 80 may be calculated based on the ambient temperature and the predetermined threshold temperature that the heat pipe 80 is working to heat the inner chamber 54 to. This temperature difference across the heat pipe 80 may represent the amount of heating or cooling provided by the heat pipe 80, which may in turn be used to determine the COP of the heat pipe 80. The determination of the COP is used to direct the system 10 to enter either a first heating mode 1700 or a second heating mode 1800.

Figure 17B:
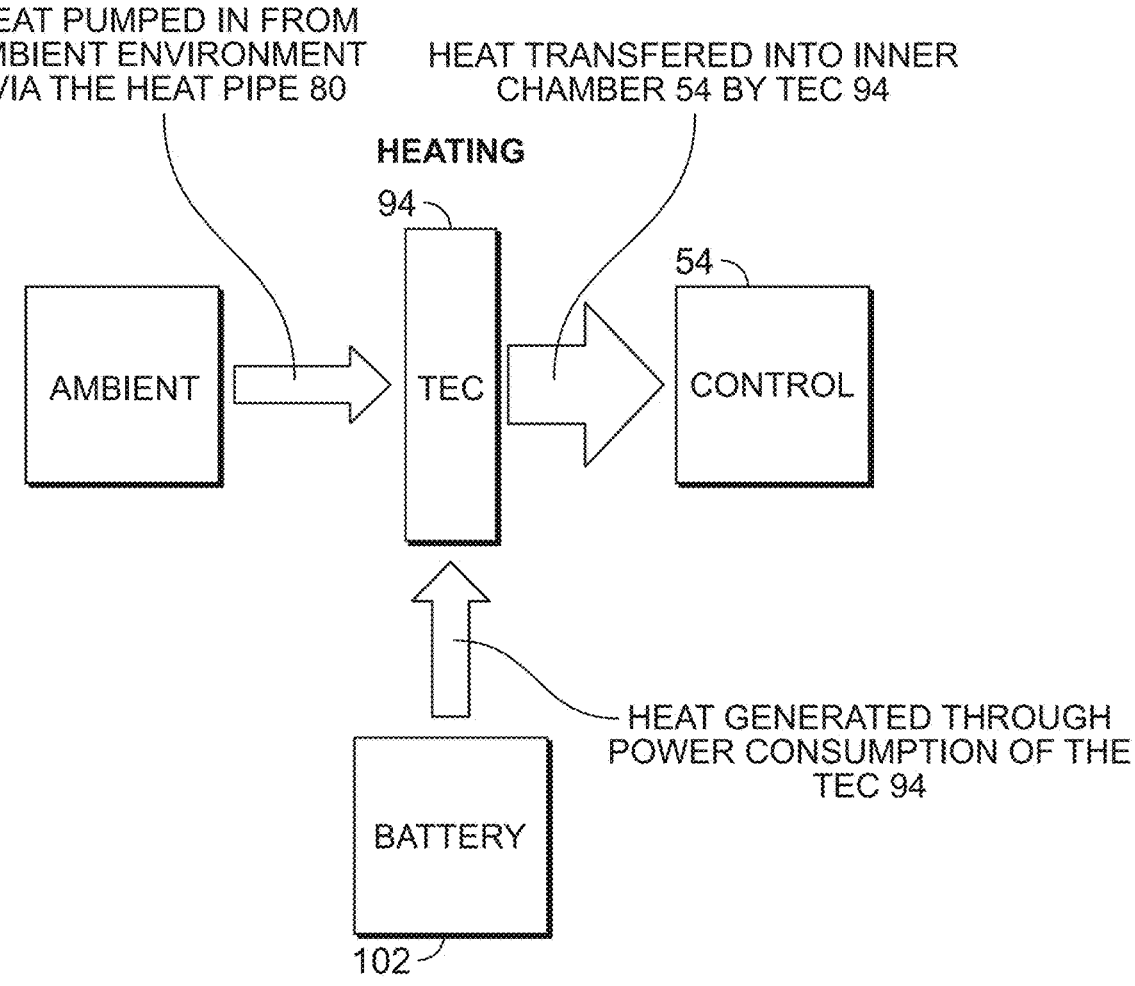
FIG. 17B is a diagram of the portable incubation system of FIG. 1 in the first heating mode.

The first heating mode 1700 is shown in FIGS. 17A-17B. The control system 100 determines 1702 the internal temperature of the inner chamber 54 and compares 1704 the internal temperature to the predetermined threshold. When one of the sensors 114a within the inner chamber 54 indicate that the internal temperature of the inner chamber 54 has fallen below the predetermined threshold temperature, or below a lower limit of the predetermined threshold, and when the coefficient of performance of the TEC 94 is determined 1708, 1710 to be greater than 1, the controller 106 directs the temperature management system 60 to enter the first heating mode 1700. In the first heating mode 1700, the TEC 94 is operated 1706 to heat the inner chamber 54.

Additionally, the fan 72 is operated 1712 to transfer heat from the ambient air to the heat sink 74 to heat the inner chamber 54. In the first heating mode 1700 where the COP is greater than 1, as shown in FIGS. 17A-17B, the control system 100 operates the fan 72 to bring in ambient air, transferring heat from the ambient environment to the heat sink and then to the first end of the heat pipe 80. The heat pipe 80 transfers this heat from the first end of the heat pipe 80 to the second end of the heat pipe 80 coupled to the TEC sink 92. Additionally, the control system 100 directs the power source 102 to power the TEC 94. The power consumption by the TEC 94 generates additional heat.

Accordingly, the total heat added to the inner chamber 54 comes from both heat pumped into the system 10 from the ambient environment via the heat pipe 80 and heat generated by power consumption from the TEC 94. This dual-source heating means the heat pipe 80 transfers less total heat in heating mode compared to cooling mode.

In an embodiment, the method comprises insulating the inner chamber 54 from the ambient environment with the water-based heat pipe 80 when the coefficient of performance is below 1. The water-based heat pipe 80 may transition from efficiently transferring thermal energy through vapor exchange above 20° C. to providing thermal resistance below 20° C., which corresponds to when the coefficient of performance of the TEC 94 transitions from above 1 to below 1.

Figure 18A:
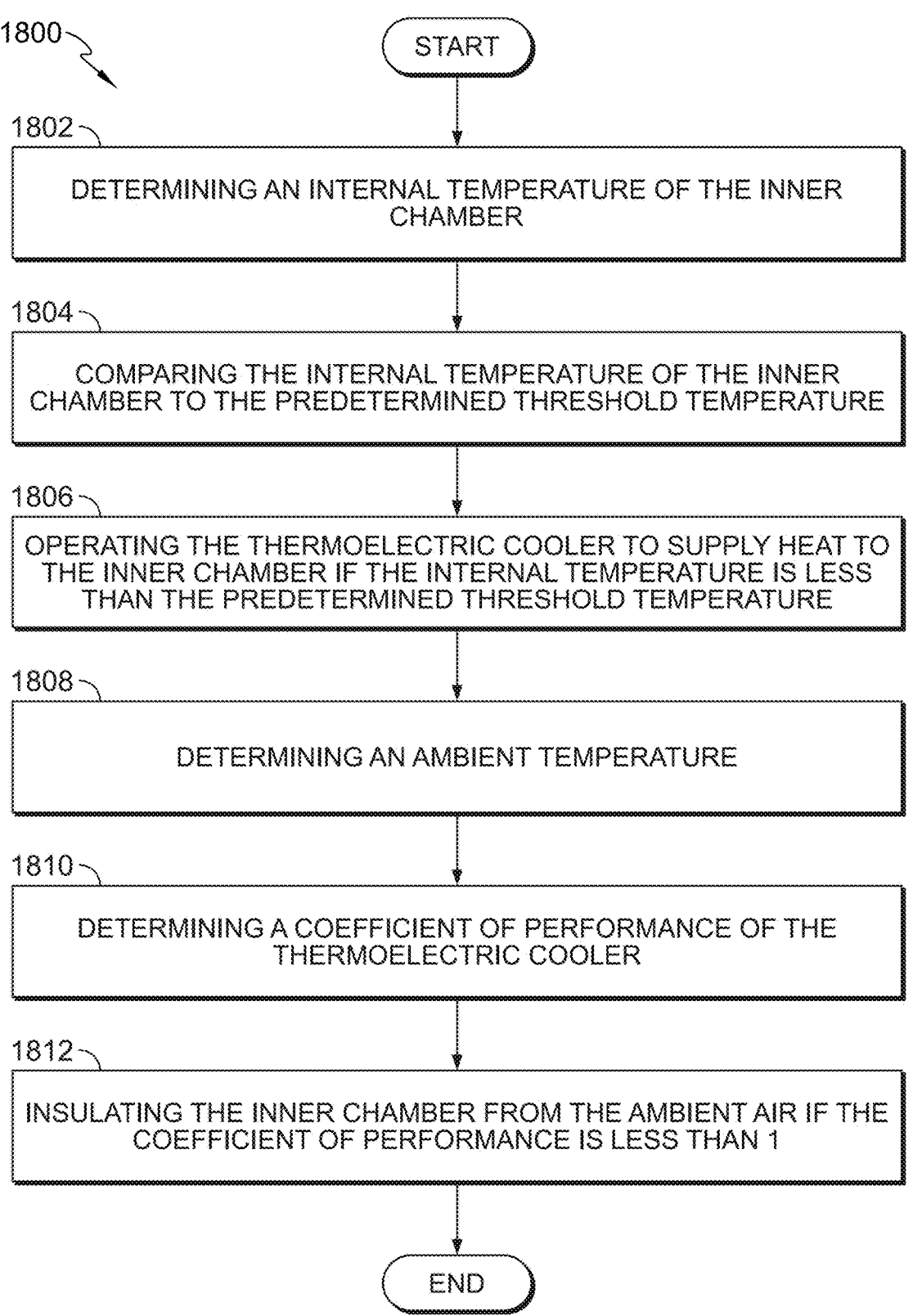
FIG. 18A is a diagram of a method of a second heating mode of the portable incubation system of FIG. 1.
Figure 18B:
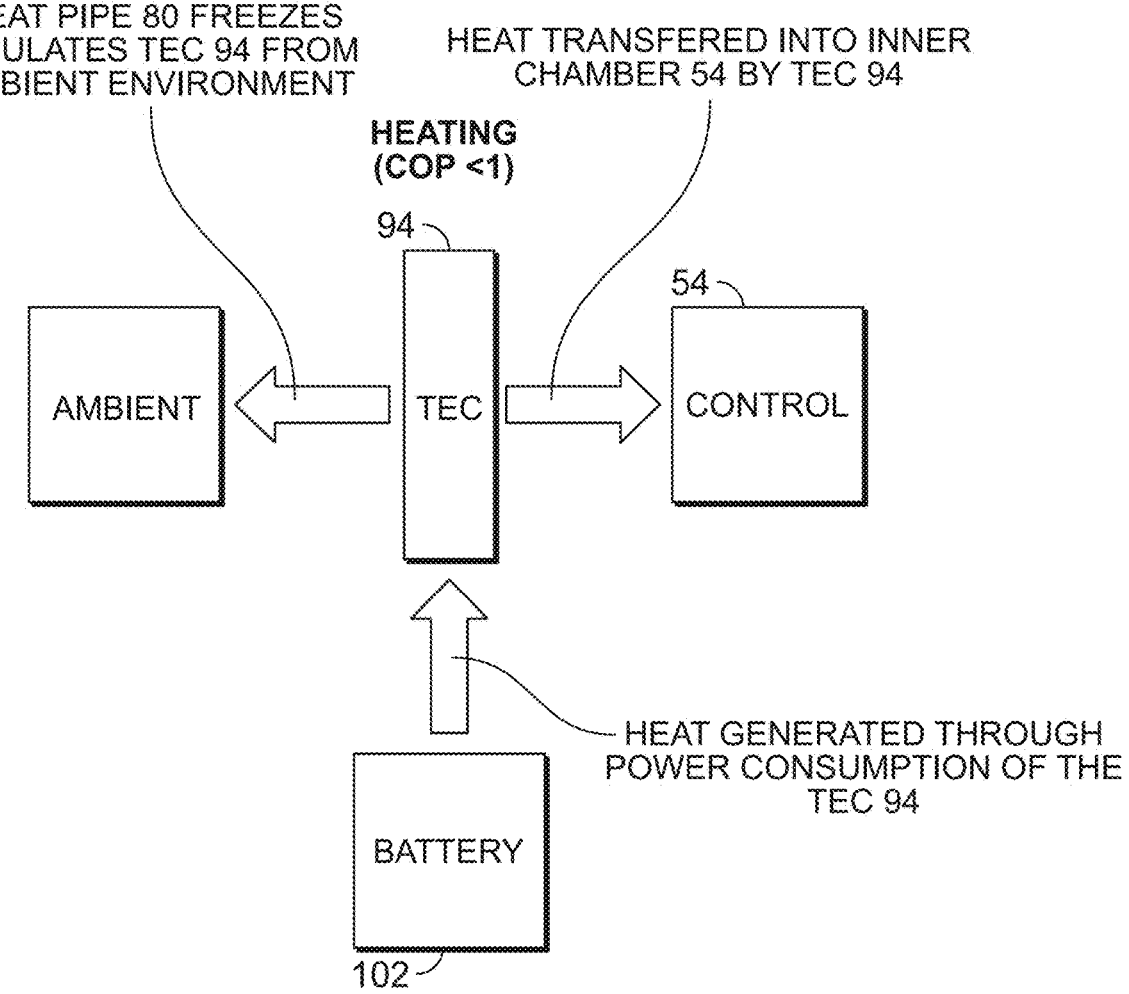
FIG. 18B is a diagram of the portable incubation system of FIG. 1 in the second heating mode.

At very low temperatures, when the TEC's COP drops below 1, as shown in FIGS. 18A-18B, the system's behavior changes. The second heating mode 1800 is shown in FIGS. 18A-18B. The control system 100 determines 1802 the internal temperature of the inner chamber 54 and compares 1804 the internal temperature to the predetermined threshold. When one of the sensors 114a within the inner chamber 54 indicates that the internal temperature of the inner chamber 54 has fallen below the predetermined threshold temperature, and when the coefficient of performance of the TEC 94 is determined 1808, 1810 to be less than 1, the controller 106 directs the temperature management system 60 to enter the second heating mode 1800. In the second heating mode 1800, the TEC 94 is operated 1806 to heat the inner chamber 54. Additionally, the temperature management system 60 is operated to insulate 1812 the inner chamber 54 from the ambient environment via the heat pipe 80. This is due to the freezing of the working fluid in the water-based heat pipe 80 and by stopping operation of the fan 72 if it was previously running.

In the second heating mode when the COP is less than 1, the heat pipe 80 transitions to conduction-only operation as the water, which operates as the working fluid in the heat pipe 80, freezes and can no longer transfer heat through vaporization and condensation of the water. Accordingly, as shown in FIGS. 18A-18B, the control system 100 turns off or does not operate the fan 72, reducing heat transfer between the ambient environment and the inner chamber 54 from the ambient environment via the heat pipe 80. Instead, the heat pipe 80 acts as an insulator between the ambient environment and the inner chamber 54. In this mode, the control system 100 directs the power source 102 to power the TEC 94, and heat is only transferred into the inner chamber through power consumption of the TEC 94.

Advantageously, this reduced heat transfer capability of the heat pipe 80 improves system efficiency by effectively insulating the ambient-facing side of the TEC 94 (the side of the TEC 94 coupled to the heat pipe 80 via the TEC sink 92), reducing the temperature differential across the TEC 94 and thereby improving the performance of the TEC 94 in maintaining the chamber temperature. This unique integration of the water-based heat pipe 80 and single TEC 94 enables complete enclosure of the inner chamber 54 with vacuum insulated panels 52, 53.

This design provides certain advantages over conventional designs that require one face of a temperature controlled chamber to remain open for TEC and heat sink placement. For example, the ability to fully enclose the inner chamber 54 with vacuum insulated panels 52 is particularly advantageous because it minimizes thermal losses through the container walls. Traditional designs that require direct TEC placement against a chamber wall create thermal weak points in the insulation that are susceptible to unwanted thermal transfer, for example, heat loss from the inner chamber to the ambient environment. The present invention overcomes this limitation by using the heat pipe 80 to transfer heat through a small penetration in the insulation while maintaining the thermal barrier. Additionally, when the ambient environment is cool enough to slow operation or freeze the working fluid within the heat pipe 80, the heat pipe 80 actually transitions to an insulator and further insulates the inner chamber 54 from the cold ambient environment, instead of facilitating further heat loss.

Figure 16A:
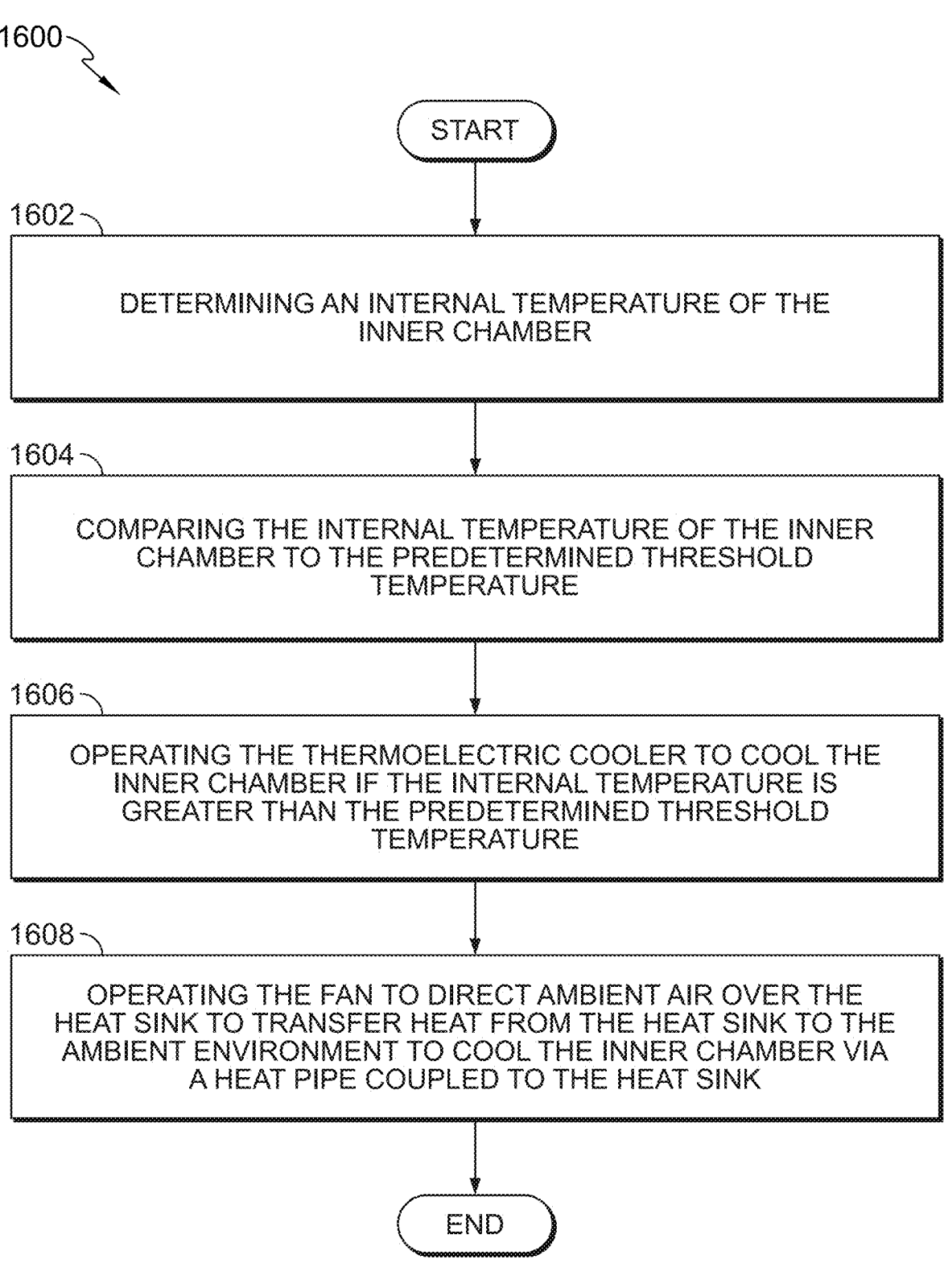
FIG. 16A is a diagram of a method of a cooling mode of the portable incubation system of FIG. 1.
Figure 16B:
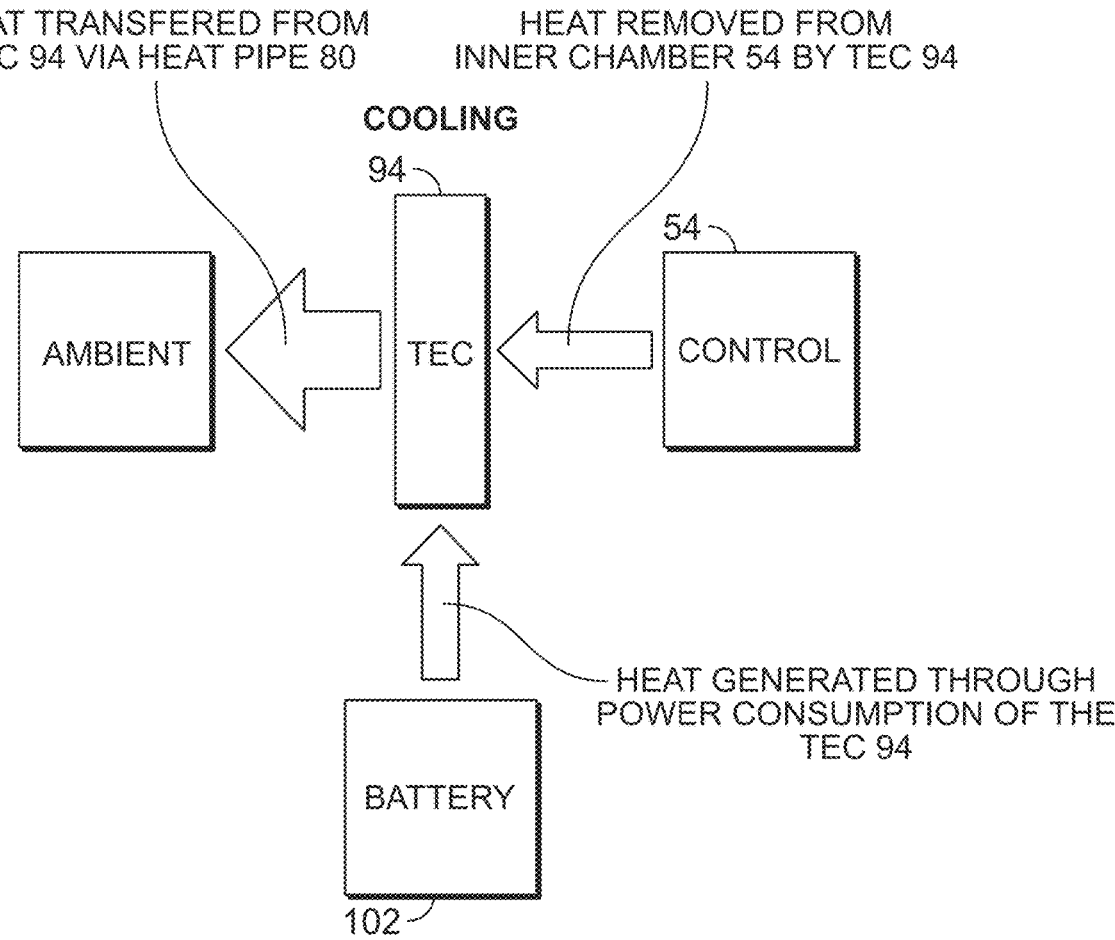
FIG. 16B is a diagram of the portable incubation system of FIG. 1 in cooling mode.

The cooling mode 1600 is shown in FIGS. 16A-16B. The control system 100 determines 1602 the internal temperature of the inner chamber 54 and compares 1604 the internal temperature to the predetermined threshold. When one of the sensors 114a within the inner chamber 54 indicates that the internal temperature of the inner chamber 54 has risen above the predetermined threshold temperature, or is above an upper limit of the predetermined threshold, the controller 106 directs the temperature management system 60 to enter cooling mode 1600. The TEC 94 is operated 1606 to cool the inner chamber 54 and the fan 72 is operated 1608 to transfer heat from the heat sink 74 to the ambient air.

In cooling mode, as shown in FIGS. 16A-16B, the heat pipe 80 transfers both heat removed from the inner chamber 54 and heat generated by the TEC 94 (from consuming power supplied by the power source 102). For example, if the TEC 94 consumes 1 W of power, the heat pipe 80 transfers this 1 W plus any heat removed from the inner chamber 54. In cooling mode, the heat transfer requirements of the heat pipe 80 are relatively greater than the other modes described herein.

The performance of the heat pipe 80 becomes more critical in cooling mode due to the relatively higher heat loads and heat transfer requirements. As more heat transfers across the heat pipe 80, the temperature differential between the inner chamber 54 and the ambient environment increases, reducing the efficiency of the TEC 94.

EXAMPLES

The following examples illustrate operating parameters and configurations of the incubation system. These examples are provided for illustration and are not intended to be limiting.

In one exemplary embodiment, the desired ambient operating range of the incubator is from −40° C. to 70° C. The desired core temperature setpoint or predetermined threshold temperature of the inner chamber 54 is 38.5° C. This setpoint represents a typical temperature requirement for maintaining certain biological samples, such as embryos, oocytes, gametes, and other reproductive materials. Based on these values, the COP of the TEC 94 drops below 1 when the ambient temperature drops below approximately 20° C.

Accordingly, during operation, when the temperature sensors detect that the internal temperature of the inner chamber 54 drops below 38.5° C. and that the external temperature is below 20° C., the control system 100 directs the incubation system 10 to enter the second heating mode, reducing heat transfer from the ambient environment via the heat pipe 80. When the temperature sensors detect that the internal temperature of the inner chamber 54 drops below 38.5° C. and that the external temperature is above 20° C., the control system 100 directs the incubation system 10 to enter the first heating mode, turning on the fan to supplement heat provided by the TEC 94 with heat transferred from the ambient environment via the heat pipe 80. When the temperature sensors detect that the internal temperature of the inner chamber 54 rises above 38.5° C., the control system 100 directs the incubation system 10 to enter cooling mode.

Heat Pipe Orientation and Shipping Configurations

In an embodiment, the portable incubation system 10 comprises a shipping case configured to accommodate the portable incubation system 10 in either a vertical orientation or a horizontal orientation. The shipping case may comprise a first set of ventilation openings aligned with a vent of the temperature management system when the portable incubation system 10 is in the vertical orientation. The shipping case may comprise a second set of ventilation openings aligned with the vent when the portable incubation system 10 is in the horizontal orientation.

The incubation system 10 may be used to ship biological samples. Different shipping configurations of the incubation system 10, in which the container 20 is oriented differently, may be used during transport. Two exemplary orientations are shown in FIGS. 19A-20B. The arrow on the left side of each of FIGS. 19A-20B is a reference arrow to show the upwards direction relative to the ground and/or an underlying surface. In other words, the direction of the arrow is constant and points upwards in the opposite direction of gravity, where the orientation of the portable incubation system 10 differs from FIGS. 19A-B to FIGS. 20A-B relative to the constant reference arrow and an underlying surface.

Figure 19A:
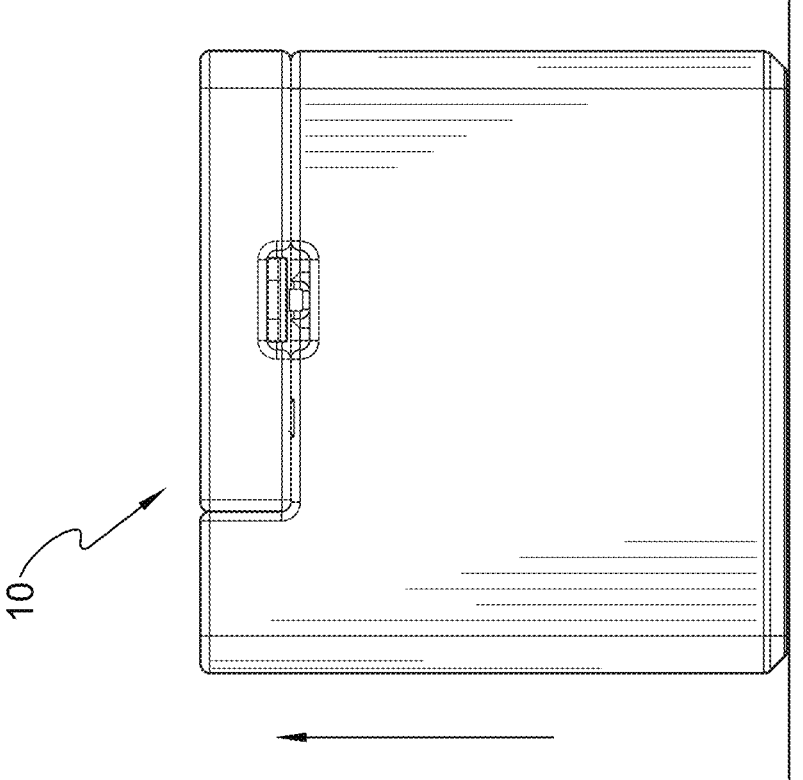
FIG. 19A is a front view of portable incubation system of FIG. 1 in a first shipping orientation.

FIGS. 19A-19B show a first shipping configuration, or vertical orientation, in which the container 20 is oriented with the lid 30 facing upwards or forming a top, upper surface of the incubation system 10 and the heat pipe 80 is oriented horizontally, relative to the underlying surface, as it extends between the TEC 94 and the heat sink assembly 70. In a second shipping configuration, or horizontal orientation, shown in FIGS. 20A-20B, the container 20 is oriented with the lid 30 facing sideways or forming a side surface of the incubation system 10 and the heat pipe 80 is oriented vertically relative to the underlying surface.

In the exemplary embodiment shown in FIGS. 20A-20B, the incubation system 10 may be shipped such that the heat pipe 80 is oriented vertically, with the ends of the heat pipe 80 stacked one above the other. The orientation of the heat pipe 80 can affect its heat transfer efficiency due to the role of gravity in the condensate return process. In vertical shipping configurations, the heat pipe 80 orientation (where the heat sink 74 is positioned above the TEC 94) enhances cooling efficiency as vapor naturally rises. This orientation may slightly reduce heating performance between 20° C. and 38.5° C., though the lower heat requirements in this range may make this impact negligible. Below 20° C., when vapor exchange ceases, orientation has no effect on performance. In horizontal shipping configurations, as shown in the figures, the heat pipe 80 maintains high efficiency without this additional benefit.

In an embodiment, the inner chamber assembly 50 comprises a first inner block 56a configured to hold biological sample containers in a vertical orientation when the portable incubation system 10 is operated in a vertical configuration. In an embodiment, the inner chamber assembly 50 comprises a second inner block 56b configured to hold biological sample containers in a horizontal orientation when the portable incubation system 10 is operated in a horizontal configuration.

The different shipping configurations of the incubation system 10 not only affect the heat pipe performance as described above but also accommodate the specific orientation requirements of different biological samples being transported. As previously discussed, certain biological samples may require specific orientations during transport to maintain their viability. For example, embryo straws are typically maintained in a horizontal position during transport to prevent the embryo from migrating to one end of the straw, while tubes containing collected oocytes typically require a vertical orientation for optimal preservation.

The first, vertical shipping configuration shown in FIGS. 19A-19B, where the container 20 is oriented with the lid 30 facing upwards, is particularly suited for transporting biological samples such as oocytes in tubes and/or vials that require vertical positioning. In this configuration, the inner blocks 56a can be arranged with openings 57a designed to hold tubes in a vertical orientation, allowing proper preservation of these samples during transport.

The second shipping configuration shown in FIGS. 20A-20B, where the container 20 is oriented with the lid 30 facing sideways, is well-suited for transporting biological samples such as embryos in straws that must be maintained horizontally. In this configuration, the inner blocks 56b can be arranged with elongated horizontal openings 57b designed to securely hold straws in the required horizontal position throughout transport.

The versatility of the incubation system 10 in operating effectively in either orientation enables transportation of different types of biological samples with their specific orientation requirements. This dual-orientation capability is a result of the incubation system's design, which ensures that all components—including the sealing mechanism of the lid 30, the temperature management system 60, and the control system 100—function properly regardless of the incubation system's orientation during transport. The inner blocks 56 may be specifically designed for each orientation, with appropriately shaped openings 57 to accommodate the particular sample containers being used in either the vertical or horizontal configuration.

Shipping Case for Multi-Orientation Incubation System

The portable incubation system 10 may be further transported within a protective shipping case 2100 designed specifically to accommodate the system in multiple orientations. Unlike conventional solutions that require separate incubators for different biological sample containers (e.g., one incubator for horizontal straws and another for vertical tubes), the present invention's dual-orientation capability eliminates this redundancy. The shipping case 2100 enhances this versatility through thoughtful design features.

The shipping case 2100 may comprise a durable outer shell, such as those commonly used for sensitive equipment (e.g., a Pelican™-style case). In some embodiments, the shipping case 2100 contains customized internal foam inserts 2118 shaped to securely hold the incubation system 10 in either vertical or horizontal orientation. Critically, the shipping case 2100 may include multiple ventilation openings 2120 positioned to align with the heat sink assembly's vent 29 in one or both orientations. In an embodiment, when the incubation system 10 is placed in vertical orientation, one set of ventilation openings 2120b in the shipping case aligns with the vent 29, and when placed in horizontal orientation, a different set of ventilation openings 2120a aligns with the vent 29 in its new position. This dual-ventilation design ensures proper airflow to the heat sink assembly 70 regardless of the incubation system's orientation.

The shipping case 2100 may also include designated compartments for accessories such as extra batteries, power adapters, or additional inner blocks 56 configured for different sample containers. These compartments are positioned to maintain accessibility regardless of which orientation is used for transport. The case may further incorporate external indicators that visually confirm the orientation of the incubation system 10 inside, ensuring handlers maintain the correct position for the specific biological samples being transported.

In an embodiment, the portable incubation system 10 may be placed within a shipping case 2100 configured to accommodate the portable incubation system 10 in either a vertical orientation or a horizontal orientation. The shipping case 2100 may comprise a first set of ventilation openings 2120*b* that align with the vent 29 of the temperature management system 60 when the portable incubation system 10 is in the vertical orientation. The shipping case may comprise a second set of ventilation openings 2120*a* that align with the vent 29 when the portable incubation system 10 is in the horizontal orientation.

Figure 21:
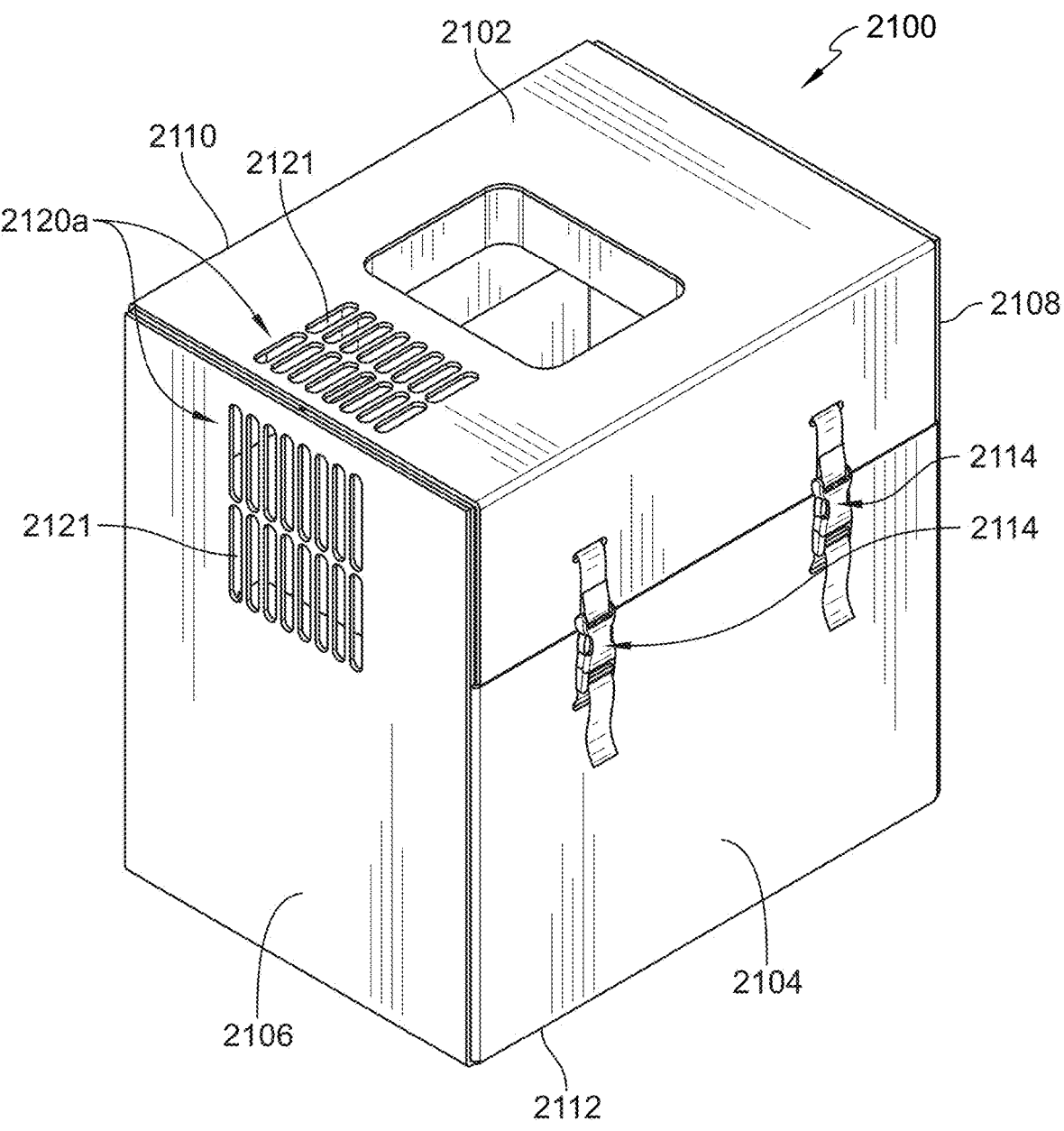
FIG. 21 is a perspective view of a shipping case configured to accommodate the portable incubation system in either the vertical orientation or the horizontal orientation and showing a first set of ventilation openings in the shipping case.
Figure 22:
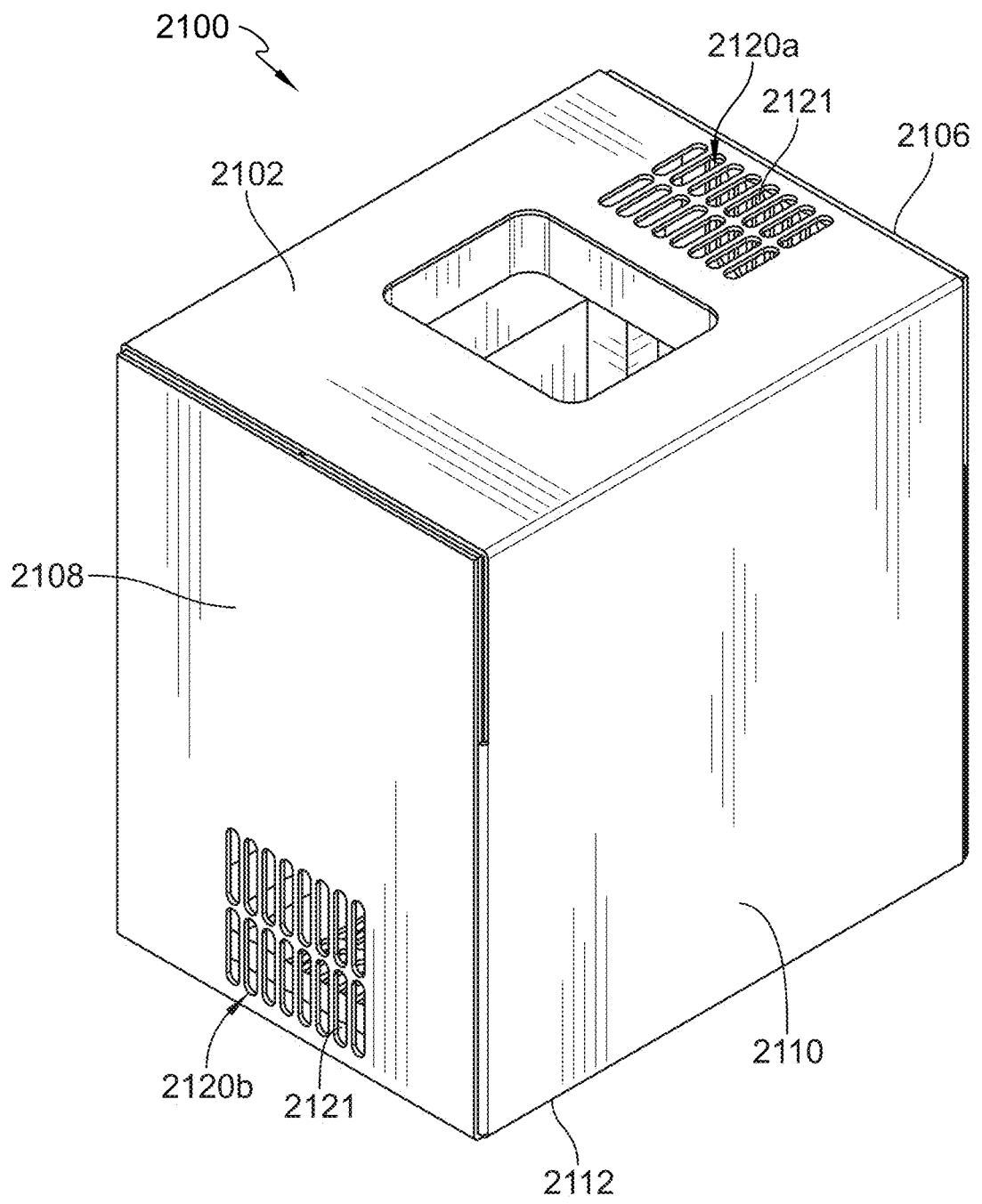
FIG. 22 is a rear perspective view of the shipping case of FIG. 21, showing a portion of the first set of ventilation openings and a portion of a second set of ventilation openings in the shipping case.
Figure 23:
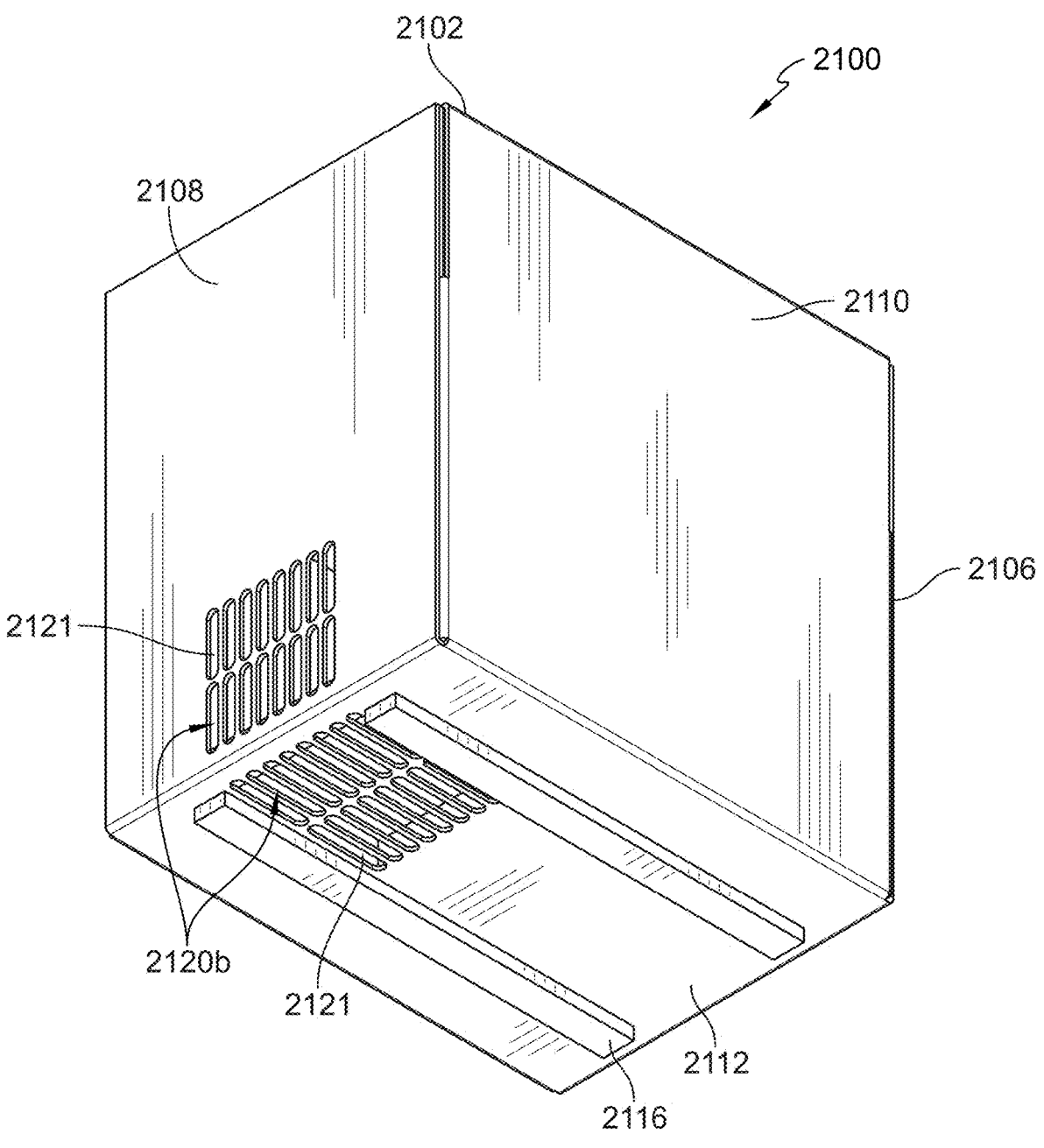
FIG. 23 is a bottom, rear perspective view of the shipping case of FIG. 21, showing the second set of ventilation openings.
Figure 24:
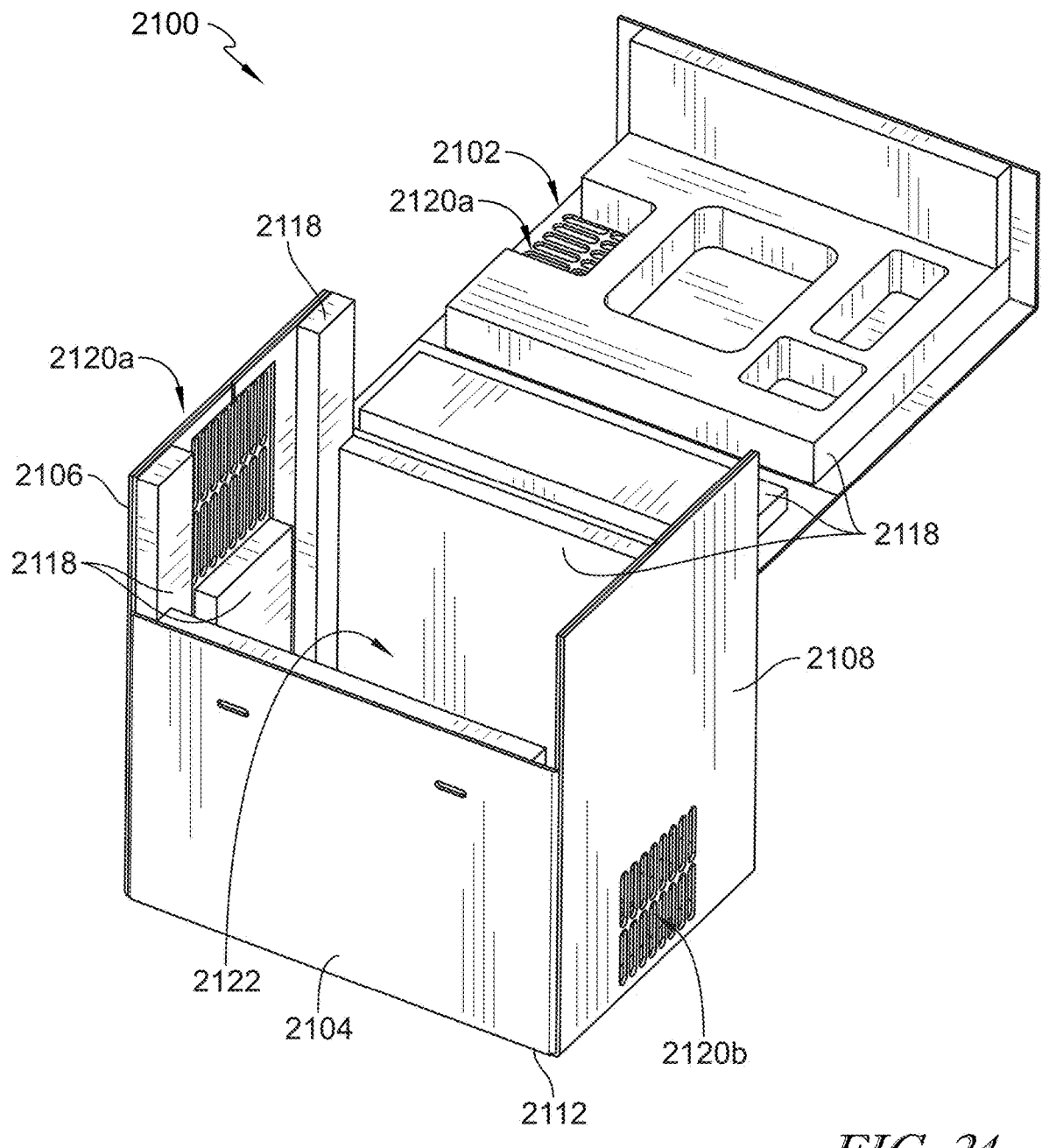
FIG. 24 is a perspective view of the shipping case of FIG. 21 with a lid of the shipping case open to show an interior cavity of the shipping case.
Figure 25:
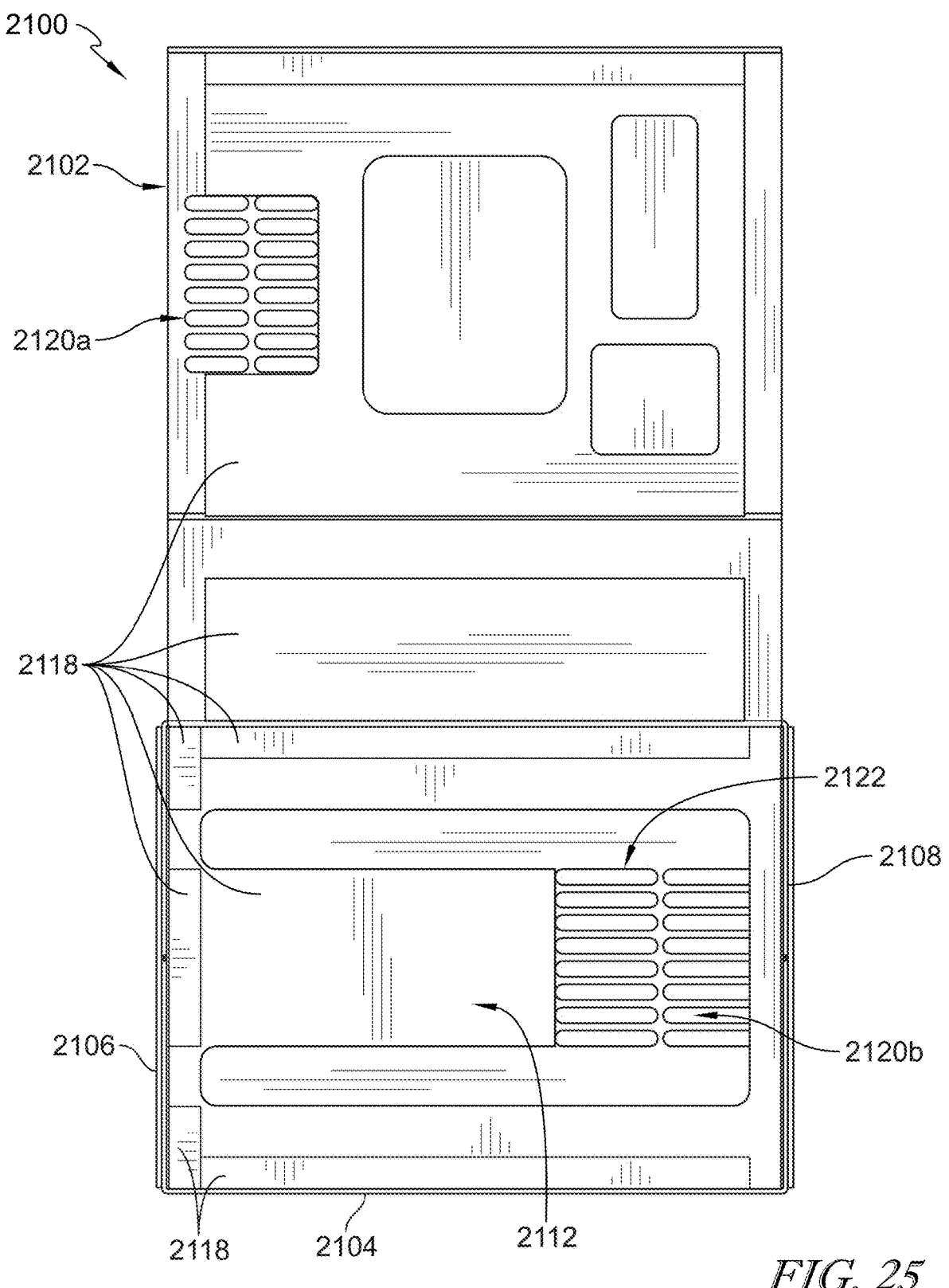
FIG. 25 is a top view of the open shipping case of FIG. 24, showing a view of the interior cavity of the shipping case.

As shown in FIGS. 21-25, in an embodiment outer shell of the shipping case 2100 comprises a top panel or lid 2102, a front panel 2104, a back panel 2110, a right side panel 2108, and/or a left side panel 2106 that form an interior cavity 2122 of the shipping case 2100. The lid 2102 may be coupled to the back panel 2110, for example, by hinges such that the lid 2102 can be opened to place the portable incubation system 10 within and/or remove the portable incubation system 10 from the interior cavity 2122. FIGS. 21-23 show the shipping case 2100 with the lid 2102 in a closed configuration. FIGS. 24-25 show the shipping case 2100 with the lid 2102 in the open configuration. Fasteners 2114 may be coupled to the lid 2102 and/or the front panel 2104 such that the lid 2102 may be fastened and/or secured in the closed configuration to retain the portable incubation system 10 within the shipping case 2100, for example, during transport.

The shipping case 2100 may comprise interior padding 2118 coupled with the lid and/or panels to protect and cushion the portable incubation system 10 during transport. Additionally or alternatively, the padding 2118 may fill any gaps between inner surfaces of the panels of the shipping case 2100 and the portable incubation system 10 such that the portable incubation system 10 does not move around within the shipping case 2100. The shipping case 2100 may comprise supports and/or feet 2116 on the bottom panel 2112 of the shipping case 2100 to protect the shipping case from an underlying surface, provide a level base for the shipping case 2100, and/or to offset the bottom panel 2112 from an underlying surface to allow airflow flow between the ambient environment and the heat sink assembly 70 and/or fan 72 of the portable incubation system 10 through the vent 29.

Air flow through the vent may be how the temperature management system 60 transfers heat between the inner chamber 54 of the portable incubation system 10 and the ambient environment. Air flow through the vent 29 and/or sets of ventilation openings 2120 may be directed and/or powered by the fan 72. Heat may be transferred between the temperature management and the ambient environment by utilizing the heat sink assembly 70. The fan 72 and the heat sink assembly 70 may be positioned within the housing 40 to align with the vent 29, In an embodiment, the shipping case 2112 comprises a first, top set of ventilation openings 2120*a* and a second, bottom set of ventilation openings 2120*b*. The multiple sets of ventilation openings 2120*a*, 2102*b* allow for better thermal communication between the temperature management system 60 and the ambient environment regardless of whether the portable incubation system is in the vertical or horizontal shipping orientation. Each set of ventilation openings 2120 may comprise one or more individual apertures or ventilation openings 2121 disposed within the panels. The openings 2121 extend through the panel and/or padding 2118 to allow an open flow path between the temperature management system 60 and the ambient environment and enable the portable incubation system 10 to transfer heat between the ambient environment and the inner chamber 54.

Figures 27A, 27B:
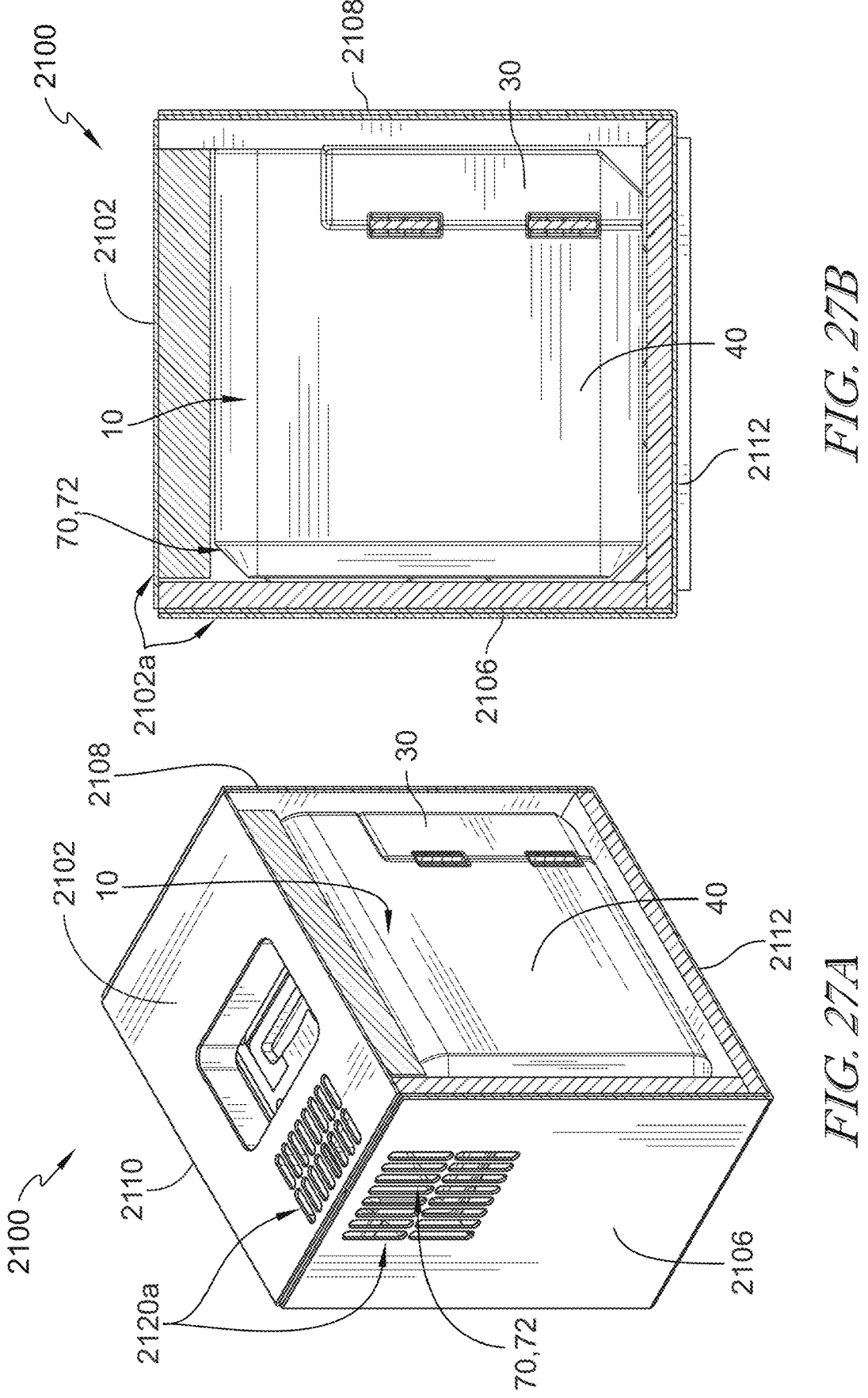
FIG. 27A is a perspective view of the shipping case of FIG. 21 with a side of the shipping case removed to show the orientation of the portable incubation system within the shipping case when the portable incubation system in in the horizontal orientation, and to show that the vent of the portable incubation system aligns with the first set of vets of the shipping case when the portable incubation system is in the horizontal orientation.
FIG. 27B is a side view of the shipping case of FIG. 27A with the side removed, showing the portable incubation system in the horizontal orientation within the shipping case.

In an embodiment, as shown in FIGS. 27A-27B, the top panel 2102 and the left side panel 2106 are shaped to define the first, top set of ventilation openings 2120*a*. The ventilation openings 2120*a* may be disposed near the edge of the shipping case 2100 where the left side panel 2106 meets and/or intersects the top panel 2102. In an embodiment, the first set of ventilation openings 2102*a* align with the vent 29 of the container 20 when the portable incubation system 10 is in the horizontal shipping configuration, with the lid 30 positioned on the side of the container 20 such that the portable incubation system opens to the side and/or the heat pipe 80 extends in the vertical direction. In this orientation, the vent 29 of the container 20, which allows for airflow between the heat sink assembly 70 and/or the fan 72 and the ambient environment, is aligned with the first set of ventilation openings 2120*a*.

Figures 26A, 26B:
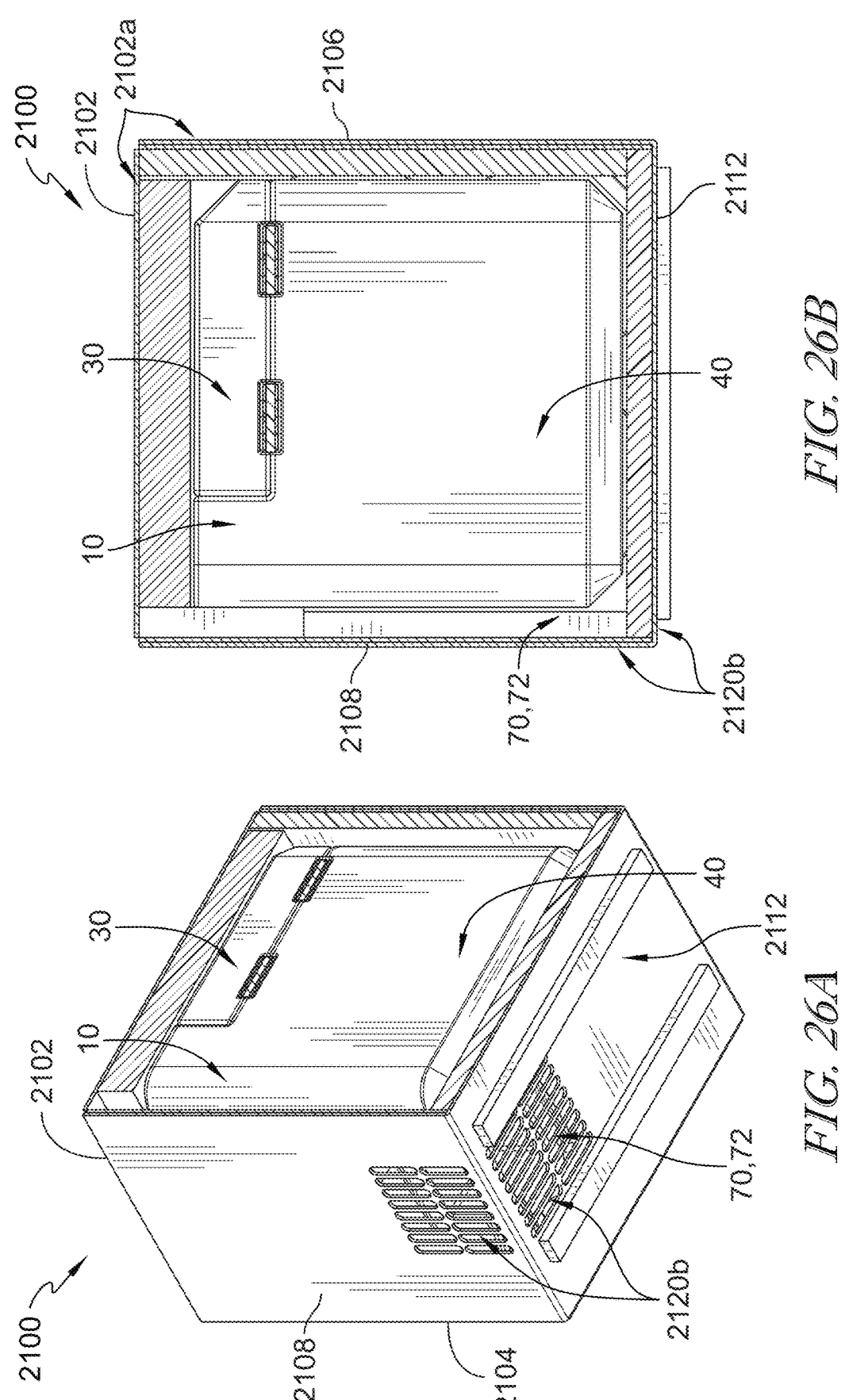
FIG. 26A is a bottom perspective view of the shipping case of FIG. 21 with a side of the shipping case removed to show the orientation of the portable incubation system within the shipping case when the portable incubation system in in the vertical orientation, and to show that vent of the portable incubation system aligns with the second set of vets of the shipping case when the portable incubation system is in the vertical orientation.
FIG. 26B is a side view of the shipping case of FIG. 26A with the side removed, showing the portable incubation system in the vertical orientation within the shipping case.

In an embodiment, as shown in FIGS. 26A-26B, the bottom panel 2112 and the right side panel 2108 are shaped to define the second, bottom set of ventilation openings 2120*b*. The ventilation openings 2120*b* may be disposed near the edge of the shipping case 2100 where the right side panel 2108 meets and/or intersects the bottom panel 2112. In an embodiment, the second set of ventilation openings 2102*b* align with the vent 29 of the container 20 when the portable incubation system 10 is in the vertical shipping configuration, with the lid 30 positioned on the top of the container 20 such that the portable incubation system opens upwards and the heat pipe 80 extends in the horizontal direction. In this orientation, the vent 29 of the container 20, which allows for airflow between the heat sink assembly 70 and/or fan 72 and the ambient environment, is aligned with the second set of ventilation openings 2120*b*. The feet 2116 may offset the shipping case 2100 from an underlying surface such that airflow can still be achieved through the vent openings 2121 formed in the bottom panel 2112 even when the shipping case 2100 is set down on an underlying surface.

The combination of the portable incubation system 10 with its orientation-adaptable design and the specially designed shipping case creates a complete transport solution that provides significant advantages over conventional approaches. While competitive systems typically require purchasing separate incubators for different sample types (horizontal straws versus vertical tubes), the present invention allows a single device to accommodate both configurations. This versatility reduces equipment costs, simplifies inventory management, and increases operational flexibility for facilities that handle multiple types of biological samples.

TEC/Heat Sink Combinations

Cascaded or stacked TECs, which are better suited for higher or lower setpoint devices where a higher ΔT across the TEC is needed, introduce additional complexity and efficiency losses. The single TEC 94 in the incubation system 10 described herein and shown in the figures reduces these losses and complexities. For example, the use of a single TEC 94 may simplify control algorithms and reduce thermal resistance in the heat transfer path. The sizing of the TEC 94 is based on calculated heat loss through the insulation. In particular, the TEC 94 may be sized for minimal heat loss in extreme cold. The design choice may be unexpected or counter to the standard practice of optimizing for most efficient cooling and represents a novel approach to portable incubation system design.

ADDITIONAL VARIATIONS

The exact temperature at which the incubation system 10 transitions past a COP of 1 may vary, but is estimated to occur between 20° C. and 0° C. This may change based on a variety of factors. These factors include the specific model and specifications of the TEC 94 used, the thermal resistance of the heat transfer path, and the efficiency of the heat sink 74 design. Different heat pipe 80 lengths may adjust the magnitude of this effect. Longer heat pipes 80 generally introduce additional thermal resistance, while shorter heat pipes 80 may provide more efficient heat transfer but limit design flexibility. Alternative working fluids within the heat pipe 80 could affect both the temperature range where vapor transfer is effective and the heat transfer capacity of the heat pipe 80.

The present disclosure has been described with reference to particular embodiments having various features. It will be apparent to those skilled in the art that various modifications and variations can be made in the practice of the present disclosure without departing from the scope or spirit of the invention. One skilled in the art will recognize that these features may be used singularly or in any combination based on the requirements and specifications of a given application or design. Other embodiments of the disclosure will be apparent to those skilled in the art from consideration of the specification and practice of the invention disclosed herein. While the foregoing specification has described with reference to specific embodiments, those skilled in the art will recognize that various features and characteristics described above can be combined in different ways to produce numerous additional embodiments. The scope of protection is defined by the appended claims, and any modifications, alterations, and changes that come within that scope and their equivalents are encompassed by the present disclosure. Features shown in one embodiment can be employed in other embodiments. It is intended that the specification and examples be considered as exemplary in nature and that variations that do not depart from the essence of the invention are intended to be within the scope of the appended claims.

What is claimed is:
1. A portable incubation system comprising:
a container comprising a housing forming an outer wall of the container and an inner chamber assembly disposed within the housing;
a temperature management system disposed within the housing comprising a heat sink assembly in thermal communication with an ambient environment of the portable incubation system, a thermoelectric cooler assembly coupled to the inner chamber assembly, and a water-based heat pipe extending between the heat sink assembly and the thermoelectric cooler assembly; and
a controller configured to direct the temperature management system to regulate a temperature of the inner chamber assembly based on an ambient temperature, wherein the controller is configured to:
determine a coefficient of performance (COP) of the thermoelectric cooler assembly based on a temperature differential between the inner chamber assembly and the ambient environment;
operate the temperature management system in a first heating mode when the COP is greater than 1, wherein the first heating mode utilizes both the thermoelectric cooler assembly and ambient heat transfer by way of the water-based heat pipe; and
operate the temperature management system in a second heating mode when the COP is less than 1, wherein the second heating mode utilizes the water-based heat pipe as thermal insulation between the thermoelectric cooler assembly and the ambient environment.

2. A portable incubation system comprising:
a container comprising a housing forming an outer wall of the container and an inner chamber assembly disposed within the housing;
a temperature management system disposed within the housing comprising a heat sink assembly in thermal communication with an ambient environment of the portable incubation system, a thermoelectric cooler assembly coupled to the inner chamber assembly, and a water-based heat pipe extending between the heat sink assembly and the thermoelectric cooler assembly;
a controller configured to direct the temperature management system to regulate a temperature of the inner chamber assembly based on an ambient temperature; and
a control system comprising the controller and a plurality of temperature sensors disposed in the portable incubation system;
wherein:
the controller is configured to direct the temperature management system to regulate a temperature of the inner chamber assembly by operating at least one of the fan or the thermoelectric cooler;
the controller is configured to seamlessly transition between a cooling mode, a first heating mode, and a second heating mode based on continuous sensor feedback; and
the transition points between modes are determined by both an internal temperature of the inner chamber assembly relative to a predetermined threshold temperature and the ambient temperature relative to a coefficient of performance transition point.

3. A portable incubation system comprising:
a container comprising a housing forming an outer wall of the container and an inner chamber assembly disposed within the housing;
a temperature management system disposed within the housing comprising: a heat sink assembly in thermal communication with an ambient environment of the portable incubation system; a thermoelectric cooler assembly coupled to the inner chamber assembly and comprising a thermoelectric cooler; a water-based heat pipe extending between the heat sink assembly and the thermoelectric cooler assembly, and a fan configured to direct ambient air over the heat sink assembly; and
a controller configured to direct the temperature management system to regulate a temperature of the inner chamber assembly based on an ambient temperature by operating at least one of the fan or the thermoelectric cooler, and wherein the controller is further configured to:

determine a coefficient of performance (COP) of the thermoelectric cooler based on a difference in temperature across the water-based heat pipe;

operate the temperature management system in a first heating mode when the COP is greater than 1, wherein the first heating mode comprises operating both the thermoelectric cooler and the fan to transfer heat from the ambient environment by way of the water-based heat pipe; and operate the temperature management system in a second heating mode when the COP is less than 1, wherein the second heating mode comprises operating the thermoelectric cooler and not operating the fan, utilizing the reduced heat transfer capability of the water-based heat pipe as thermal insulation.

\* \* \* \* \*